US011123422B2

(12) United States Patent
Thompson et al.

(10) Patent No.: US 11,123,422 B2
(45) Date of Patent: Sep. 21, 2021

(54) IMMUNOGENIC COMPOSITION

(71) Applicant: Oxford University Innovation Limited, Oxford (GB)

(72) Inventors: Craig Thompson, Oxford (GB); Sunetra Gupta, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/326,749

(22) PCT Filed: Aug. 25, 2017

(86) PCT No.: PCT/GB2017/052510

§ 371 (c)(1),
(2) Date: Feb. 20, 2019

(87) PCT Pub. No.: WO2018/037246

PCT Pub. Date: Mar. 1, 2018

(65) Prior Publication Data

US 2019/0201521 A1 Jul. 4, 2019

(30) Foreign Application Priority Data

Aug. 25, 2016 (GB) ..................................... 1614485

(51) Int. Cl.

| | |
|---|---|
| ***A61K 39/145*** | (2006.01) |
| ***C07K 16/08*** | (2006.01) |
| ***A61P 31/16*** | (2006.01) |
| ***C07K 16/10*** | (2006.01) |
| ***A61K 39/285*** | (2006.01) |
| ***A61K 39/39*** | (2006.01) |
| *A61K 39/00* | (2006.01) |

(52) U.S. Cl.

CPC .......... *A61K 39/145* (2013.01); *A61K 39/285* (2013.01); *A61K 39/39* (2013.01); *A61P 31/16* (2018.01); *C07K 16/08* (2013.01); *C07K 16/1018* (2013.01); *A61K 2039/5258* (2013.01)

(58) Field of Classification Search

None

See application file for complete search history.

(56) References Cited

U.S. PATENT DOCUMENTS

| | | | | |
|---|---|---|---|---|
| 4,235,877 A | 11/1980 | Fullerton | | |
| 2008/0187557 A1* | 8/2008 | Sambhara | A61K 39/12 | 424/233.1 |
| 2012/0039899 A1* | 2/2012 | Olsen | A61K 45/06 | 424/142.1 |

FOREIGN PATENT DOCUMENTS

| | | |
|---|---|---|
| EP | 0 498 905 A1 | 8/1992 |
| WO | 2012/36993 A | 3/2012 |
| WO | 2012/089833 A2 | 7/2012 |
| WO | 2013/177444 A2 | 11/2013 |
| WO | 2014/153674 A1 | 10/2014 |

OTHER PUBLICATIONS

Presanis, A.M. et al., “Changes in severity of 2009 pandemic A/H1N1 influenza in England : a Bayesian evidence synthesis”, British Medical Journal, 2011, (343), pp. 1-14.

Miura et al., “Development and Characterization of a Standardized ELISA Including a Reference Serum on Each Plate to Detect Antibodies Induced by Experimental Malaria Vaccines”, 2008 Vaccine 26:193, pp. 1-18.

Lozano, R. et al., 2012. Global and regional mortality from 235 causes of death for 20 age groups in 1990 and 2010□: a systematic analysis for the Global Burden of Disease Study 2010. Lancet, 380, pp. 2095-2128.

Caton et al., 1982. The antigenic structure of the influenza virus A/PR/8/34 hemagglutinin (H1 subtype). Cell, 31(2 Pt 1), pp. 417-427.

Kringelum et al., Structural analysis of B-cell epitopes in antibody:protein complexes, Center for Biological Sequence Analysis, Department of Systems Biology, Technical University of Denmark, Kemitorvet, Building 208, DK-2800 Lyngby, Denmark, Mol Immunol. Jan. 2013 ; 53(1-2): 24-34.

Krammer, F. et al., 2013. Broadly Protective Stalk-Specific Antibodies, 87(12), pp. 6542-6550.

Taubenberger, J.K. & Morens, D.M., 2006. 1918 Influenza: the Mother of All Pandemics. Lancet, 12(1), pp. 15-22.

Von Itzstein, 2007. The war against influenza: discovery and development of sialidase inhibitors, Nature Reviews|Drug Discovery, vol. 6, Dec. 2007, pp. 967-974.

Truscott et al., 2012. Essential epidemiological mechanisms underpinning the transmission dynamics of seasonal influenza, R. Soc. Interface (2012) 9,304-312, Published online Jun. 29, 2011.

Ferguson et al., 2003. Ecological and immunological determinants of influenza evolution, Nature | vol. 422 | Mar. 27, 2003 pp. 428-433.

Davies and Cohen, 1996. Interactions of protein antigens with antibodies, Laboratory of Molecular Biology, National Institute of Diabetes, Digestive and Kidney Diseases, National Institutes of Health, Bethesda, MD 20892-0560, Proc. Natl. Acad. Sci. USA vol. 93, pp. 7-12, Jan. 1996.

WHO 2016: Recommended composition of influenza virus vaccines for use in the 2016-2017 northern hemisphere influenza season, World Health Organization, pp. 1-7.

International Search Report for PCT/GB2017/052510, dated Dec. 18, 2017, pp. 1-19.

Y. Iba et al: Epitope at Globular Head of Hemagglutinin in H3N2 Influenza Viruses, Journal of Virology vol. 88, No. 13, Apr. 9, 2014 (Apr. 9, 2014) , pp. 7130-7144.

(Continued)

*Primary Examiner* — Benjamin P Blumel

(74) *Attorney, Agent, or Firm* — Thomas|Horstemeyer, LLP

(57) ABSTRACT

The present invention relates to an immunogenic composition comprising two or more polypeptides. The invention also provides nucleic acid molecules and vectors encoding the polypeptides, and methods of using the compositions, nucleic acid molecules and vectors for the prevention or treatment of influenza.

6 Claims, 29 Drawing Sheets

Specification includes a Sequence Listing.

(56) References Cited

OTHER PUBLICATIONS

Schneemann Anette et al: particle that elicits cross-reactive antibodies to the conserved stem of influenza virus hemagglutinin, Journal of Virology (ONL, American Society for Microbiology, US, vol. 86, No. 21, Nov. 1, 2012 (Nov. 1, 2012), pp. 11686-11697.
J. C. Krause et al: Neutralizing Human Monoclonal Antibody That Recognizes a Conserved, Novel Epitope on the Globular Head of the Influenza H1N1 Virus Hemagglutinin, Journal of Virology, vol. 85, No. 20, Oct. 15, 2011 (Oct. 15, 2011), pp. 10905-10908.
Naphatsawan B00nsath0rn et al: monoclonal antibody derived from a vaccinated volunteer recognizes heterosubtypically a novel epitope on the hemagglutinin globular head of HI and H9 influenza A viruses, Biochemical and Biophysical Research Communications, vol. 452, No. 3, Sep. 6, 2014 (Sep. 6, 2014), pp. 865-870.
E. Benjamin et al: Neutralizing Human Monoclonal Antibody Directed against a Novel Conserved Epitope on the Influenza Virus H3 Hemagglutinin Globular Head, Journal of Virology vol. 88, No. 12, Jun. 1, 2014 (Jun. 1, 2014), pp. 6743-6750.
Soema Peter C et al: "Current and next generation influenza vaccines: Formulation and production strategies", European Journal of Pharmaceutics and Biopharmaceutics, Elsevier Science Publishers B.V., Amsterdam, NL, vol. 94, Jun. 3, 2015 (Jun. 3, 2015), pp. 251-263.
Belongia et al., 2009. Effectiveness of Inactivated Influenza Vaccines Varied Substantially with Antigenic Match from the 2004-2005 Season to the 2006-2007 Season Linked references are available on JSTOR for this article : Effectiveness of Inactivated Influenza Vaccines Varied. The Journal of Infectious Disease, 199(2), pp. 159-167.
Carnell et al., (2015) Pseudotype-based neutralization assays for influenza: a systematic analysis. Front lmmunol. 29;6:161. doi: 10.3389/fimmu.2015.00161.
Carter et al., 2016 "Design and Characterisation of a COBRA HA vaccine for H1N1 influenza viruses".
Carter et al., (2013) Sequential seasonal H1N1 influenza virus infections protect ferrets against novel 2009 H1N1 influenza virus. J Virol. ;87(3):1400-10.
Huang et al 2015 Focused antibody response.
Li et al., 2013. Immune history shapes specificity of pandemic H1N1 influenza antibody responses. 210(8), pp. 1493-1500.
Manicassamy et al., 2010. Protection of mice against lethal challenge with 2009 H1N1 influenza A virus by 1918-like and classical swine H1N1 based vaccines. PLoS Pathogens, 6(1).
Matsuzaki et al., 2014. Epitope Mapping of the Hemagglutinin Molecule of A/(H1N1 ) pdm09 Influenza Virus by Using Monoclonal Antibody Escape Mutants. Journal of Virology, 88(21), pp. 12364-12373.
Mertz, D., Hyong, T & Johnstone, J., 2013. Populations at risk for severe or complicated influenza illness : systematic review and meta-analysis. British Medical Journal, 5061(August), pp. 1-15.
Jegerlehner et al., PLoS ONE, vol. 8(11), 2013, 'Bacterially produced recombinant influenza vaccines based on virus-like particles' article 78947.
Recker et al., 2007. The generation of influenza outbreaks by a network of host immune responses against a limited set of antigenic types. PNAS 104:7711.
Sun et al., Journal of Virology, Sep. 2010, vol. 84, No. 17, p. 8683-8690.
Treanor, J.J. et al., 2012. Effectiveness of Seasonal Influenza Vaccines in the United States During a Season With Circulation of All Three Vaccine Strains., pp. 1-9.
Whittle et al. 2011 "Broadly neutralizing human antibody that recognizes the receptor-binding pocket of influenza virus hemagglutinin".
Wikramaratna, P.S. et al., 2013. The antigenic evolution of influenza: drift or thrift? Philosophical transactions of the Royal Society of London. Series B, Biological sciences, 368(1614), p.20120200.

* cited by examiner

Figure 9B

| | 83 | 85 | 146 | 147 | 148 | 149 | 151 | 154 | 155 | 156 | 157 | 158 | 159 | 163 | |
|---|---|---|---|---|---|---|---|---|---|---|---|---|---|---|---|
| 2009 consensus | E | E | N | K | G | V | A | P | H | A | G | A | K | K | |
| 2010 consensus | E | E | N | K | G | V | A | P | H | A | G | A | K | K | |
| 2011 consensus | E | E | N | K | G | V | A | P | H | A | G | A | K | K | |
| 2012 consensus | E | E | N | K | G | V | A | P | H | A | G | A | K | K | |
| 2013 consensus | E | E | N | K | G | V | A | P | H | A | G | A | K | K | |
| 2014 consensus | E | E | N | K | G | V | A | P | H | A | G | A | K | K | |
| 2015 consensus | E | E | N | K | G | V | A | P | H | A | G | A | K | K | |
| 1918 consensus | E | D | T | K | G | V | A | S | H | A | G | A | S | R | **Group 1** |
| 1942 consensus | E | E | T | K | G | V | A | S | H | A | G | K | C | R | (Blue) |
| 1935 consensus | E | D | T | K | G | V | A | S | H | A | G | K | S | R | |
| 1994 consensus | E | E | N | R | G | V | A | P | H | A | G | A | N | R | |
| 1950 consensus | E | E | I/T | R | G | V | A | S | H | A | G | K | S | K | |
| 1947 consensus | E | E | T | R | G | V | A | S | H | A | G | K | S | K | |
| 1945 consensus | E | E | T | R | G | V | A | S | H | A | G | K | S | R | |
| 1945 consensus | E | E | T | R | G | V | A | S | H | A | G | K | S | R | |
| 1943 consensus | E | E | A | R | G | V | A | S | H | A | G | K | S | R | |

| | | | | | | | | | | | | | | | |
|---|---|---|---|---|---|---|---|---|---|---|---|---|---|---|---|
| 1946 consensus | E | E | D/T/N | I | G | V | A | S | H | A | G | K | S | K | |
| 1940 consensus | E | E | N | I | G | V | A | S | H | A | G | K | S | K | **Group 2** |
| 1936 consensus | E | D | N | I | G | V | A | S | H | A | G | K | S | R | (Hazel) |

Figure 9C

Group 3 (Green)

| | | | | | | | | | | | | | | |
|---|---|---|---|---|---|---|---|---|---|---|---|---|---|---|
| 1951 consensus | E | E | T | R | G | V | A | S | H | A | K | K | S | K |
| 1954 consensus | E | E | T | R | G | V | A | S | H | A | K | K | S | K |
| 1953 consensus | E | E | T | R | G | V | A | S | H | A | R | K | S | K |
| 1948 consensus | E | E | T | R | G | V | A | S | H | K | G | K | S | R |
| 1949 consensus | E | E | T | R | G | V | A | S | H | K | G | K | S | R |
| 1977 consensus | E | E | T | R | G | V | A | S | H | K | G | K | S | R |
| 1978 consensus | E | E | T | R | G | V | A | S | H | K | G | K | S | R |
| 1979 consensus | E | E | T | R | G | V | A | S | H | K | G | K | S | R |
| 1980 consensus | E | E | T | R | G | V | A | S | H | K | G | K | S | R |
| 1982 consensus | E | E | T | R | G | V | A | S | H | K | G | K | S | R |
| 1985 consensus | E | E | T | R | G | V | A | S | H | K | G | K | S | R |
| 1981 consensus | E | E | T | R | G | V | A | S | H | K | G | K | C | R |
| 1933 consensus | E | D | L | K | G | V | A | S | H | G/R | G | K | S | R |
| 1983 consensus | E | E | T | K | G | V | A | S | H | K | G | K | S | R |
| 1984 consensus | E | E | T | K | G | V | A | S | H | K | G | K | S | R |
| 1986 consensus | E | E | T | K | G | V | A | S | H | K | G | K | S | R |
| 1987 consensus | E | E | T | K | G | V | A | S | H | K | G | K | S | R |

Figure 9D

Group 4 (Orange)

| | 83 | 85 | 146 | 147 | 148 | 149 | 151 | 154 | 155 | 156 | 157 | 158 | 159 | 163 |
|---|---|---|---|---|---|---|---|---|---|---|---|---|---|---|
| 1989 consensus | E | E | T | K | G | V | A | S | H | N | G | K | S | R |
| 1992 consensus | E | E | T | K | G | V | A | S | H | N | G | K | S | R |
| 1993 consensus | E | E | T | K | G | V | A | S | H | N | G | K | S | R |
| 1991 consensus | K | E | T | K | G | V | A | S | H | N | G | K | S | R |
| 1995 consensus | E | E | T | K | G | V | A | S | H | N | G | K | S | K |
| 1996 consensus | E | E | T | K | G | V | A | S | H | N | G | K | S | K |

Group 5 (Red)

| | 83 | 85 | 146 | 147 | 148 | 149 | 151 | 154 | 155 | 156 | 157 | 158 | 159 | 163 |
|---|---|---|---|---|---|---|---|---|---|---|---|---|---|---|
| 1998 consensus | E | E | T | - | G | V | A | S | H | N | G | K | S | R |
| 1999 consensus | E | E | T | - | G | V | A | S | H | N | G | K | S | R |
| 2000 consensus | E | E | T | - | G | V | A | S | H | N | G | K | S | R |
| 2001 consensus | E | E | T | - | G | V | A | S | H | N | G | K | S | R |
| 2002 consensus | E | E | T | - | G | V | A | S | H | N | G | K | S | R |
| 2003 consensus | E | E | T | - | G | V | A | S | H | N | G | K | S | R |
| 2004 consensus | E | E | T | - | G | V | A | S | H | N | G | K | S | R |
| 2005 consensus | E | E | T | - | G | V | A | S | H | N | G | K | S | R |
| 2006 consensus | E | E | T | - | G | V | A | S | H | N | G | K | S | K |
| 2007 consensus | E | E | T | - | G | V | A | S | H | N | G | E | S | R |
| 2008 consensus | E | E | T | - | G | V | A | S | H | N | G | E | S | R |
| 1934 consensus | E | D | N | - | G | V | A | S | H | E | G | K | S | R |
| 1957 consensus | E | E | R | - | G | V | A | P | H | A | R | K | S | K |

IMMUNOGENIC COMPOSITION

CROSS-REFERENCE TO RELATED APPLICATIONS

This application is the National Stage of International Application No. PCT/GB2017/052510, filed Aug. 25, 2017, which claims the priority to GB 1614485.9, filed Aug. 25, 2016, which are entirely incorporated herein by reference.

STATEMENT

The work leading to this invention has received funding from the European Research Council under the European Union's Seventh Framework Programme (FP7/2007-2013)/ ERC grant agreement n° 268904.

The present invention relates to an immunogenic composition comprising two or more polypeptides. The invention also provides nucleic acid molecules and vectors encoding the polypeptides, and methods of using the compositions, nucleic acid molecules and vectors for the prevention or treatment of influenza.

Seasonal influenza is a serious public health problem that causes severe illness and death. Worldwide, seasonal influenza is estimated to cause 3 to 5 million cases of severe illness and 250,000 to 500,000 deaths (Lozano et al. 2012). The demographics highest at risk of complications are children younger than 2 years of age, adults aged over 65, pregnant women, and people of any age with certain medical conditions such as diabetes or weakened immune systems (Mertz et al. 2013). It is estimated that a large proportion of child deaths in developing countries are associated with influenza. Seasonal influenza also causes high levels of workforce absenteeism and productivity losses.

Influenza pandemics occur sporadically when a distinct influenza strain from an animal reservoir begins to circulate widely in the human population. The most recent influenza pandemic occurred in 2009, which caused an increase in severe influenza illness and hospitalisation in individuals aged under 35 (Presonis et al., 2011; Manicassamy et al., 2010). The 1918 influenza pandemic was the most serious pandemic in recorded history, causing 50-100 million deaths. The emergence of a new pandemic influenza strain remains of concern.

The most effective way to prevent illness from influenza infection is vaccination. Currently, vaccination against influenza involves a trivalent or quatrivalent vaccine consisting of the most recent circulating strains of the H1N1 and H3N2 subtypes of influenza A and also includes one or two of influenza B strains (WHO, 2016). Due to the rapid antigenic evolution of influenza, the vaccine has to be constantly updated, and often due to time constrains, the wrong vaccine strains for the coming influenza season are chosen. For these reasons, the convention trivalent vaccine is estimated to have 10-60% efficacy and immunisation of at risk groups takes place annually (Treonor et al. 2012; Belongia et al. 2009).

Consequently, there are clear societal and economic benefits for improving the current influenza vaccines. This has been recognised by pharmaceutical companies, such as GSK and Pfizer, who are developing their own new influenza vaccines. Such approaches typically target epitopes that are under weak immune selection and therefore 'immunorecessive'.

The influenza virus is currently conceptualised as containing (i) highly immunogenic (and protective) epitopes of high variability, as well as (ii) invariant epitopes of low immunogenicity. Together, these form the backbone of the theory of "antigenic drift" whereby the virus population slowly and incrementally acquires changes in the highly variable epitope regions requiring vaccines directed against these sites to be continuously updated, with the only other alternative being seen as the artificial boosting of immunity to invariant epitopes of low natural efficacy.

The inventors propose, by contrast, that the influenza virus also contains highly immunogenic epitopes of low variability and that universal vaccines may be constructed by identifying these protective epitopes. This idea is underpinned by an alternative theory of influenza evolution known as "antigenic thrift" in which viral dynamics are driven by pre-existing immunity to shared epitopes, but the existence of such epitopes has remained in doubt and their use in vaccination has never previously been mooted.

Using a combination of bioinformatics, structural and serological analyses, one epitope of limited variability that is under strong immune selection in the major influenza antigen, haemagglutinin (HA), has now been identified and characterised.

HA is the major surface antigen in influenza viruses. It binds sialic acid and initiates membrane fusion, leading to endocytosis. It is a trimeric protein typically 565/566 amino acids in length. Each monomer consists of a head domain and a stem domain.

The epitope which has now been identified is under strong immune selection and is therefore 'immunodominant'. This has enabled the design of a new 'universal' influenza vaccine that protects against the majority of H1N1 influenza strains by targeting this epitope of limited variability.

Consequently, the vaccine of the current invention has a number of advantages over the conventional trivalent vaccine and other influenza vaccines in development.

These advantages include:

(i) infection with circulating influenza strains will reinforce vaccine protection instead of potentially detracting from it;

(ii) the vaccine should be more immunogenic than other 'universal' vaccines in development, leading to lower thresholds of protection and greater longevity of protection;

(iii) it should only need to be administered between one and three times (i.e. a prime and a boost, or a prime and two boosts); and (iv) the theoretical and experimental framework from which the vaccine has been derived suggests that H1N1 influenza is not likely to escape the protection conferred by the proposed vaccine.

It is therefore an object of the invention to provide an influenza vaccine composition which is capable of conferring protection against one or more influenza A subtypes, preferably against the H1N1 subtype.

In one embodiment, therefore, the invention provides an immunogenic composition comprising two or more polypeptides, wherein each polypeptide independently comprises a first region of contiguous amino acids, wherein:

(a) the amino acid sequence of the first region has at least 80% sequence identity to an influenza A haemagglutinin head domain; and (b) the first region has one or more amino acid substitutions at positions which correspond to the following positions in SEQ ID NO: 9:

position 83 is E
position 85 is a negatively charged amino acid
position 146 is T, N, I or A
position 147 is a positively charged amino acid, I or is absent
position 148 is G position 149 is V
position 151 is A
position 154 is S or P
position 155 is H
position 156 is a positively charged amino acid or A or G or N or E
position 157 is a positively charged amino acid or A or G
position 158 is a positively charged amino acid or A or S or N or C or E
position 159 is K or A or S or N or C
position 163 is a positively charged amino acid, wherein the amino acid sequences of the two or more polypeptides are different, and wherein the composition is capable of inducing antibodies in a subject against an influenza A virus, optionally together with one or more pharmaceutically-acceptable carriers, adjuvants, excipients or diluents.

The invention also provides a polypeptide, wherein the amino acid sequence of the polypeptide comprises a first region, wherein:

(a) the amino acid sequence of the first region has at least 80% sequence identity to an influenza A subtype H1, H2, H3, H4, H5, H6, H7, H8, H9, H10, H11, H12, H13, H14, H15, H16, H17 or H18 haemagglutinin head domain, preferably an influenza A subtype H1, H5, H6, H9 or H11 haemagglutinin head domain;

and (b) the first region has one or more amino acid substitutions at positions which correspond to the following positions in SEQ ID NO: 9:
position 83 is E
position 85 is a negatively charged amino acid
position 146 is T, N, I or A
position 147 is a positively charged amino acid, I or is absent
position 148 is G
position 149 is V
position 151 is A
position 154 is S or P
position 155 is H
position 156 is a positively charged amino acid or A or G or N or E
position 157 is a positively charged amino acid or A or G
position 158 is a positively charged amino acid or A or S or N or C or E
position 159 is K or A or S or N or C
position 163 is a positively charged amino acid.

The invention also provides a composition (preferably an immunogenic composition wherein the composition is capable of inducing antibodies in a subject against an influenza A virus) comprising such a polypeptide, optionally together with one or more pharmaceutically-acceptable carriers, adjuvants, excipients or diluents.

The invention also provides nucleic acids molecules (preferably DNA molecules) coding for such polypeptides, preferably wherein the DNA molecule is a vector or plasmid.

In one preferred embodiment, (b) the first region has one or more amino acid substitutions at positions which correspond to the following positions in SEQ ID NO: 9:
position 83 is E
position 85 is E or D
position 146 is T or N
position 147 is R or K or I or is absent
position 148 is G
position 149 is V
position 151 is A
position 154 is S or P
position 155 is H
position 156 is A or G or K or N or E
position 157 is A or G
position 158 is A or K
position 159 is A, K, C, N or S
position 163 is K or R.

In another preferred embodiment, (b) the first region has one or more amino acid substitutions at positions which correspond to the following positions in SEQ ID NO: 9:
position 83 is E
position 85 is a negatively charged amino acid
position 146 is T, N, I or A
position 147 is a positively charged amino acid,
position 148 is G
position 149 is V
position 151 is A
position 154 is S or P
position 155 is H
position 156 is A
position 157 is G
position 158 is K or A or S or N or C
position 159 is K or A or S or N or C
position 163 is a positively charged amino acid.

In another preferred embodiment, (b) the first region has one or more amino acid substitutions at positions which correspond to the following positions in SEQ ID NO: 9:
position 83 is E
position 85 is E
position 146 is N
position 147 is R
position 148 is G
position 149 is V
position 151 is A
position 154 is P
position 155 is H
position 156 is A
position 157 is G
position 158 is A
position 159 is K
position 163 is K Preferably, the first region of one polypeptide comprises or consists of the amino acid sequence given in SEQ ID NO: 13.

In another preferred embodiment, (b) the first region has one or more amino acid substitutions at positions which correspond to the following positions in SEQ ID NO: 9:
position 83 is E
position 85 is a negatively charged amino acid
position 146 is N
position 147 is I
position 148 is G
position 149 is V
position 151 is A
position 154 is S
position 155 is H
position 156 is K or A
position 157 is G
position 158 is A or K
position 159 is K or S
position 163 is a positively charged amino acid.

In another preferred embodiment, (b) the first region has one or more amino acid substitutions at positions which correspond to the following positions in SEQ ID NO: 9:
position 83 is E
position 85 is E position 146 is N
position 147 is I
position 148 is G
position 149 is V
position 151 is A
position 154 is S
position 155 is H
position 156 is A
position 157 is G
position 158 is K
position 159 is S
position 163 is K Preferably, the first region of one polypeptide comprises or consists of the amino acid sequence given in SEQ ID NO: 14.

In another preferred embodiment, (b) the first region has one or more amino acid substitutions at positions which correspond to the following positions in SEQ ID NO: 9:

position 83 is E
position 85 is a negatively charged amino acid
position 146 is T
position 147 is a positively charged amino acid
position 148 is G
position 149 is V
position 151 is A
position 154 is S
position 155 is H
position 156 is a positively charged amino acid or A or G
position 157 is a positively charged amino acid or A or G
position 158 is K
position 159 is S or C
position 163 is a positively charged amino acid.

In another preferred embodiment, (b) the first region has one or more amino acid substitutions at positions which correspond to the following positions in SEQ ID NO: 9:

position 83 is E
position 85 is E
position 146 is T
position 147 is R
position 148 is G
position 149 is V
position 151 is A
position 154 is S
position 155 is H
position 156 is K
position 157 is G
position 158 is K
position 159 is S
position 163 is K.

Preferably, the first region of one polypeptide comprises or consists of the amino acid sequence given in SEQ ID NO: 15.

In another preferred embodiment, (b) the first region has one or more amino acid substitutions at positions which correspond to the following positions in SEQ ID NO: 9:

position 83 is E
position 85 is a negatively charged amino acid
position 146 is T
position 147 is a positively charged amino acid
position 148 is G
position 149 is V
position 151 is A
position 154 is S
position 155 is H
position 156 is N
position 157 is G
position 158 is a positively charged amino acid
position 159 is S
position 163 is a positively charged amino acid.

In another preferred embodiment, (b) the first region has one or more amino acid substitutions at positions which correspond to the following positions in SEQ ID NO: 9:

position 83 is E
position 85 is E
position 146 is T
position 147 is K
position 148 is G
position 149 is V
position 151 is A
position 154 is S
position 155 is H
position 156 is N
position 157 is G
position 158 is K
position 159 is S
position 163 is R.

Preferably, the first region of one polypeptide comprises or consists of the amino acid sequence given in SEQ ID NO: 16.

In another preferred embodiment, (b) the first region has one or more amino acid substitutions at positions which correspond to the following positions in SEQ ID NO: 9:

position 83 is E
position 85 is a negatively charged amino acid
position 146 is Tor N
position 147 is absent
position 148 is G
position 149 is V
position 151 is A
position 154 is S or P
position 155 is H
position 156 is N or E
position 157 is G
position 158 is K or E
position 159 is S
position 163 is a positively charged amino acid.

In another preferred embodiment, (b) the first region has one or more amino acid substitutions at positions which correspond to the following positions in SEQ ID NO: 9:

position 83 is E
position 85 is E
position 146 is T
position 147 is absent
position 148 is G
position 149 is V
position 151 is A
position 154 is S
position 155 is H
position 156 is N
position 157 is G
position 158 is K
position 159 is S
position 163 is R.

Preferably, the first region of one polypeptide comprises or consists of the amino acid sequence given in SEQ ID NO: 17.

In one embodiment, the invention relates to an immunogenic composition.

As used herein, the term "immunogenic" is intended to refer to the ability to elicit a specific immune response against an influenza A subtype. This response may, for example, be when a composition of the invention is administered at an appropriate dose and in an appropriate formulation which may include/require a suitable adjuvant. A booster comprising a dose similar or less than the original dose may be required to obtain the required immunogenic response.

In particular, the immunogenic composition of the invention is capable of inducing antibodies (preferably neutralising antibodies) in a subject against influenza A virus.

Preferably, the immunogenic composition of the invention is capable of providing protection in a subject against influenza A virus.

More preferably, the immunogenic composition of the invention is capable of inducing antibodies (preferably neutralising antibodies) in a subject against the H1N1 influenza A subtype.

The capability of a composition of the invention to induce neutralising antibodies in a subject (e.g. a human subject) may be tested by purifying sera from the blood of subjects to whom the composition has been administered.

Antibodies may be measured using ELISA or a pseudotype micro-neutralisation (pMN) assay. ELISA is the most sensitive of these two assays; it quantifies all antibodies. In contrast, the pMN is less sensitive, but it quantifies neutralising antibodies.

As used herein, the reference to “influenza” relates to influenza virus, preferably influenza A virus, more preferably influenza A virus H1 subtypes, and most preferably influenza A virus H1N1 subtypes.

The immunogenic composition comprises one, two or more polypeptides. The amino acid sequences of these two or more polypeptides are preferably different.

The composition may, for example, comprise 2, 3, 4, 5, 6, 7, 8, 9 or 10 different polypeptides.

Preferably, the composition comprises 2, 3, 4 or 5 different polypeptides, more preferably 3 different polypeptides.

The sequences of the invention are derived from or based upon the head domain of influenza A haemagglutinin proteins.

The naturally-occurring haemagglutinin protein is a homo-trimer of three polypeptides.

In a preferred composition of the invention, the composition comprises three polypeptides as defined herein which form a homotrimer. The composition may comprise more than one (e.g. 2, 3, 4, or 5) different homotrimers of the polypeptides defined herein.

In another preferred embodiment, three polypeptides of the invention form a hetero-trimer in the composition. The composition may comprise more than one (e.g. 2, 3, 4, or 5) different heterotrimers of the polypeptides defined herein.

Each polypeptide independently comprises a first region of contiguous amino acids. This region is a contiguous stretch of amino acids which are covalently joined.

In one embodiment, the amino acid sequence of the first region has at least 80% sequence identity to an influenza A haemagglutinin (HA) head domain.

The intention is that this first region adopts the conformation of an influenza A haemagglutinin head domain.

The haemagglutinin head domain may, for example, be from any influenza A subtype, e.g. H1, H2, H3, H4, H5, H6, H7, H8, H9, H10, H11, H12, H13, H14, H15, H16, H17 or H18.

Preferably, the haemagglutinin head domain is from an influenza A H1, H5, H6, H9 or H11 subtype.

In one embodiment, haemagglutinin head domain is from an influenza A H1 subtype.

In one embodiment, haemagglutinin head domain is from an influenza A H5 subtype.

In one embodiment, haemagglutinin head domain is from an influenza A H6 subtype.

In one embodiment, haemagglutinin head domain is from an influenza A H9 subtype.

In one embodiment, haemagglutinin head domain is from an influenza A H11 subtype.

Preferably, the influenza A N subtype is N1.

Consensus amino acid sequences of the H1, H5, H6 and H11 haemagglutinin polypeptides are given herein as SEQ ID NOs: 9-12, respectively. A consensus amino acid sequence of the H9 haemagglutinin polypeptide is given herein as SEQ ID NO: 23. The H9 sequence may be used herein in place of the H1, H5, H6 or H9 embodiments disclosed herein, mutatis mutandis.

The amino acid sequence number used herein is based on the numbering given to the influenza A H1 haemagglutinin head domain as given in SEQ ID NO: 9.

It should be noted that there are three ways of numbering the influenza A H1 haemagglutinin polypeptide and throughout the current specification the linear numbering is used where Met=1.

The HA polypeptide comprises two regions: the HA1 region and the HA2 region. These regions are separated by a potential cleavage site.

The H1 cleavage site consensus sequence is PSIQSR/GLF (SEQ ID NO: 24); the H5 cleavage site consensus sequence is PQRKKR/GLF (SEQ ID NO: 25); the H6 cleavage site consensus sequence is PQIETR/GLF (SEQ ID NO: 26); the H9 cleavage consensus sequence is PSRSSR/GLF (SEQ ID NO: 27); and the H11 cleavage site consensus sequence is PAIATR/GLF (SEQ ID NO: 28).

Cleavage of HA0 into HA1 and HA2 occurs between R/GLF and is performed by a protease. The cleavage sites stated above are all described as monobasic. In some H5 viruses, a polybasic cleavage site is present, and this differs from the monobasic sites by having has multiple arginine residues (R’s) and/or lysine residues (K’s) in the critical position basic position.

Further details of the cleavage sites may be found in Sun et al., Journal of Virology, September 2010, Vol. 84, No. 17, p. 8683-8690.

The HA1 region comprises 1-60 amino acids of the stalk, followed by the head domain, and then additional stalk amino acids. The HA2 region comprises only stalk amino acids.

The head domain of haemagglutinin is defined as being between two cysteines within the HA1 region. The first cysteine is generally at position 58, 59 or 60; the second cysteine is generally at position 290, 291 or 292.

In influenza A H1 haemagglutinins, these cysteines are at positions 59 and 291/292 due to the absence of an amino acid at position 147 in some H1 haemagglutinins.

For H6 haemagglutinins, the head domain corresponds to the sequence between positions 58 and 292.

However, for H5 and H11 haemagglutinins, the head domain corresponds to the region between positions 58 to 290, respectively.

For H9 haemagglutinins, the head domain corresponds to the region between positions 60 to 290.

Consensus amino acid sequences of the H1, H5, H6 and H11 haemagglutinin head domains are given herein as SEQ ID NOs: 1-4, respectively.

In some embodiments, the amino acid sequence of the first region has at least 80%, 85%, 90% or 95% sequence identity to SEQ ID NO: 1.

In some embodiments, the amino acid sequence of the first region has at least 80%, 85%, 90% or 95% sequence identity to SEQ ID NO: 2.

In some embodiments, the amino acid sequence of the first region has at least 80%, 85%, 90% or 95% sequence identity to SEQ ID NO: 3.

In some embodiments, the amino acid sequence of the first region has at least 80%, 85%, 90% or 95% sequence identity SEQ ID NO: 4.

In some embodiments, the amino acid sequence of the first region has at least 65%, 70%, 75%, 80%, 85%, 90%, 95%, 98%, 99% or 100% sequence identity to an influenza A haemagglutinin head domain at positions other than those that correspond to positions 83, 85, 146-149, 151, 154-159 and 163 of SEQ ID NO: 9.

In some embodiments, the amino acid sequence of the first region has at least 65%, 70%, 75%, 80%, 85%, 90%, 95%, 98%, 99% or 100% sequence identity to an influenza A H1 haemagglutinin head domain (preferably of SEQ ID NO: 1) at positions other than those that correspond to positions 83, 85, 146-149, 151, 154-159 and 163 of SEQ ID NO: 9.

In some embodiments, the amino acid sequence of the first region has at least 65%, 70%, 75%, 80%, 85%, 90%, 95%, 98%, 99% or 100% sequence identity to an influenza A H6 haemagglutinin head domain (preferably of SEQ ID NO: 2) at positions other than those that correspond to positions 83, 85, 146-149, 151, 154-159 and 163 of SEQ ID NO: 9.

In some embodiments, the amino acid sequence of the first region has at least 65%, 70%, 75%, 80%, 85%, 90%, 95%, 98%, 99% or 100% sequence identity to an influenza A H5 haemagglutinin head domain (preferably of SEQ ID NO: 3) at positions other than those that correspond to positions 83, 85, 146-149, 151, 154-159 and 163 of SEQ ID NO: 9.

In some embodiments, the amino acid sequence of the first region has at least 65%, 70%, 75%, 80%, 85%, 90%, 95%, 98%, 99% or 100% sequence identity to an influenza A H11 haemagglutinin head domain (preferably of SEQ ID NO: 4) at positions other than those that correspond to positions 83, 85, 146-149, 151, 154-159 and 163 of SEQ ID NO: 9.

In some embodiments, each polypeptide independently additionally comprises one or more amino acids which are contiguously joined to the first region at the N- and/or C-termini.

The additional N-terminal amino acids are preferably a stretch of contiguous amino acids which are derived from a haemagglutinin N-terminal stalk region, preferably from a haemagglutinin N-terminal stalk region of an influenza A H subtype, most preferably a H1, H5, H6, H9 or H11 subtype.

Preferably, 58-60 amino acids of a haemagglutinin N-terminal stalk region of an influenza A subtype are contiguously joined to the N-terminal of the first region in one or more of the polypeptides.

In some embodiments, the amino acid sequence of this stalk region has at least 65%, 70%, 75%, 80%, 85%, 90%, 95% or 100% sequence identity to:

(i) amino acids 1-59 of SEQ ID NO: 9, (ii) amino acids 1-58 of SEQ ID NO: 10, (iii) amino acids 1-58 of SEQ ID NO: 11, or (iv) amino acids 1-58 of SEQ ID NO: 12.

The additional C-terminal amino acids, if present, are preferably a stretch of contiguous amino acids (e.g. 1-300, 1-200, 1-100, 1-50 or 1-10 amino acids) which are derived from the haemagglutinin C-terminal stalk region of an influenza A subtype, preferably H1, H5 H6, H9 or H11.

Preferably, the stretch of contiguous amino acids is derived from the haemagglutinin stalk region of the same influenza A subtype from which the head region is derived.

In some embodiments, the polypeptides do not comprise an influenza A subtype HA2 region.

In some embodiments, the polypeptides do not comprise the HA2 region of SEQ ID NOs: 9-12.

In some preferred embodiments, one or more or all of the one, two or more polypeptides independently comprise an influenza A HA1 domain comprising a first region as defined herein, most preferably an influenza A H1, H5, H6 or H11 subtype HA1 domain comprising a first region as defined herein.

Preferably, the polypeptides are independently less than 600, more preferably less than 400 and most preferably less than 300 amino acids in length.

Preferably, the polypeptides are independently 250-350, more preferably 280-300 amino acids in length, and most preferably 290-292 amino acids in length.

The first region of the polypeptide has one or more amino acid substitutions at specified positions which correspond to positions in SEQ ID NO: 1.

For example, the first region of the polypeptide may have 1, 2, 3, 4, 5, 6, 7, 8, 9, 10, 11, 12, 13 or 14 of the specified amino acid substitutions.

Preferably, the first region of the polypeptide has all of the specified 14 amino acid substitutions.

As used herein, the term "positively charged amino acid" includes lysine, arginine and histidine. As used herein, the term "negatively charged amino acid" includes aspartic acid and glutamic acid.

In some preferred embodiments, the amino acid sequences of the polypeptides independently comprise or consist of an amino acid sequence of SEQ ID NOs: 13-17.

The polypeptides of the invention may be produced using recombinant methodology. For example, such techniques are described in "Molecular Cloning: A Laboratory Manual" (Fourth Edition) Michael R. Green and Joseph Sambrook.

Alternatively, the nucleotide sequence encoding the polypeptides may be produced by chemical synthesis. Such a nucleotide sequence may then be ligated into an appropriate vector for host cell transformation or transfection. The polypeptides may then be expressed in such host cells.

For modifications of existing HA genes, CRISPR-based techniques may also be used, such as those described in "CRISPR-Cas: A Laboratory Manual" (2016), edited by Jennifer Doudna (University of California, Berkeley) and Prashant Mali (University of California, San Diego). TALENs-based techniques may also be used.

Alternatively, the polypeptides of the invention may be synthesised using standard chemical peptide synthesis techniques. Solid phase synthesis of peptides in which the C-terminal amino acid of the sequence is attached to an insoluble support followed by sequential addition of the remaining amino acids may, for example, be used.

In a further embodiment, the invention provides a nucleic acid molecule which codes for one or more polypeptides of the invention. Preferably, the nucleic acid molecule encodes one, two or more, preferably 1, 2, 3, 4, 5, 6, 7, 8, 9 or 10 of the polypeptides of the invention.

Preferred nucleotide sequences include those comprising SEQ ID NOs: 18-22, and nucleotide sequences having at least 80%, 85%, 90% or 95% sequence identity thereto, encoding polypeptides which are capable of inducing antibodies in a subject against an influenza A virus.

Also preferred are nucleic acid molecules encoding polypeptide of SEQ ID NOs: 13-17.

As used herein, the terms "nucleic acid sequence", "nucleic acid molecule" and "polynucleotide" are used interchangeably and do not imply any length restriction. These include DNA (including cDNA) and RNA sequences.

The nucleic acid molecules of the present invention include isolated nucleic acid molecules that have been removed from their naturally-occurring environment, recombinant or cloned DNA isolates, and chemically-synthesized analogues or analogues which have been synthesized biologically by heterologous systems.

The nucleic acid molecules of the present invention may be prepared by any means known in the art. For example, large amounts of the polynucleotides may be produced by replication in a suitable host cell. The natural or synthetic DNA fragments coding for a desired fragment may be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The nucleic acid molecules of the present invention may also be produced by chemical synthesis, e.g. by the phosphoramidite method or the tri-ester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

The original (e.g. wild-type) codons in a nucleic acid molecule may be optimised for expression in a desired cell line, for example, using an online tool.

In one embodiment of the invention, therefore, the nucleic acid molecule is codon-optimized for expression in a host cell, preferably a human cell.

As used herein, the term "product of the invention" refers to the polypeptides of the invention, nucleic acids of the invention, vectors of the invention, particles of the invention and compositions of the invention, inter alia.

The invention also provides a vector or plasmid comprising a nucleic acid molecule of the invention. Preferably, the vector is an expression vector.

The vector and/or plasmid may comprise one or more regulatory sequences which are operably linked to the sequence which encodes the polypeptide, e.g. one or more enhancer, promoter and/or transcriptional terminator sequences.

In a particularly preferred embodiment, there is provided an immunogenic composition comprising one, two or more vectors encoding polypeptides of SEQ ID NOs: 13-17, optionally together with one or more pharmaceutically-acceptable carriers, adjuvants, excipients or diluents, as a combined preparation in a form suitable for simultaneous, separate or sequential use for treating or preventing influenza A infection.

Preferably, a prime is administered to the subject with vector(s) encoding SEQ ID NOs: 14 and 15; then a first boost using vector(s) encoding SEQ ID NOs: 13 and 16; and then a final boost using a vector encoding SEQ ID NO: 17.

In some embodiments, the vector is viral vector, e.g. a poxvirus vector.

In other embodiments, the vector is an adenoviral vector or a Modified Vaccinia Ankara (MVA) viral vector.

Preferably, the vector is a non-replicating vector.

Non-replicating poxviruses and adenoviruses represent groups of viruses which may be used as vectors for the delivery of genetic material into a target cell. Viral vectors serve as antigen delivery vehicles and also have the power to activate the innate immune system through binding cell surface molecules that recognise viral elements. A recombinant viral vector can be produced that carries nucleic acid encoding a given antigen. The viral vector can then be used to deliver the nucleic acid to a target cell, where the encoded antigen is produced by the target cell's own molecular machinery. As "non-self", the produced antigen generates an immune response in the target subject.

Without wishing to be bound by any one particular theory, the inventors believe that antigen delivery using the vectors of the invention stimulates, amongst other responses, a T-cell response in the subject. Thus, the inventors believe that one way in which the present invention provides for protection against influenza infection is by stimulating T-cell responses and the cell-mediated immunity system. In addition, humoral (antibody) based protection can also be achieved.

The vector of the invention may be a non-replicating poxvirus vector. As used herein, a non-replicating (or replication-deficient) viral vector is a viral vector which lacks the ability to productively replicate following infection of a target cell. Thus, a non-replicating viral vector cannot produce copies of itself following infection of a target cell. Non-replicating viral vectors may therefore advantageously have an improved safety profile as compared to replication-competent viral vectors.

In one embodiment, the non-replicating poxvirus vector is selected from a Modified Vaccinia virus Ankara (MVA) vector, a NYVAC vaccinia virus vector, a canarypox (ALVAC) vector, and a fowlpox (FPV) vector. MVA and NYVAC are both attenuated derivatives of vaccinia virus. Compared to vaccinia virus, MVA lacks approximately 26 of the approximately 200 open reading frames.

In one embodiment, the non-replicating poxvirus vector is an MVA vector.

The vector of the invention may be an adenovirus vector. In one embodiment, the adenovirus vector is a non-replicating adenovirus vector (wherein non-replicating is defined as above). Adenoviruses can be rendered non-replicating by deletion of the EI or both the EI and E3 gene regions. Alternatively, an adenovirus may be rendered non-replicating by alteration of the EI or of the Ea and E3 gene regions such that said gene regions are rendered non-functional. For example, a non-replicating adenovirus may lack a functional EI region or may lack functional EI and E3 gene regions. In this way the adenoviruses are rendered replication-incompetent in most mammalian cell lines and do not replicate in immunised mammals. Most preferably, both EI and E3 gene region deletions are present in the adenovirus, thus allowing a greater size of transgene to be inserted. This is particularly important to allow larger antigens to be expressed, or when multiple antigens are to be expressed in a single vector, or when a large promoter sequence, such as the CMV promoter, is used. Deletion of the E3 as well as the EI region is particularly favoured for recombinant Ad5 vectors. Optionally, the E4 region can also be engineered.

In one embodiment, the adenovirus vector is selected from a human adenovirus vector, a simian adenovirus vector, a group B adenovirus vector, a group C adenovirus vector, a group E adenovirus vector, an adenovirus 6 vector, a PanAd3 vector, an adenovirus C3 vector, a ChAdY25 vector, an AdC68 vector, and an Ad5 vector.

The viral vector of the invention, as described above, can be used to deliver a single antigen to a target cell. Advantageously, the viral vector of the invention can also be used to deliver multiple (different) antigens to a target cell.

In one embodiment, the vector of the invention further comprises a nucleic acid sequence encoding an adjuvant (for example, a cholera toxin, an *E. coli* lethal toxin, or a flagellin).

The nucleic acid sequence encoding a vector (as described above) may be generated by the use of any technique for manipulating and generating recombinant nucleic acid known in the art. In one aspect, the invention provides a method of making a vector (as described above), comprising providing a nucleic acid, wherein the nucleic acid comprises a nucleic acid molecule encoding a vector of the invention; transfecting a host cell with the nucleic acid molecule; culturing the host cell under conditions suitable for the propagation of the vector; and obtaining the vector from the host cell.

As used herein, "transfecting" may mean any non-viral method of introducing nucleic acid molecules into a cell. The nucleic acid molecule may be any nucleic acid molecule suitable for transfecting a host cell. Thus, in one embodiment, the nucleic acid molecule is a plasmid. The host cell may be any cell in which a vector (i.e. a non-replicating poxvirus vector or an adenovirus vector, as described above) may be grown. As used herein, "culturing the host cell under conditions suitable for the propagation of the vector" means using any cell culture conditions and techniques known in the art which are suitable for the chosen host cell, and which enable the vector to be produced in the host cell. As used herein, "obtaining the vector", means using any technique known in the art that is suitable for separating the vector from the host cell. Thus, the host cells may be lysed to release the vector. The vector may subsequently be isolated and purified using any suitable method or methods known in the art.

The invention also provides a host cell comprising a nucleic acid molecule, vector or plasmid of the invention. Preferably, the host cell is a eukaryotic host cell. Examples of eukaryotic host cells include yeast and mammalian cells.

The host cell is preferably a cell in which a vector (e.g. a non-replicating poxvirus vector or an adenovirus vector, as described above) may be grown or propagated. The host cell may be selected from a 293 cell (also known as a HEK, or human embryonic kidney, cell), a CHO cell (Chinese Hamster Ovary), a CCL81.1 cell, a Vero cell, a HELA cell, a Per.C6 cell, a BHK cell (Baby Hamster Kidney), a primary CEF cell (Chicken Embryo Fibroblast), a duck embryo fibroblast cell, or a DF-1 cell.

In other embodiments, the host cell is a human cell (e.g. an isolated human cell).

In a further embodiment, there is provided a virus-like particle (VLP) comprising one, two or more (e.g. 3, 4, 5, 6, 7, 8, 9 or 10) polypeptides of the invention. The particle is preferably immunogenic.

Virus-like particles resemble viruses, but are non-infectious because they do not contain any viral genetic material. The particles may also be described as multimeric lipoprotein particles.

Once expressed in an appropriate system, these VLPs are able to assemble spontaneously into lipoprotein structures/particles composed of one or more monomers of said polypeptides.

The invention also provides a VLP wherein one, two or more (e.g. 3, 4, 5, 6, 7, 8, 9 or 10) polypeptides (preferably different polypeptides) of the invention are covalently attached to the VLP. For example, the polypeptides of the invention may be covalently attached to the VLP by using chemical cross-linkers, reactive unnatural amino acids or SpyTag/SpyCatcher reactions.

In a particularly preferred embodiment, there is provided an immunogenic composition comprising at least five different virus-like particles (VLPs), wherein each VLP independently comprises one or more homotrimers consisting of or comprised of polypeptides of SEQ ID NOs: 13-17, optionally together with one or more pharmaceutically-acceptable carriers, adjuvants, excipients or diluents, as a combined preparation in a form suitable for simultaneous, separate or sequential use for treating or preventing influenza A infection.

Preferably, a prime is administered to the subject with homotrimers of SEQ ID NOs: 14 and 15; the first boost using homotrimers of SEQ ID NOs: 13 and 16; and the final boost using a homotrimer of SEQ ID NO: 17.

The invention also provides a composition comprising one, two or more polypeptides of the invention, one or more nucleic acid molecules of the invention, one or more vectors of the invention or a VLP of the invention, optionally together with one or more pharmaceutically-acceptable carriers, excipients or diluents.

The composition is preferably an immunogenic composition.

Substances suitable for use as pharmaceutically-acceptable carriers are known in the art. Non-limiting examples of pharmaceutically-acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long term storage. Examples of buffering agents include, but are not limited to, sodium succinate (pH 6.5), and phosphate buffered saline (PBS; pH 7.4).

In addition to a pharmaceutically-acceptable carrier, the composition of the invention can be further combined with one or more of a salt, excipient, diluent, adjuvant, immunoregulatory agent and/or antimicrobial compound.

In one embodiment, the products of the invention may contain 5% to 95% of active ingredient (i.e. polypeptide, nucleic acid, vectors or VLPs), such as at least 10% or 25% of active ingredient, or at least 40% of active ingredient or at least 50%, 55%, 60%, 70% or 75% active ingredient.

The products of the invention may be administered in a manner compatible with the dosage formulation, and in such amount as will be prophylactically and/or therapeutically effective.

Administration of the products of the invention is generally by conventional routes, e.g. intravenous, subcutaneous, intraperitoneal, or mucosal routes. The administration may be by parenteral administration; for example, a subcutaneous or intramuscular injection.

Accordingly, the products of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules. The active ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the products of the invention may also contain minor amounts of auxiliary substances such as wetting or emulsifying agents, and/or pH buffering agents.

Additional formulations which are suitable for other modes of administration include oral formulations or formulations suitable for distribution as aerosols. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

It may be desired to direct the products of the present invention (as described above) to the respiratory system of a subject. Efficient transmission of a therapeutic/prophylactic composition or medicament to the site of infection in the lungs may be achieved by oral or intra-nasal administration.

Formulations for intranasal administration may be in the form of nasal droplets or a nasal spray. An intranasal formulation may comprise droplets having approximate diameters in the range of 100-5000 μm, such as 500-4000 μm, 1000-3000 μm or 100-1000 μm. Alternatively, in terms of volume, the droplets may be in the range of about 0.001-100 μl, such as 0.1-50 μl or 1.0-25 μl, or such as 0.001-1 μl.

Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 μm, preferably 1-25 μm, more preferably 1-5 μm.

Aerosol particles may be for delivery using a nebulizer (e.g. via the mouth) or nasal spray. An aerosol formulation may optionally contain a propellant and/or surfactant.

Preferably, the composition of the invention is a vaccine composition, e.g. suitable for parenteral administration, optionally together with one or more adjuvants.

As used herein, a vaccine is a formulation that, when administered to an animal subject such as a mammal (e.g. a human, bovine, porcine, ovine, caprine, equine, cervine, canine or feline subject; in particular a human subject), stimulates a protective immune response against an infectious disease. The immune response may be a humoral and/or a cell-mediated immune response. Thus, the vaccine may stimulate B cells and/or T cells.

Examples of suitable adjuvants include those which are selected from the group consisting of:

metal salts such as aluminium hydroxide or aluminium phosphate, oil in water emulsions, toll like receptors agonist, (such as toll like receptor 2 agonist, toll like receptor 3 agonist, toll like receptor 4 agonist, toll like receptor 7 agonist, toll like receptor 8 agonist and toll like receptor 9 agonist), saponins, for example Quil A and its derivatives such as QS7 and/or QS21, CpG containing oligonucleotides,

3D-MPL, (2-deoxy-6-o-[2-deoxy-2-[(R)-3-dodecanoyloxytetra-decanoylamino]-4-o-phosphono-β-D-glucopyranosy]]-2-[(R)-3-hydroxytetradecanoylamino]-α-D-glucopyranosyldihydrogenphosphate), DP (3S, 9 R)-3-[(R)-dodecanoyloxytetradecanoylamino]-4-oxo-5-aza-9(R)-[(R)-3-hydroxytetradecanoylamino] decan-1, 10-diol, 1,10-bis(dihydrogenophosphate), and MP-Ac DP (3S-, 9R)-3-[(R)-dodecanoyloxytetradecanoylamino]-4-oxo-5-aza-9-[(R)-3-hydroxytetradecanoylamino]decand, 10-diol, 1-dihydrogenophosphate 10-(6-aminohexanoate), or combinations thereof.

Preferably, the adjuvant is selected from the group comprising:

a saponin associated with a metallic salt, such as aluminium hydroxide or aluminium phosphate 3D-MPL, QS21 and a CpG oligonucleotide, for example as an oil in water formulation, saponin in the form of a liposome, for example further comprise a sterol such as QS21 and sterol, and

ISCOM.

In some particularly preferred embodiments, the adjuvant comprises a saponin. Saponins are steroid or triterpenoid glycosides, which occur in many plant species. Saponin-based adjuvants act in part by stimulating the entry of antigen-presenting cells into the injection site and enhancing antigen presentation in the local lymph nodes.

Preferably, the adjuvant comprises saponin, cholesterol and a phospholipid, e.g. ISCOM Matrix-M™ (Isconova, Novavax).

In Matrix-M, purified saponin fractions are mixed with synthetic cholesterol and a phospholipid to form stable particles than can be readily formulated with a variety of vaccine antigens. Matrix-M™ induces both a cell-mediated and an antibody mediated immune response.

In some other preferred embodiments, the adjuvant comprises a squalene-oil-in-water nano-emulsion emulsion, e.g. AddaVax™ (InvivoGen).

Squalene is an oil which is more readily metabolized than the paraffin oil used in Freund's adjuvants. Squalene oil-in-water emulsions are known to elicit both cellular (Th1) and humoral (Th2) immune responses. This class of adjuvants is believed to act through recruitment and activation of APC and stimulation of cytokines and chemokines production by macrophages and granulocytes.

The composition may further comprise a surfactant. Examples of suitable surfactants include Tween (such as Tween 20), briji and polyethylene glycol.

Vaccine preparation is generally described in New Trends and Developments in Vaccines, edited by Voller et al., University Park Press, Baltimore, Md., U.S.A., 1978. Encapsulation within liposomes is described, for example, by Fullerton, U.S. Pat. No. 4,235,877.

The amount of the polypeptide, nucleic acid molecule, vector, or particle of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each does will comprise 1-1000 μg of protein, for example 1-200 μg, such as 10-100 μg, and more particularly 10-40 μg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists. The immune response to the products of this invention is enhanced by the use of adjuvant and or an immunostimulant.

The amount of saponin for use in the adjuvants of the present invention may be in the region of 1-1000 μg per dose, generally 1-500 μg per dose, more such as 1-250 μg per dose, and more specifically between 1 to 100 μg per dose (e.g. 10, 20, 30, 40, 50, 60, 70, 80 or 90 μg per dose).

The invention also provides a combined preparation comprising two or more components selected from two or more polypeptides of the invention, two or more particles of the invention, two or more nucleic acids of the invention, two or more vectors of the invention and two or more compositions of the invention as a combined preparation in a form suitable for simultaneous, separate or sequential use, preferably for treating or preventing influenza A infection.

In yet another aspect, the invention provides an antibody against a polypeptide of the invention.

In yet further embodiments, the invention provides a polypeptide of the invention, a particle of the invention, a nucleic acid of the invention, a vector of the invention or a composition of the invention for use in therapy or for use as a medicament.

In a further aspect, the invention provides a polypeptide of the invention, a particle of the invention, a nucleic acid of the invention, a vector of the invention or a composition of the invention for use in a method of preventing or treating influenza infection in a subject.

In a further aspect, the invention provides a polypeptide of the invention, a particle of the invention, a nucleic acid of the invention, a vector of the invention or a composition of the invention for use in a method of inducing a T-cell or B-cell response to an influenza antigen in a subject.

In particular, a non-replicating poxvirus vector of the invention can be used to stimulate a protective immune response via the cell-mediated immune system. In one embodiment, the T-cell is a T-helper cell ($T_h$-cell). In one embodiment, the T-cell is a $T_h$17-cell.

In further embodiments, the invention provides the use of a polypeptide of the invention, a particle of the invention, a nucleic acid of the invention, a vector of the invention or a composition of the invention in the manufacture of a medicament for use in a method of preventing or treating an influenza infection in a subject.

In further embodiments, the invention provides the use of a polypeptide of the invention, a particle of the invention, a nucleic acid of the invention, a vector of the invention or a composition of the invention in the manufacture of a medicament for use in a method of inducing a T cell or B-cell response to an influenza antigen in a subject.

The invention also provides a method of treating a subject susceptible to influenza infection comprising administering an effective amount of a polypeptide of the invention, a particle of the invention, a nucleic acid of the invention, a vector of the invention or a composition of the invention to the subject.

The invention also provides a method of inducing a T-cell or B-cell response to an influenza antigen in a subject comprising administering an effective amount of a polypeptide of the invention, a particle of the invention, a nucleic acid of the invention, a vector of the invention or a composition of the invention to the subject.

A polypeptide of the invention, a particle of the invention, a nucleic acid of the invention, a vector of the invention or a composition of the invention may also be used in similar uses and methods to produce neutralising antibodies in vivo against influenza antigens.

Preferably, the influenza antigen is the haemagglutinin protein, more preferably, the HA1 or head domain of a haemagglutinin protein.

Preferably, the influenza is an influenza A.

The efficacy of the uses and methods to treat/prevent influenza infection may be tested (e.g. by ELISA) by establishing the presence or absence of neutralising antibodies against influenza virus in the subject's blood.

Also provided is an immunogenic composition comprising two or more polypeptides, two or more nucleic acid molecules or two or more vectors or plasmids as defined herein as a combined preparation in a form suitable for simultaneous, separate or sequential use for the treatment or prevention of influenza, preferably influenza A, or for inducing a T-cell or B-cell response in a subject against an influenza virus, preferably an influenza A virus.

The subject is preferably a mammal, more preferably a human.

As used herein, the term "preventing" includes preventing the initiation of influenza infection and/or reducing the severity of intensity of an influenza infection. Thus, "preventing" encompasses vaccination.

As used herein, the term "treating" embraces therapeutic and preventative/prophylactic measures (including post-exposure prophylaxis) and includes post-infection therapy and amelioration of an influenza infection. Each of the above-described methods and uses can comprise the step of administering to a subject an effective amount, such as a therapeutically effective amount, of a polypeptide of the invention, a particle of the invention, a nucleic acid of the invention, a vector of the invention or a composition of the invention.

As used herein, an effective amount is a dosage or amount that is sufficient to achieve a desired biological outcome. As used herein, a therapeutically effective amount is an amount which is effective, upon single or multiple dose administration to a subject (such as a mammalian subject, in particular a human subject) for treating, preventing, curing, delaying, reducing the severity of, ameliorating at least one symptom of a disorder or recurring disorder, or prolonging the survival of the subject beyond that expected in the absence of such treatment.

Accordingly, the quantity of active ingredient to be administered depends on the subject to be treated, capacity of the subject's immune system to generate a protective immune response, and the degree of protection required. Precise amounts of active ingredient required to be administered may depend on the judgement of the practitioner and may be particular to each subject. Administration to the subject can comprise administering to the subject a polypeptide of the invention, a particle of the invention, a nucleic acid of the invention, a vector of the invention or a composition of the invention (i.e. a product of the invention) wherein the product of the invention is sequentially administered multiple times (for example, wherein the composition is administered two, three or four times). Thus, in one embodiment, the subject is administered a polypeptide of the invention, a particle of the invention, a nucleic acid of the invention, a vector of the invention or a composition of the invention and is then administered the same product of the invention (or a substantially similar product) again at a different time.

In one embodiment, administration to a subject comprises administering a polypeptide of the invention, a particle of the invention, a nucleic acid of the invention, a vector of the invention or a composition of the invention to a subject, wherein said product of the invention is administered substantially prior to, simultaneously with, or subsequent to, another immunogenic composition.

The invention also extends to prime-boost regimes.

For example, priming and/or boosting may be effected using one or more products of the invention. The products may be administered to a subject sequentially, simultaneously or separately.

A preferred prime-boost strategy of the invention provides a method of preventing or treating an influenza infection in a subject or of inducing a T-cell or B-cell response to an influenza antigen in a subject, the method comprising the steps of:

(i) simultaneously, separately or sequentially administering an effective amount of one, two, three, four, five or more different polypeptides to a subject in need thereof, wherein each polypeptide independently comprises a first region of contiguous amino acids, wherein:

(a) the amino acid sequence of the first region has at least 80% sequence identity to an influenza A haemagglutinin head domain; and (b) the first region has one or more amino acid substitutions at positions which correspond to the following positions in SEQ ID NO: 9:

position 83 is E position 85 is a negatively charged amino acid position 146 is T, N, I or A position 147 is a positively charged amino acid, I or is absent position 148 is G position 149 is V position 151 is A position 154 is S or P position 155 is H position 156 is a positively charged amino acid or A or G or N or E position 157 is a positively charged amino acid or A or G position 158 is a positively charged amino acid or A or S or N or C or E position 159 is K or A or S or N or C position 163 is a positively charged amino acid.

Preferred influenza A haemagglutinin head domain sequences and first region substitutions are disclosed herein, mutatis mutandis.

The polypeptides may be in the form of a pharmaceutical composition, preferably a vaccine composition, optionally together with one or more pharmaceutically-acceptable carriers, diluents, excipients and adjuvants.

Preferably, one or more of the polypeptides (as defined above) are in the form of one or more trimers. In some embodiments, the trimers are homotrimers. In other embodiments, the trimers are heterotrimers.

Preferably, the method comprises the additional steps of:

(ii) administering a boost with a second polypeptide to the subject; and optionally also (iii) administering a boost with a third polypeptide to the subject, wherein the second and third polypeptides (as defined above) are preferably different to each other and preferably different to the first polypeptide.

Preferably, the method comprises the additional steps of:

(ii) administering a boost with a second trimer to the subject; and optionally also (iii) administering a boost with a third trimer to the subject, wherein the second and third trimers are preferably different to each other and preferably different to the first trimer.

Preferably, the first, second and third polypeptides are independently selected from the group consisting of polypeptides comprising or consisting of SEQ ID NOs: 13-17.

Preferably, the first, second and third trimers independently consist of polypeptides comprising or consisting of SEQ ID NOs: 13-17.

In a preferred embodiment, polypeptides or homotrimers of SEQ ID NOs: 14 and 15 are first administered to the subject; polypeptides or homotrimers of SEQ ID NOs: 13 and 16 are next administered to the subject; and polypeptides or homotrimers of SEQ ID NO: 17 are then administered to the subject.

In another preferred embodiment, the polypeptides or trimers are administered in the form of a VLP, i.e. a VLP is administered which comprises the polypeptide(s) trimer(s).

In another preferred embodiment, a nucleic acid molecule (preferably a vector) is administered to the subject, wherein the nucleic acid molecule encodes one or more of the polypeptides as defined above. Preferred vectors are discussed herein.

In one embodiment, the first and second products are administered as part of a prime-boost administration protocol. Thus, the first product may be administered to a subject as the “prime” and the second product subsequently administered to the same subject as the “boost”.

In one embodiment, the first product is an adenovirus vector of the invention prime, and the second product is a non-replicating poxvirus vector of the invention boost.

In one embodiment, each of the above-described methods further comprises the step of administration to the subject of a product of the invention.

In one embodiment, the polypeptide of the invention is administered separately from the administration of a viral vector of the invention. Preferably the polypeptide and a viral vector are administered sequentially, in any order. Thus, in one embodiment, the viral vector (“V”) and the polypeptide (“P”) may be administered in the order V-P, or in the order P-V.

In certain embodiments, the above-described methods further comprise the administration to the subject of an adjuvant. Adjuvant may be administered with any of the products of the invention.

The products of the invention may be given in a single dose schedule (i.e. the full dose is given at substantially one time). Alternatively, the products of the invention may be given in a multiple dose schedule.

A multiple dose schedule is one in which a primary course of treatment (e.g. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months.

The dosage regimen will be determined, at least in part, by the need of the individual and be dependent upon the judgment of the practitioner (e.g. doctor or veterinarian).

Simultaneous administration means administration at (substantially) the same time.

Sequential administration of two or more products of the invention means that the products are administered at (substantially) different times, one after the other.

For example, sequential administration may encompass administration of two or more products of the invention at different times, wherein the different times are separated by a number of days (for example, 1, 2, 5, 10, 15, 20, 30, 60, 90, 100, 150 or 200 days).

For example, in one embodiment, the vaccine of the present invention may be administered as part of a 'prime-boost' vaccination regime.

In one embodiment, the products of the invention can be administered to a subject such as a mammal (e.g. a human, bovine, porcine, ovine, caprine, equine, *cervine*, canine or feline subject) in conjunction with (simultaneously or sequentially) one or more immunoregulatory agents selected from, for example, immunoglobulins, antibiotics, interleukins (e.g. IL-2, IL-12), and/or cytokines (e.g. IFN-γ).

In yet further embodiments, the invention provides a process for the production of a one or more of polypeptides of the invention, which process comprises expressing one or more nucleic acid molecules coding for one, two or more of said polypeptides in a suitable host, and recovering the polypeptide product(s).

Preferably, the host is a human cell.

There are many established algorithms available to align two amino acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer-implemented algorithms (e.g. GAP, BESTFIT, FASTA or TFASTA), or BLAST and BLAST 2.0 algorithms.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGABLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blastlab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

In some embodiments, the BLASTP 2.5.0+ algorithm may be used (such as that available from the NCBI) using the default parameters.

In other embodiments, a BLAST Global Alignment program may be used (such as that available from the NCBI) using a Needleman-Wunsch alignment of two protein sequences with the gap costs: Existence 11 and Extension 1.

The method of identifying sites of limited variability and subsequent epitopes of limited variability as disclosed herein may be applied to all influenza A subtypes. In particular, since the H3 subtype influenza A virus evolves in a similar way to the H1 subtype influenza A virus, the approach disclosed herein to identifying epitopes is particularly applicable to H3 subtypes of influenza A.

In yet a further embodiment, therefore, the invention provides a method for identifying an epitope on a haemagglutinin head domain of an influenza virus of a defined subtype, the method comprising the steps of:

(i) identifying a possible antibody binding site on a haemagglutinin head domain polypeptide of an influenza virus of a defined subtype;

(ii) identifying one or more continuous or discontinuous stretches of the head domain polypeptide within the possible antibody binding site; and (iii) comparing the amino acid sequences of those stretches with amino acid sequences of haemagglutinin head domains from a plurality of influenza strains of the defined subtype in order to identify regions of limited amino acid sequence variability within those stretches;

thereby identifying a set of positions which have limited variability in their amino acid composition within the haemagglutinin head domain of the influenza virus of the defined subtype and which form an epitope.

The epitopes which are identified in this way are under strong immune selection such that they periodically repeat through a limited number of forms throughout the evolution of the influenza virus.

The method and process may be applied to any influenza virus. Preferably, the influenza virus is an influenza A virus.

The influenza virus may be of any subtype, e.g. H1, H2, H3, H4, H5, H6, H7, H8, H9, H10, H11, H12, H13, H14, H15, H16, H17 or H18. Preferably, the influenza virus is of the H1 or H3 subtype.

Step (i) requires identifying a possible antibody binding site on a haemagglutinin head domain polypeptide of an influenza virus of a defined subtype.

This may be done by analysing the crystal structure of the haemagglutinin head domain polypeptide. Crystal structures of two or more head domains from influenza viruses of the defined subtype may be aligned to determine which residues are present on the surface of the polypeptide and the accessibility of those residues. Typically, the accessibility of the positions are the same in all crystal structures but when a position is more accessible in one crystal structure than another crystal structure, the position is allocated as being more accessible to prevent the false identification of sites of limited variability.

In silico analysis may be used to determine how the accessibility and binding site area contribute to the variability of hypothetical antibody binding sites. An antibody binding site of between 600 $A^2$ and 1000 $A^2$ may be used to determining the variability for accessibility parameters of amino acids with between >30% and >1% accessibility.

Step (ii) requires identifying one or more continuous or discontinuous stretches of the head domain polypeptide within the possible antibody binding site. These stretches may be contacted by the antibody.

Once possible antibody binding sites have been identified, one or more continuous or discontinuous stretches of the head domain polypeptide within the possible antibody binding site may be identified, for example, by using Swiss-pdb viewer.

Step (iii) requires comparing the amino acid sequences of the continuous or discontinuous stretches with amino acid sequences of haemagglutinin head domains from a plurality of influenza strains of the defined subtype in order to identify regions of limited amino acid sequence variability within those stretches.

For example, the plurality of influenza strain sequences may be obtained from yearly consensus sequences of the haemagglutinin head domains of the influenza strains of the defined subtype. The yearly consensus sequences may be generated by dividing curated haemagglutinin sequences into separate datasets based on the year that the sequence was collected. The R package 'seqinr' or an alternate consensus sequence generating program may then be used to generate consensus sequences.

As used herein, the term "limited sequence variability" refers to an amino acid or sequences of amino acids which are restricted in the number of different epitope conformations they can form.

In other embodiments, the term "limited sequence variability" refers to amino acid positions at which 0, 1, 2, 3 or 4 (preferably 0 or 1) different amino acids were found during the amino acid sequence comparisons.

In this way, a set of conserved amino acids within the haemagglutinin head domain of the influenza virus of the defined subtype may be identified which form an epitope.

The epitope may be one which is bound by an antibody. Preferably, the epitope is an epitope of limited variability.

The invention also provides a process for producing a polypeptide, the process comprising the steps of:

(i) using a method for identifying an epitope as defined herein to identify a set of amino acids with limited variability within a haemagglutinin head domain of an influenza virus of a defined subtype;

(ii) producing a polypeptide which comprises a first region of contiguous amino acids, wherein:

(a) the amino acid sequence of the first region has at least 80% sequence identity to an influenza A haemagglutinin head domain; and (b) the first region has one or more amino acid substitutions at positions which correspond to the positions of the amino acid positions with limited variability, and wherein the substitution introduces the amino acid which is conserved at that position;

wherein the polypeptide is capable of inducing antibodies in a subject against an influenza A virus.

The invention also provides a process for producing an immunogenic composition, the process comprising the steps of:

(i) using a method for identifying an epitope as defined herein to identify a set of amino acid positions with limited variability within a haemagglutinin head domain of an influenza virus of a defined subtype;

(ii) producing a polypeptide which comprises a first region of contiguous amino acids, wherein:

(a) the amino acid sequence of the first region has at least 80% sequence identity to an influenza A haemagglutinin head domain; and (b) the first region has one or more amino acid substitutions at positions which correspond to the positions of the conserved amino acids, and wherein the substitution introduces the amino acid which is conserved at that position;

wherein the polypeptide is capable of inducing antibodies in a subject against an influenza A virus; and (iii) formulating one or more of the polypeptides into an immunogenic composition, wherein the composition optionally comprises one or more pharmaceutically-acceptable carriers, adjuvants, excipients or diluents.

The composition is capable of inducing antibodies in a subject against an influenza A virus.

With regard to influenza virus H3 subtype epitopes, the amino acid sequence of the first region preferably has at least 80%, 90% 95% or 100% sequence identity to an influenza A subtype H4, H7 H10, H14 or H15 haemagglutinin head domain.

The immunogenic composition is preferably a vaccine composition; it may be administered as a prime-boost-boost, e.g. using the compositions and regimes described herein.

The disclosure of each reference set forth herein is specifically incorporated herein by reference in its entirety.

(A) Microneutralisation assay using wild-type (WT) and −147K mutant A/Solomon Islands/3/2006 pseudotyped viruses.

(B) Microneutralisation assay using wild-type (WT) and −147K mutant A/Puerto Rico/8/1934 pseudotyped viruses.

(C) Microneutralisation assay using wild-type (WT) and −147K mutant A/WSN/1933 pseudotyped viruses.

FIG. 6: Sequential vaccination using chimeric HA constructs.

(A) Five groups of mice were sequentially vaccinated with the sequences outlined in (B), substituted into H6, H5 and H11 HAs. Two further groups were sequentially vaccinated with H6, H5 and H11 constructs without any sequence substituted into them and named 'grey' and 'purple'. A further two groups were mock vaccinated and named 'white' and 'black'. The first two vaccinations were administered as a 100 μg intra muscular injection of DNA, whilst the final vaccination was administered as an intra-muscular injection of 8 HI units of lentivirus displaying a chimeric HA (i.e. H11 with or without substitution) with an Alum adjuvant.

(B)-(F) Pseudotype microneutralisation assays using 0.5 μl of sera from the bleed at 21 weeks. Broad neutralising activity occurs against lentiviruses displaying H1 HAs from influenza viruses circulating in 1933, 1934, 1977, 2006 and 2009.

(G)-(J) Influenza challenge of vaccinated mice with either A/PR/8/1934 or A/California/4/2009. The graphs denote daily weight loss and percentage survival of the mice during the challenge.

FIG. 7: Sites of limited variability are present in the head of H1 HA.

(A) Antibody binding sites were mapped to the A/Puerto Rico/8/1934 crystal structure and the variability within those site determined by referring to an alignment of 2,756 H1 sequences. Only parts of A/Puerto Rico/8/1934 crystal structure accessible to antibody binding were considered. In A. an antibody binding site of 800 $A^2$ was used to determining the variability for three accessibility parameters: amino acids with >30%, >10% or >1% accessibility.

(B) In B. a dataset of amino acids with >10% accessibility was used to determine the variability for three binding site sizes: 600, 800 or 1000 $A^2$. Both approaches identified the same regions within the head of H1 HA which are of limited variability. One of these regions contains our epitope of limited variability centring of position 156/158. Linear numbering of HA is used for the x-axis.

(C)-(J) Mapping of predicted antibody-binding sites onto the crystal structures of HA domains from specified influenza strains.

Figure 8A:
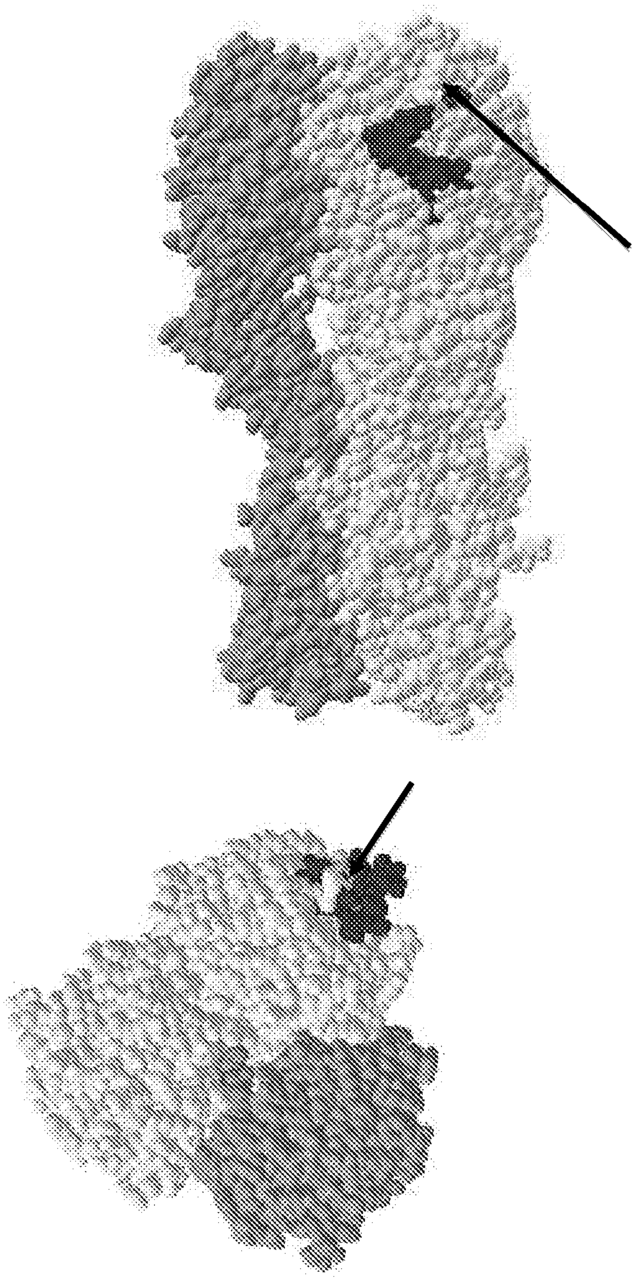
Figure 8B:
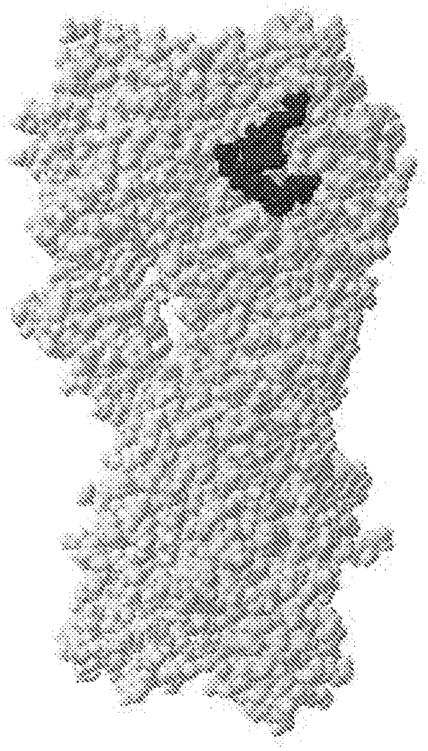
Figure 8B:
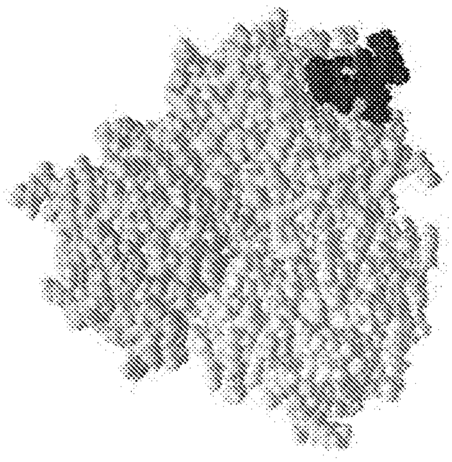

FIG. 8: The disrupted peptide sequence corresponding to the site surrounding amino acids 156/158. (A) shows the crystal structures of A/Brevig Mission/1/1918 and (B) shows the crystal structure of A/Puerto Rico/8/1934 from the side and above. The disrupted peptide sequence is mapped on the H1 structures. Amino acid position 147 is highlighted (in white and with an arrow) and is present in A/Brevig Mission/1/1918 but not A/Puerto Rico/8/1934.

Figure 9A:
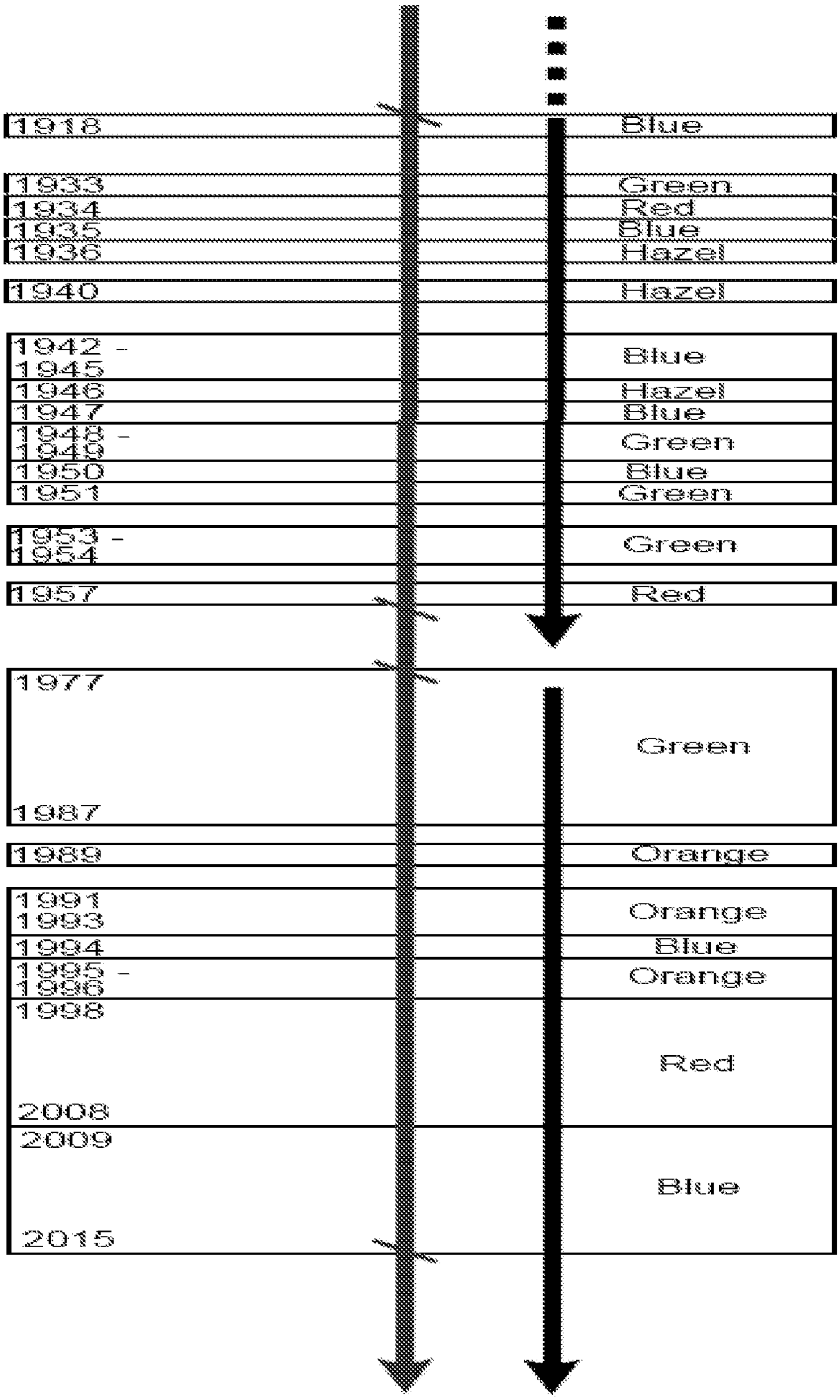

FIG. 9: Cyclical activity of the disrupted peptide sequence of a site of limited variability. Disrupted peptide sequences taken from yearly consensus sequences can be groups according to their chemical properties. If arranged with time, the cyclical nature of the disrupted peptide sequence becomes apparent. Other ways of arranging the sequences based on their chemical properties are possible and this is simply one possible incarnation and representative of the cyclical nature of this epitope region.

Figure 10:
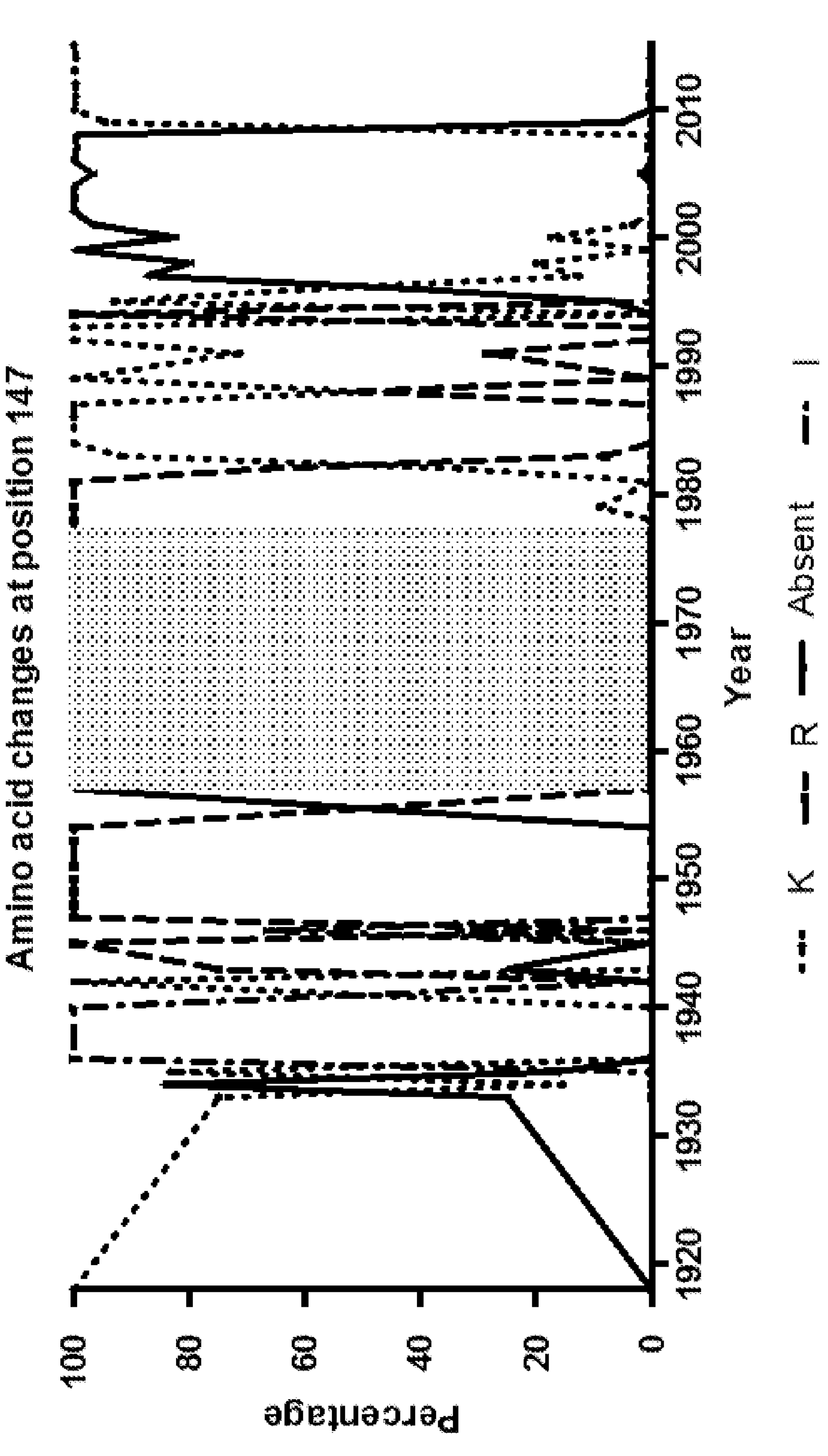

FIG. 10: Amino acid changes at position 147 cycle between four possibilities. A. The identity of amino acid at position 147 cycles between lysine, arginine, isoleucine and is absent for five periods between 1918-1957 and 1977-2015.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Antigenic Thrift Model

Figure 1:
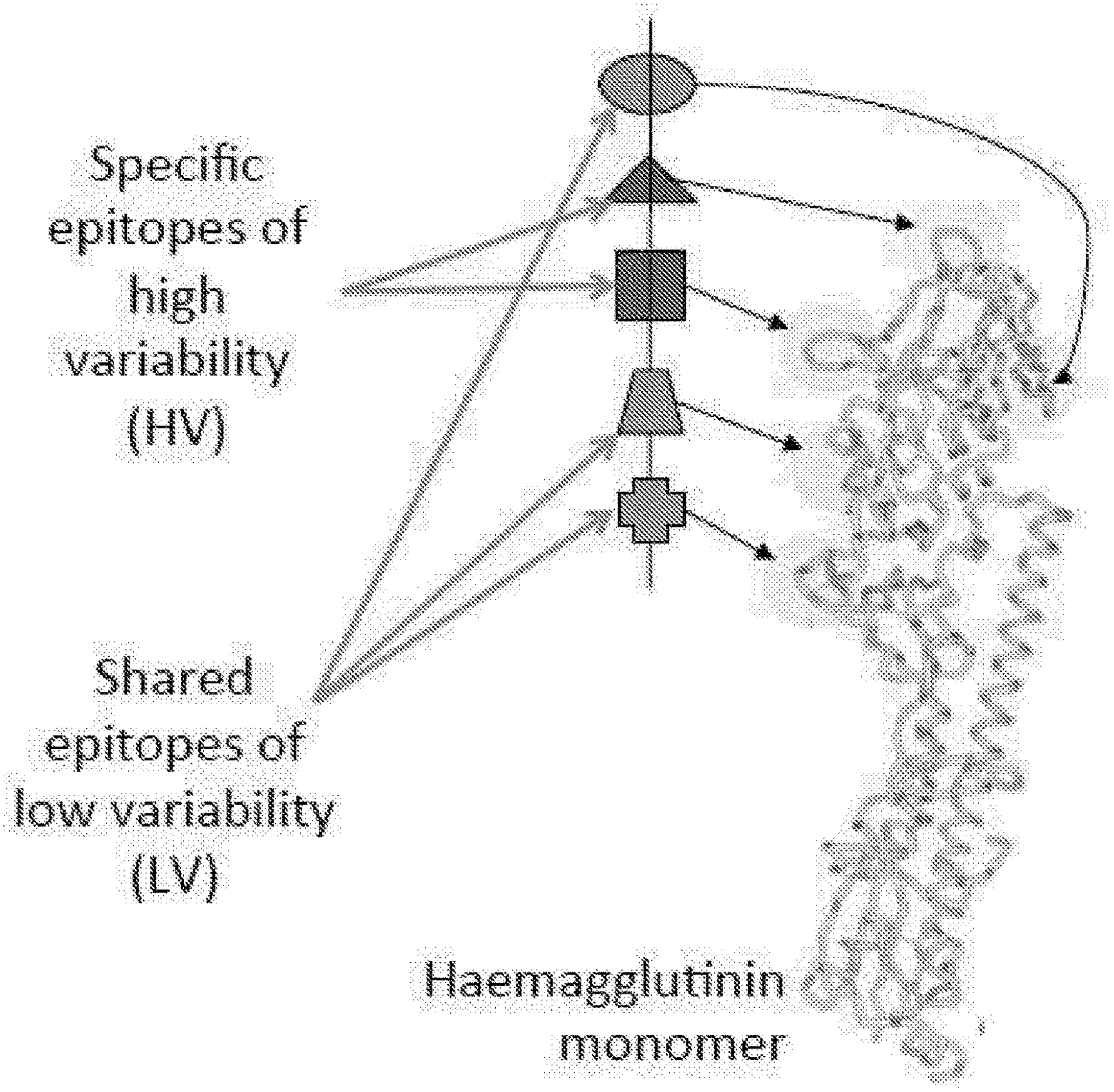
FIG. 1: A multi-locus representation of epitopes on a monomer of haemagglutinin (HA). Each influenza strain is assumed to contain specific epitopes of high variability as well as epitopes of low variability shared with other strains.
Figure 2:
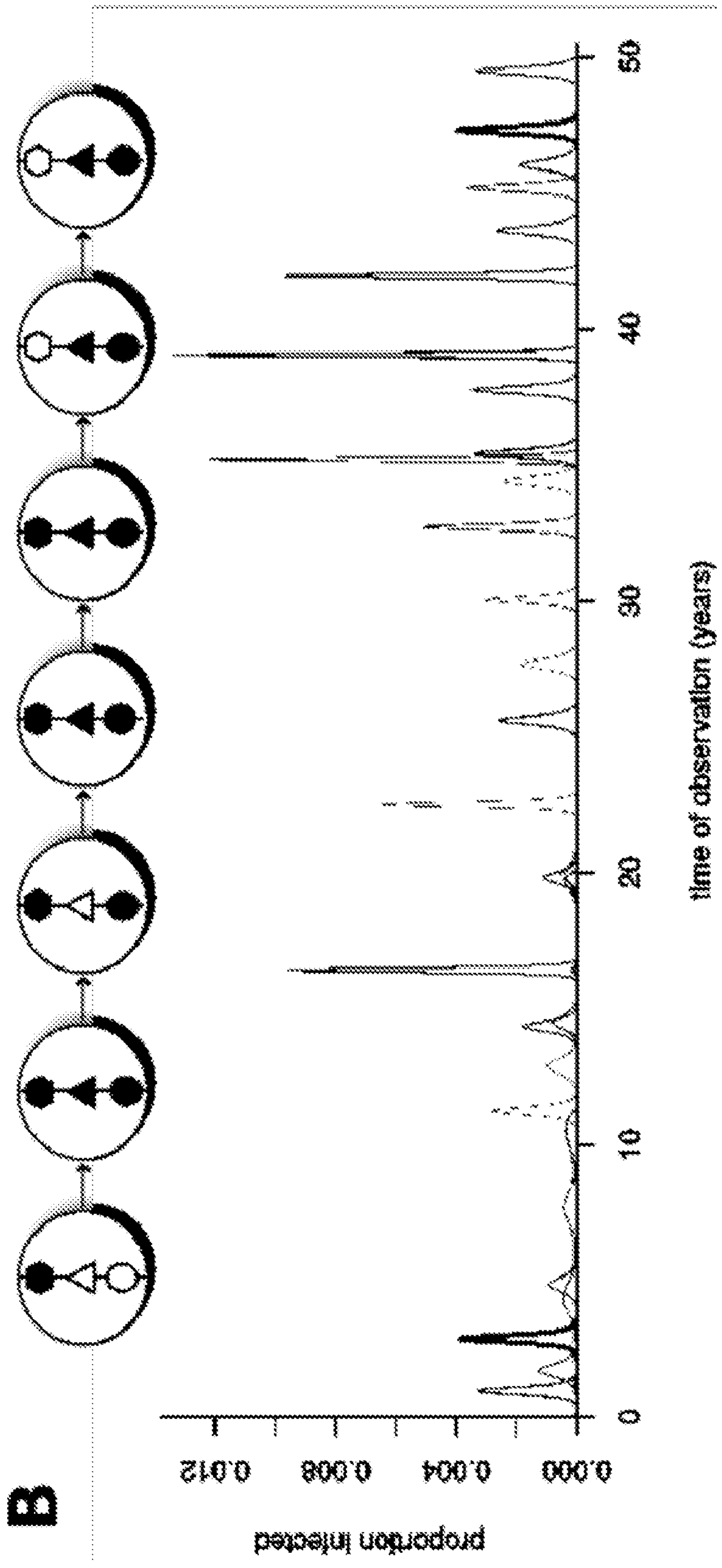
FIG. 2: Cyclical replacement of dominant antigenic types. The dynamics shown is for a 3-epitope system, each containing 3 possible variants as indicated in the cartoon.

The existence of protective epitopes of low variability is consistent with the population dynamics of influenza A under the "antigenic thrift model". This model is based on a multi-locus representation of the virus with each locus corresponding to an epitope region and presents an alternative to the more widely accepted "antigenic drift" model in having the potential to contain protective epitopes of limited variability as well as those of high variability. FIG. 1 shows how these may locate to the known antigenic sites on a monomer of haemagglutinin (HA). The epidemic behaviour of influenza can be readily explained within the antigenic thrift framework by assuming that most influenza strains are in competition with each other because they share epitopes in regions of low variability (Recker et al. 2007; Wikramaratna et al. 2013). Thus although new strains may be generated constantly through mutation, most of these cannot expand in the host population due to pre-existing immune responses against their less variable epitopes. This leads to cyclical dominance of antigenic types (FIG. 2). By contrast with the "antigenic drift" model, antigenic distance between epidemic strains does not necessarily accumulate with time; instead it periodically expands and contracts.

Figure 5A:
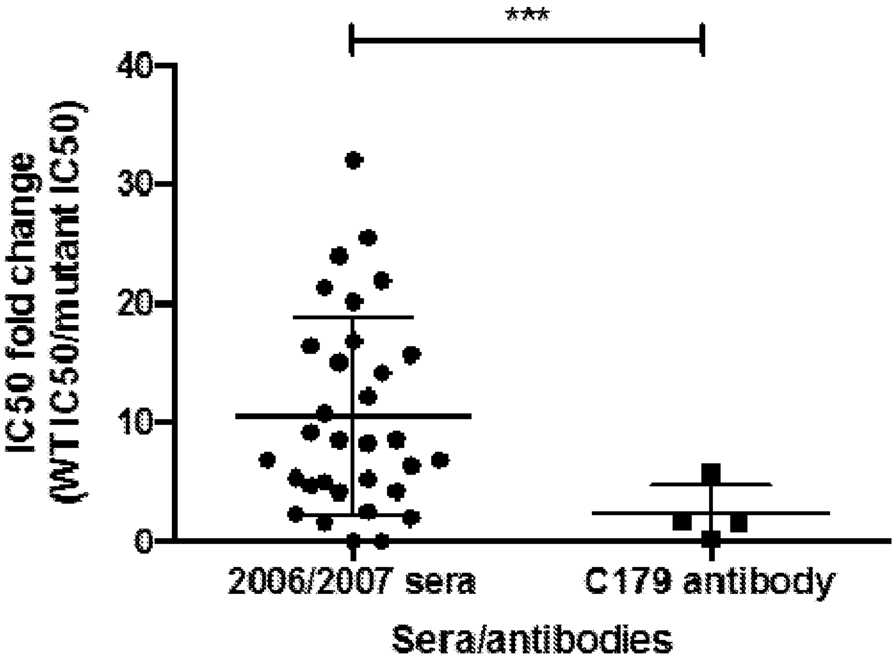
FIG. 5: Microneutralisation assays. The x-axis refers to the ratio of the IC50s of the pseudotype viruses to produce a fold-change.
Figure 5B:
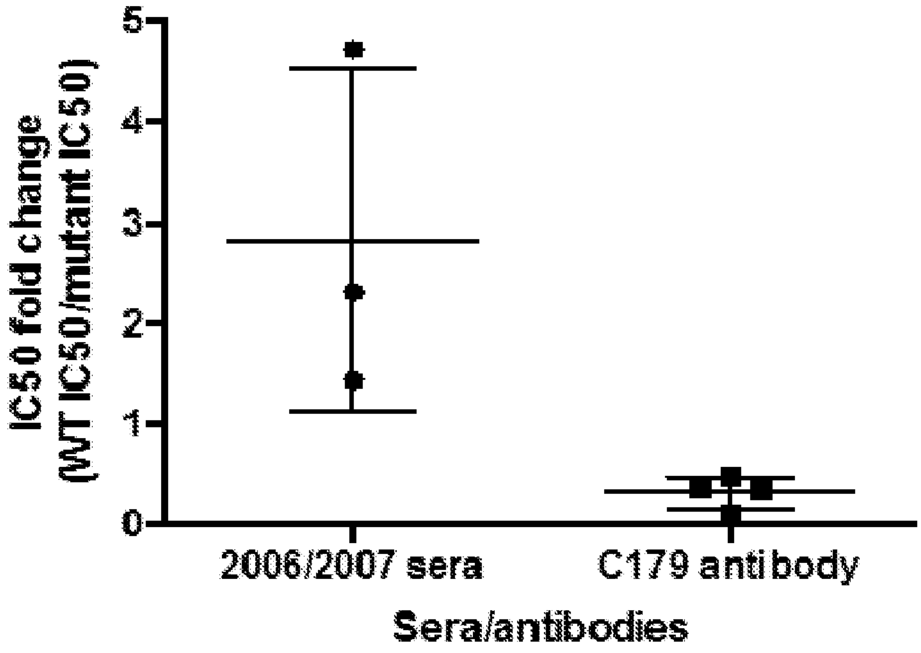
Figure 5C:
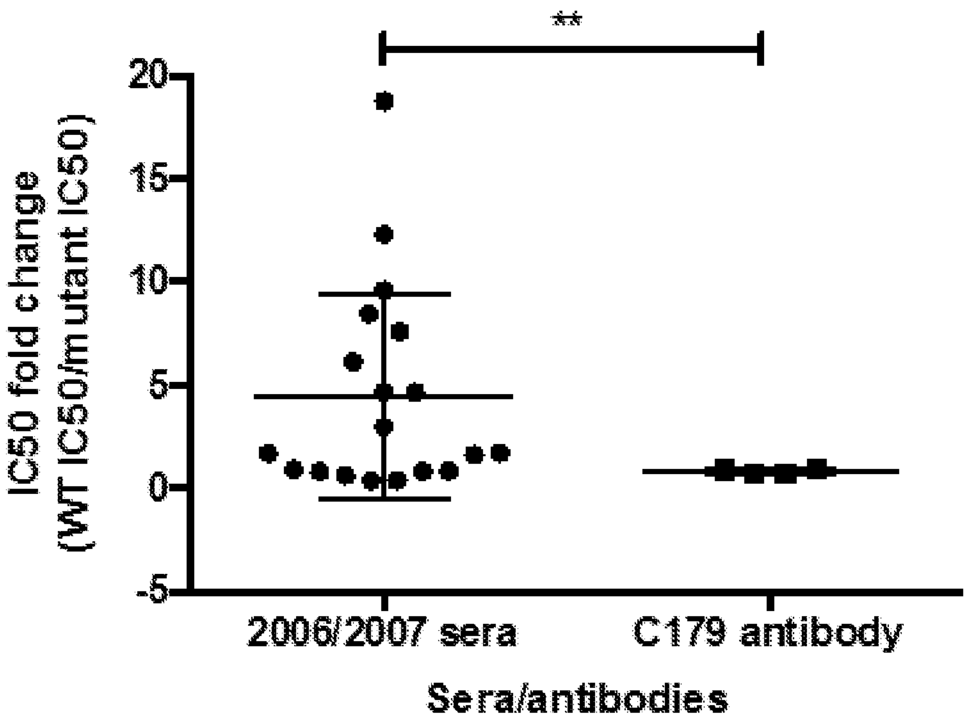

Carter et al. (2013) provides evidence for the antigenic thrift model. Ferrets were infected with one of several historical influenza viruses. Serum antibodies were measured at day 14 and 81 by haemagglutin inhibition (HAI)

assays (FIG. 5) and showed a periodic cross-reactivity of antibodies to viruses of historic strains, as predicted by the antigenic thrift hypothesis.

The observed periodic cross-reactivity in Carter et al. (2013) is predicted, in part, by the current structural bioinformatics analysis. For example, infection of ferrets with the 1957 strain is predicted to induce cross-reactive antibodies to the A/R/8/1934, A/Den/1/1957, A/NC/20/1999 and A/Bris/59/2007 strains. Cross-reactivity is observed between the A/R/8/1934, A/Den/1/1957 and A/NC/20/1999 strains on infection, but not the A/Bris/59/2007 strain.

Example 2: Cyclical Cross-Reactivity of Infant Plasma Against Chronologically-Dispersed H1 Influenza Strains Standardised enzyme-linked immunosorbant assays (ELISAs) were performed using plasma from children aged 12 to 17 months, collected in 2012. The HA1 domains from influenza strains A/California/4/2009, A/USSR/90/1977, A/Brevig Mission/1/1918, A/Solomon Islands/3/2006, A/New Caledonia/20/1999, A/Puerto Rico/8/34 and A/WSN/33 were bought from Sino Biological. Standards used sera from adults based on their date of birth. Two negative controls were run on each plate consisting of a caesin only control and a non-reactive human plasma or sera control.

Figure 3:
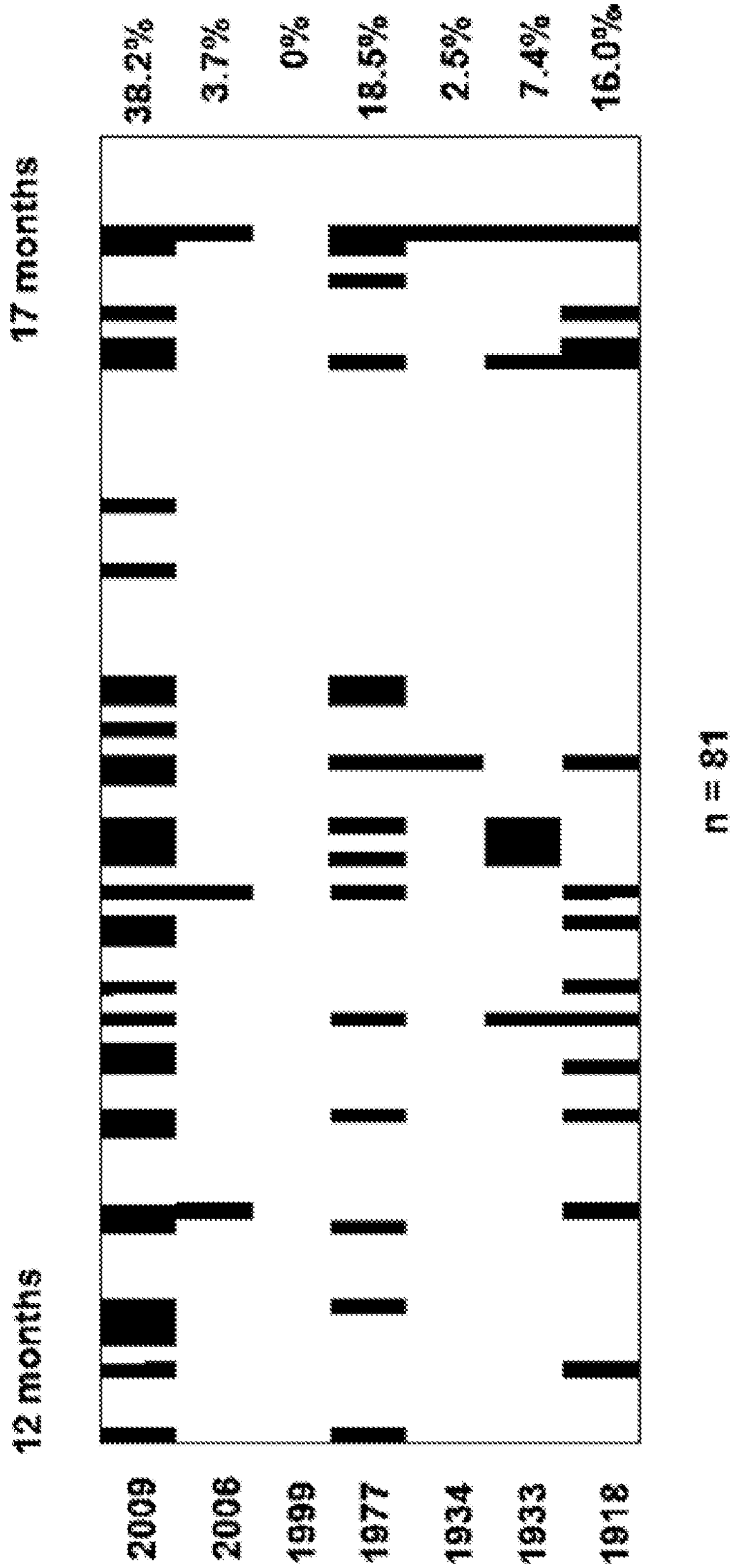
FIG. 3: "Heat map" of plasma from children showing cyclical cross-reactivity with a number of influenza strains. The year on the left hand side of the heat map relates to the strain from which the HA1 domain was taken. Individuals are aligned from 12 to 17 months left to right. Percentage reactivity is stated to the right hand side of the heat map.

The results are shown in FIG. 3. Plasma from 81 children aged 12 to 17 months, collected in 2012, cross-reacted with HA1 domains (the head domain and part of the stem domain of HA H1) from influenza strains A/California/4/2009, A/USSR/90/1977 and A/Brevig Mission/1/1918 but not A/Solomon Islands/3/2006, A/New Caledonia/20/1999, A/Puerto Rico/8/34 or A/WSN/33. All ELISA results were completed in triplicate and normalised to non-reactive human plasma. ELISA results were accepted or declined based on the criteria set out in Miura et al. (2008).

The fact that this plasma reacted with a panel of historical H1N1 strains in a cyclical manner lead us to infer that epitopes of limited variability are present in the head domain of H1 HA and that they cycle through a limited number of conformations as host population immunity changes.

Example 3: Identification of Epitopes of Limited Variability

To identify epitopes of limited variability, antibody binding sites were mapped to the A/Puerto Rico/8/1934 crystal structure and the variability within those site determined by referring to an alignment of 2,756 H1 sequences (FIG. 7). Only parts of A/Puerto Rico/8/1934 crystal structure accessible to antibody binding were considered. This was determined by aligning the crystal structures of A/Puerto Rico/8/1934, A/Brevig Mission/1/1918 and A/California/04/2009 to determine which residues were present on the surface of the protein and the accessibility of those residues. Typically, the accessibility of the positions were the same in all crystal structures but when a position was more accessible in one crystal structure than another crystal structure, the position was allocated as being more accessible to prevent the false identification of sites of limited variability. Parts of the HA contained within the virion were also not considered for analysis.

In silico analysis was used to determine how the accessibility and binding site area contributed to the variability of hypothetical antibody binding sites. An antibody binding site of 800 $A^2$ was used to determining the variability for three accessibility parameters: amino acids with >30%, >10% or >1% accessibility. A dataset of positions with >10% accessibility was used to determine the variability for three binding site sizes: 600 $A^2$, 800 $A^2$ or 1000 $A^2$. Both approaches identified the same regions of limited variability within the head of H1 HA (FIG. 7).

Analysis of the sites of limited variability predicted to exist from the in silico analysis was performed by mapping the predicted epitopes to the A/Puerto Rico/8/1934, A/Brevig Mission/1/1918 and A/California/04/2009 crystal structures using Swiss-pdb viewer. By mapping the predicted sites to the crystal structures, sites that were likely to be epitopes could be identified. One site close to the receptor binding site (RBS), in a region which is known to be under strong immune selection but thought to be highly variable, centred on a 800 $A^2$ region surrounding this positions 156/158 (FIG. 8; Caton et al. 1982).

Example 4: Cycling of Epitopes

Yearly consensus sequences were generated by dividing the 12,480 curated H1 HA sequences into separate fasta files based on the year that the sequence was collected. The R package 'seqinr' was then used to generate consensus sequences.

Analysis of the predicted binding site surrounding positions 156/158 indicated that there were a number of positions in which charged residues could be found, in addition to positions with non-charged residues, which were either conserved or changed between similar residue types. It is generally accepted that antibodies preferentially bind to charged residues and so the possible epitope permutations were defined based on the cycling of charged amino acids in positions 147, 156, 157, 158 and 159 (Kringelum et al. 2013).

At position 147, the amino acid alternated between a positively charged amino acid, lysine or arginine, a neutral amino acid, isoleucine, and no amino acid. Consequently the site was divided up based on this pattern into three groups.

Phylogenetic analysis of position 147 also reveals that strains were identified in which no amino acid was present at position 147 five times during the evolution of H1 influenza in humans between 1918-1957 and 1977-2015 (FIG. 10). It was also found to cycle between lysine, arginine, isoleucine and no amino acid. Consequently, the importance to having a vaccine containing both arginine and lysine as positively charged amino acids were highlighted. This also indicated that the site is structurally limited and cycling between a small number of conformations.

The 147 positive group was then further divided based on the presence of a positively charged amino acid at position 158 or 159, 158 and either a positive charged amino acid at position 156 or 157.

The space filling capacity of non-charged amino acid was then considered, which allowed an addition group to be produced from 147-positive/158 or 157 positive group based on whether alanine or asparagine was present at position 156 (FIG. 9).

Example 5: Loss of Neutralisation Upon Site-Directed Mutagenesis

Figure 4:
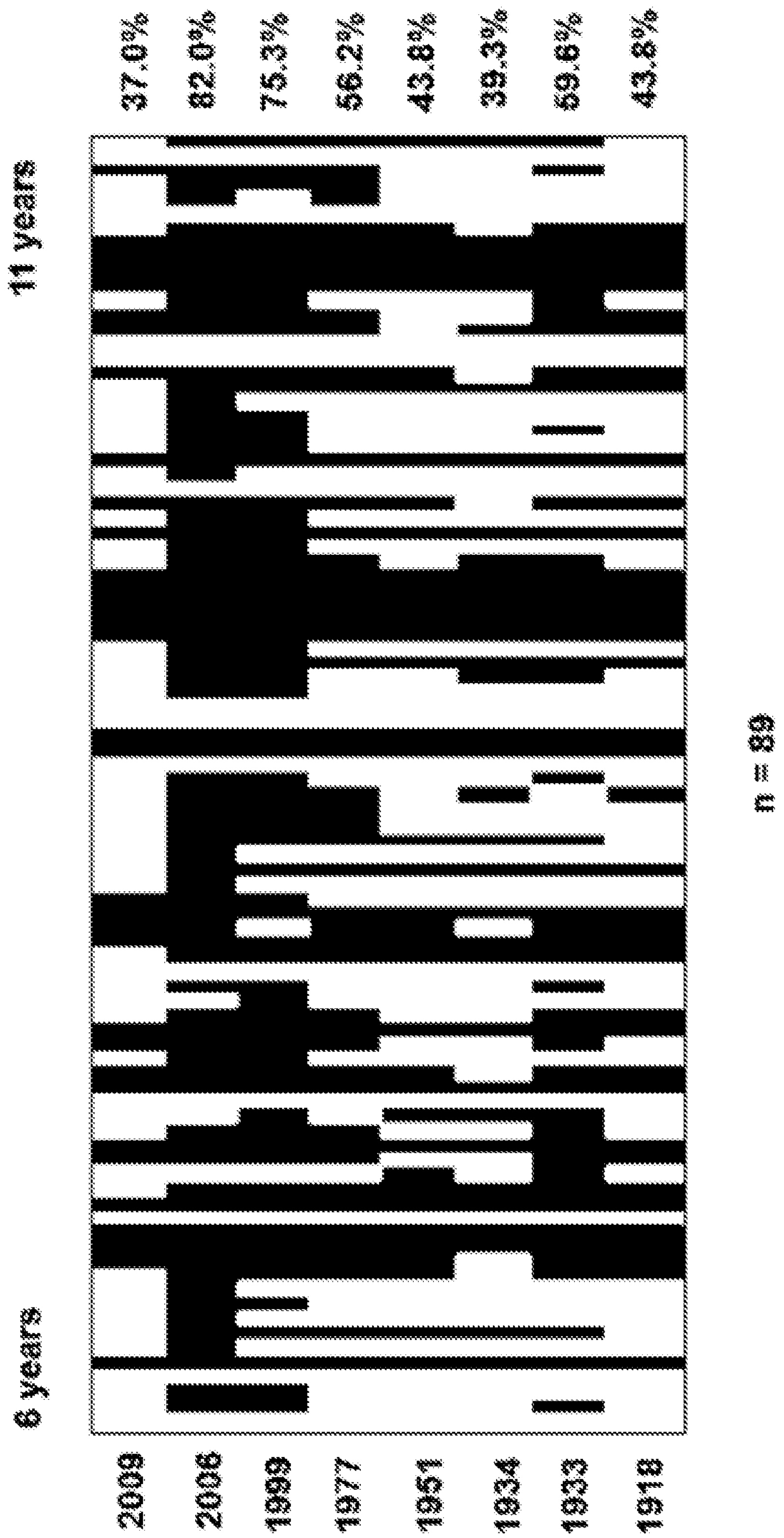
FIG. 4: "Heat map" of plasma from children showing cross-reactivity with a number of historical influenza strains. The year on the left hand side of the heat map relates to the strain from which the HA1 domain was taken. Individuals are aligned from 6 to 11 months left to right. Percentage reactivity is stated to the right hand side of the heat map.

Sera from children aged 6 to 11 years, taken in late 2006/early 2007, cross-reacted extensively with HA1 domains from historical influenza strains (FIG. 4). Cross-reactivity peaks towards to the HA1 domain from A/WSN/33 in addition to the A/New Caledonia/20/1999 HA1 domain which is closely related to the A/Solomon Islands/3/2006 HA1 domain. Cross-reactivity was also observed towards A/California/4/2009, A/USSR/90/1977, A/Albany/12/1951, A/Puerto Rico/8/34 and A/Brevig Mission/1/1918.

Using a microneutralisation assay (FIG. 5), up to a 32-fold loss of neutralisation to A/Solomon Islands/3/2006 pseudotyped lentivirus was observed when a lysine was inserted at position 147 (p-value: 0.0005). Up to a 18.75-fold loss of neutralisation of A/WSN/1933 pseudotyped lentivirus was also observed with the insertion of a lysine at position 147 (p-value of 0.0056). While only a 11 serum samples from the UK cohort showed cross-reactivity with A/PR/8/1934 pseudotyped lentivirus, the insertion of a lysine at position 147 caused total loss of neutralisation in 8 samples and a reduction in 3 samples. This indicates that the bulk of cross-reactivity between these strains is mediated through an epitope which contains a deletion in position 147.

This data emphasises the importance of amino acid position 147. It should be noted that in the A/Solomon Islands/3/2006, A/PR/8/1934 and A/WSN/1933 strains no amino acid is contained at position 147. Instead monomers of these viruses consist of 565 instead of 566 amino acids.

Example 6: Synthesis of Polypeptides

Invitrogen® GeneArt Strings were used to synthesise the chimeric HA molecules consisting of the epitope of limited variability substituted into the HA1 domain of H5, H6, or H11. Three conformations of the site were initially used.

The chimeric HA1 domain sequences were then cloned into DNA expression constructs and lentiviral glycoprotein expression vectors. The DNA expression were grown up in *E. coli* and purified using a Qiagen Giga Prep Kit. Lentiviruses were produced displaying the chimeric HAs via the protocol outlined in Carnell et al., (2015) before being purified by sucrose cushion centrifugation. The conformations substituted into the H6, H5 and H11 HA1 domains are provided below (amino acid position is denoted in brackets):

Blue:
N (146), K (147), G (148), V (149), A (151), P (154), H (155), A (156), G (157), A (158), K (159), K (163)
AAC (146) AAG (147) GGC (148) GTG (149) GCC (151) CCC (154) CAC (155) GCC (156) GGC (157) GCC (158) AAG (159) AAG (163)

Hazel:
N (146), I (147), G (148), V (149), A (151), S (154), H (155), A (156), G (157), K (158), S (159), K (163)
AAC (146) ATC (147) GGC (148) GTG (149) GCC (151) AGC (154) CAC (155) GCC (156) GGC (157) AAG (158) AGC (159) AAG (163)

Green:
T (146), R (147), G (148), V (149), A (151), S (154), H (155), K (156), G (157), K (158), S (159), R (163)
ACC (146) AGG (147) GGC (148) GTG (149) GCC (151) AGC (154) CAC (155) AAG (156) GGC (157) AAG (158) AGC (159) AGG (163)

Orange:
T (146), K (147), G (148), V (149), A (151), S (154), H (155), N (156), G (157), K (158), S (159), R (163)
ACC (146) AAG (147) GGC (148) GTG (149) GCC (151) AGC (154) CAC (155) AAC (156) GGC (157) AAG (158) AGC (159) AGG (163)

Red:
T (146), Absent (147), G (148), V (149), A (151), S (154), H (155), N (156), G (157), K (158), S (159), R (163)
ACC (146) Absent (147) GGC (148) GTG (149) GCC (151) AGC (154) CAC (155) AAC (156) GGC (157) AAG (158) AGC (159) AGG (163)

These sequences correspond to those cloned into the vaccine constructs and so any cross-reactivity can be directly attributed to them.

Example 7: Mouse Challenges

Mouse influenza challenges are performed with influenza strains:
(i) A/California/4/2009 at a concentration of $1*10^5$ Pfu and
(ii) A/PR/8/1934 at a concentration of $1*10^3$ Pfu. Weight changes were monitored on a daily basis. The optimisation of challenge experiments enables the protection induced by the vaccine in mice to be quantified in the vaccination studies.

Figure 6A:
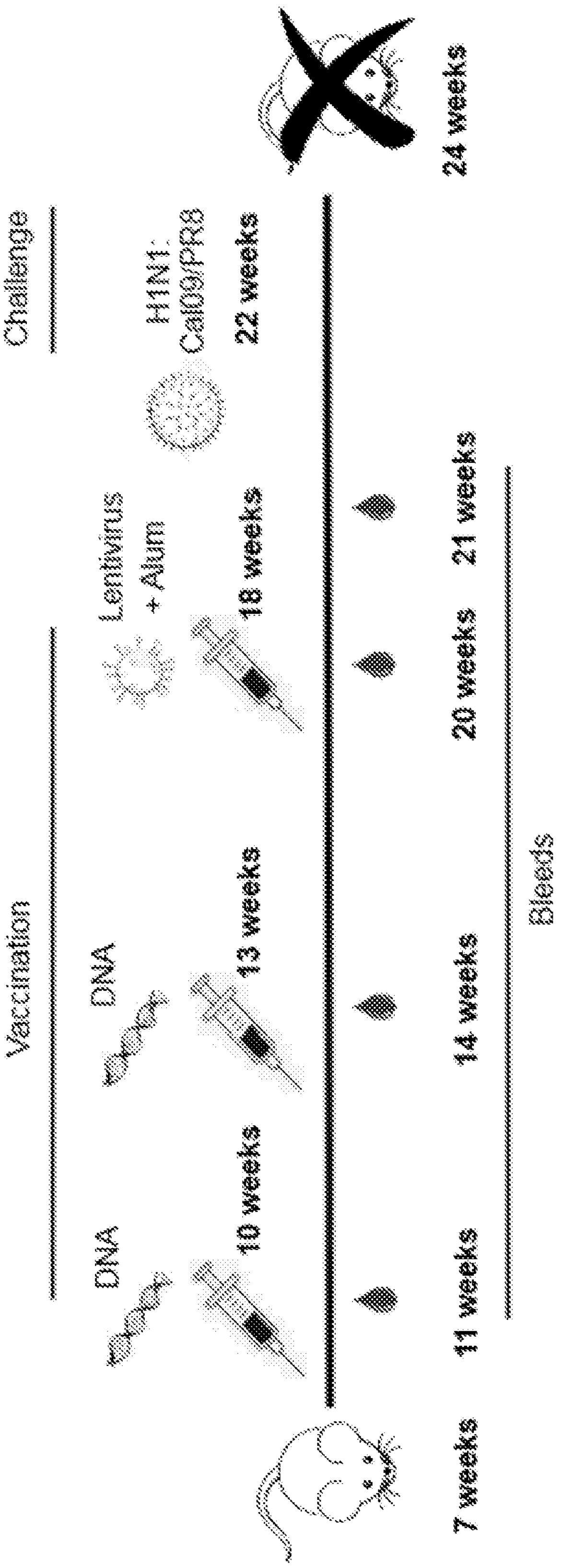
Figure 6B:
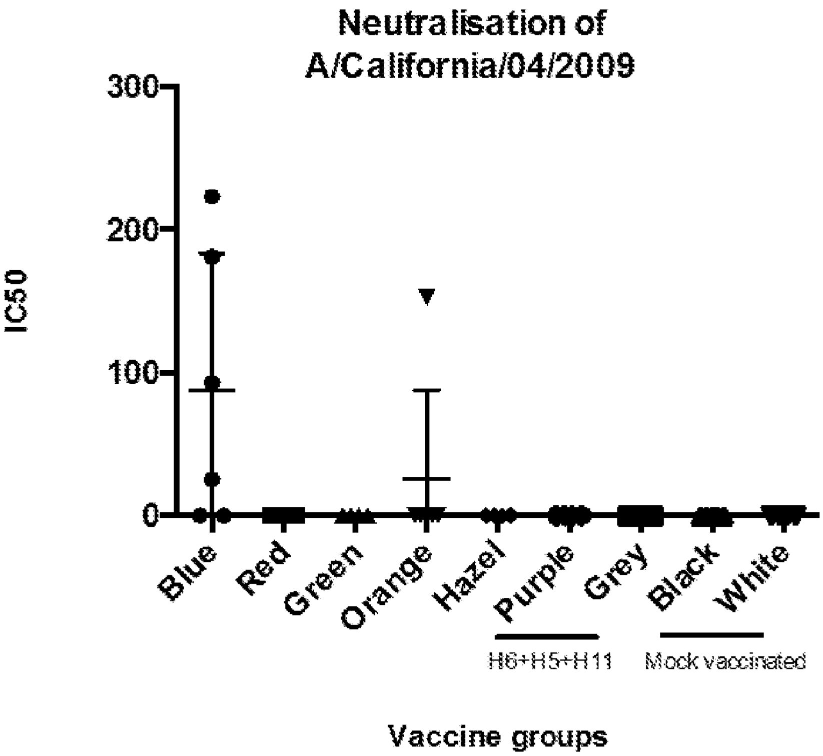
Figure 6C:
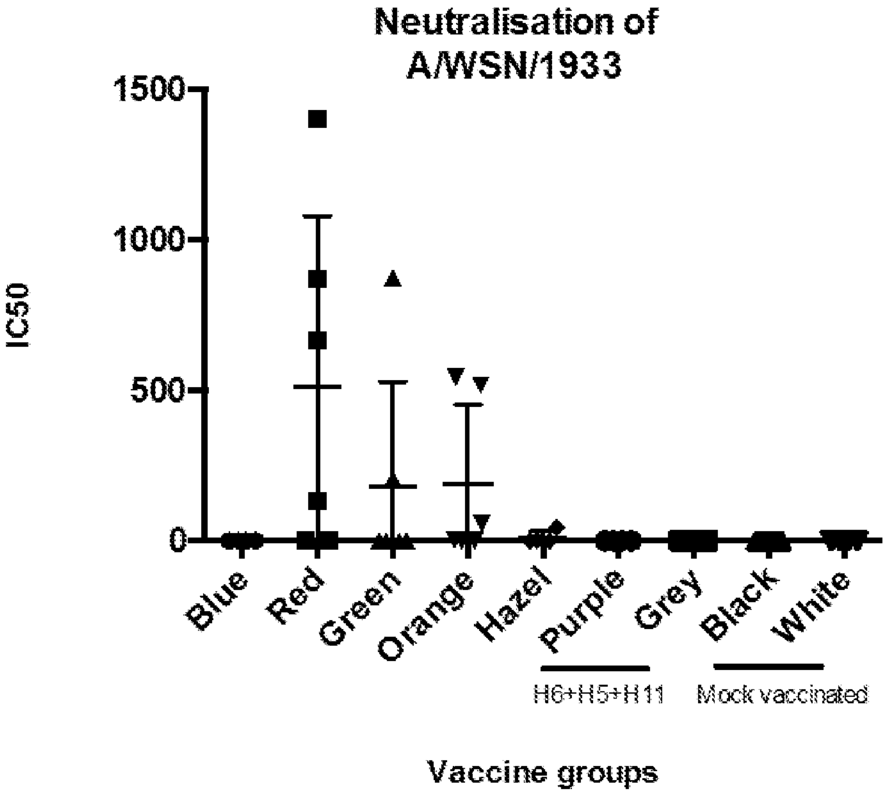
Figure 6D:
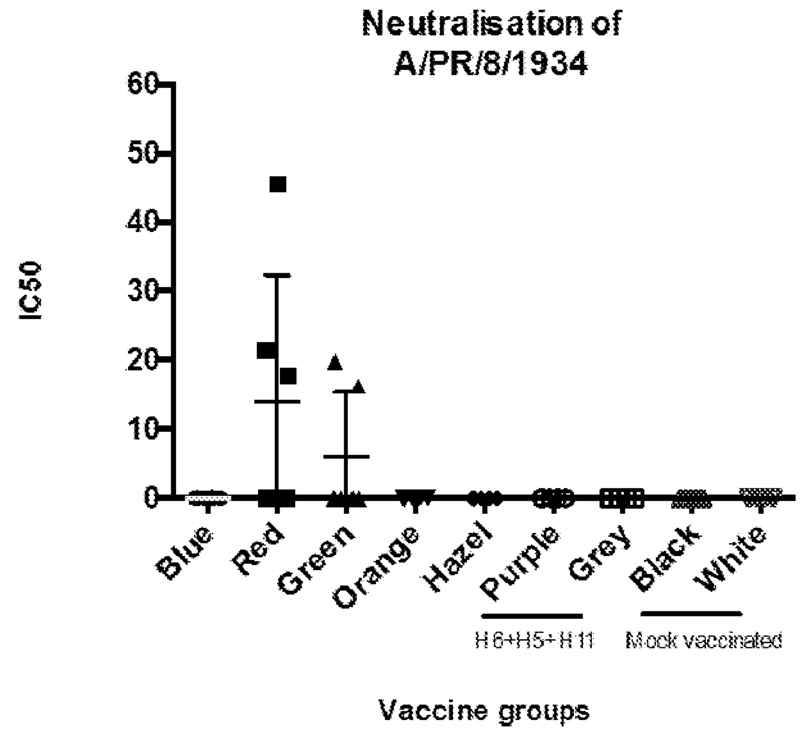
Figure 6E:
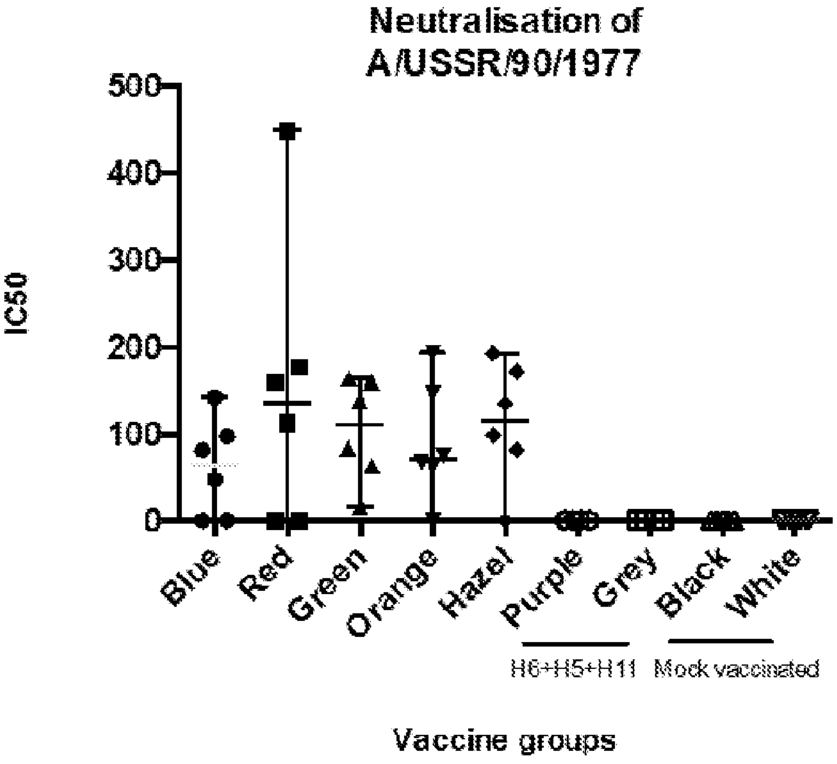
Figure 6F:
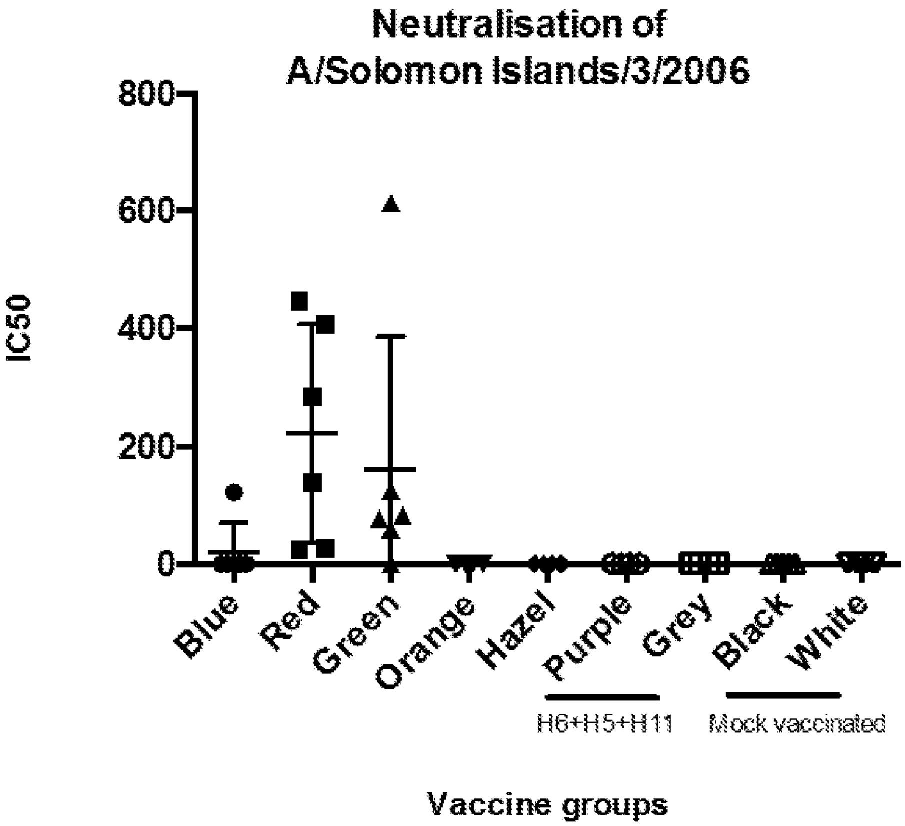
Figure 6G:
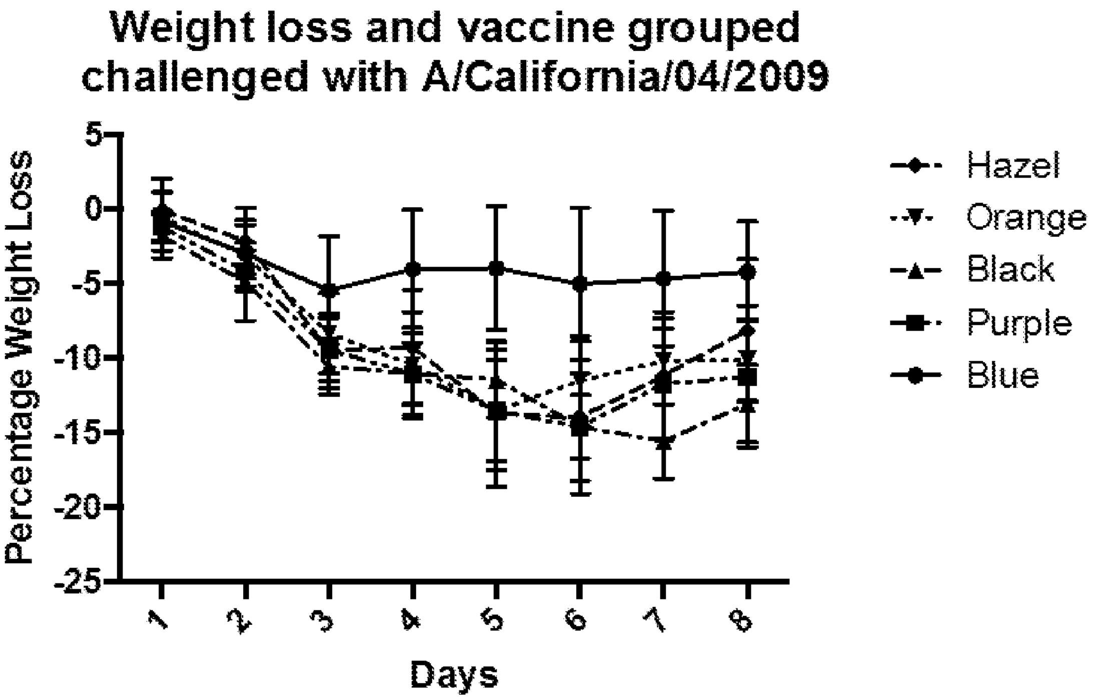
Figure 6H:
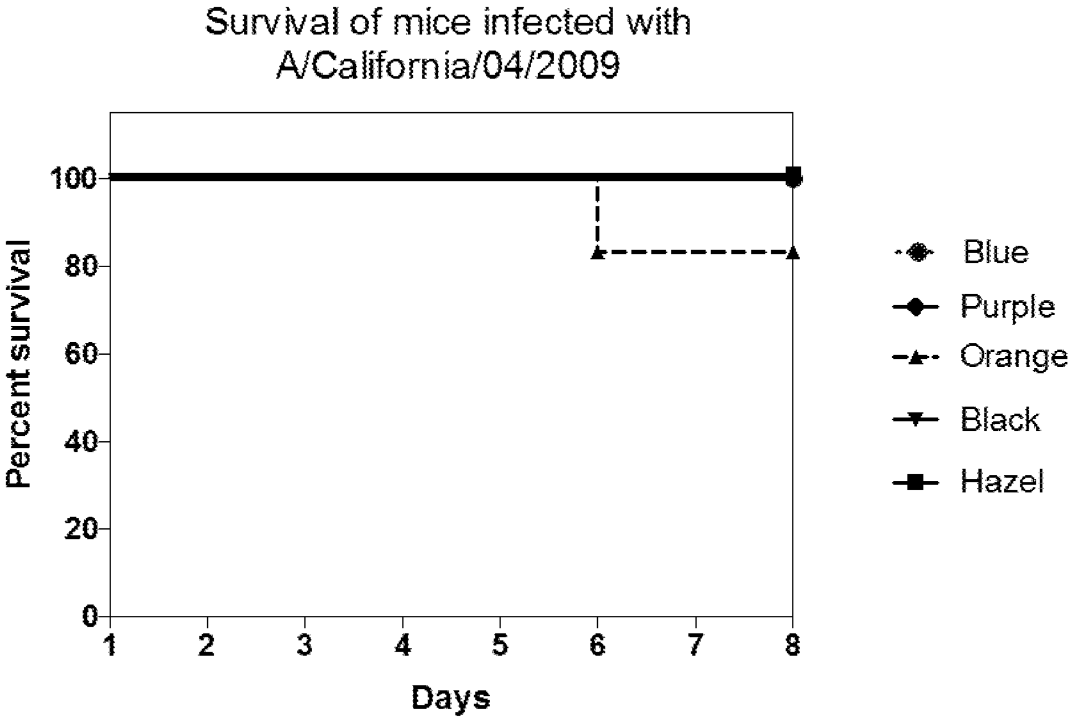
Figure 6I:
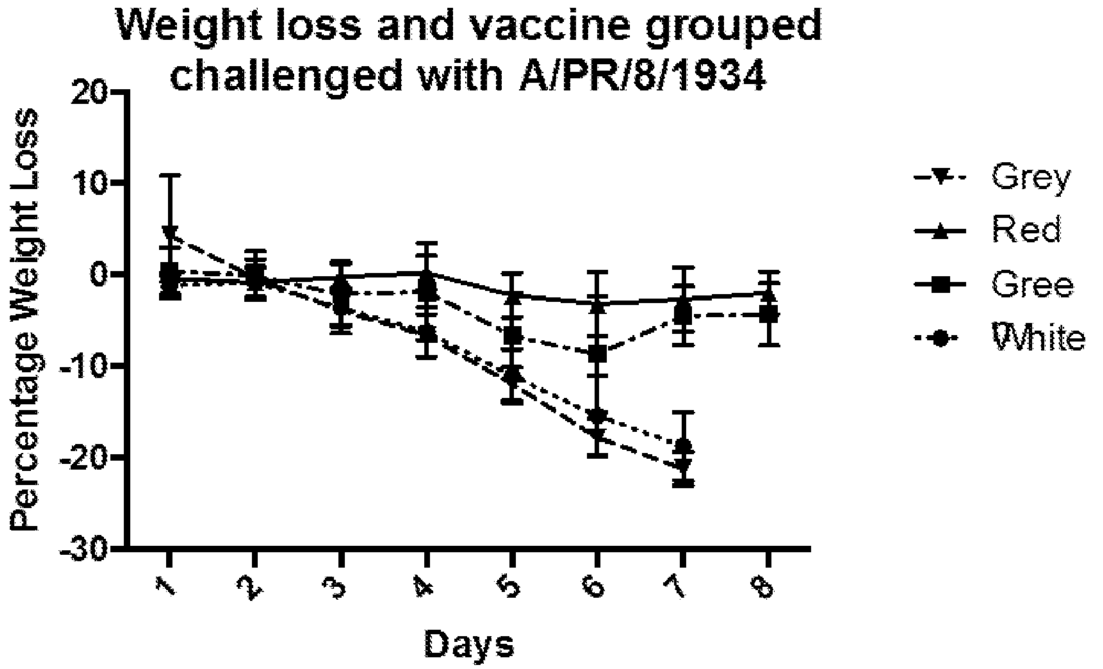
Figure 6J:
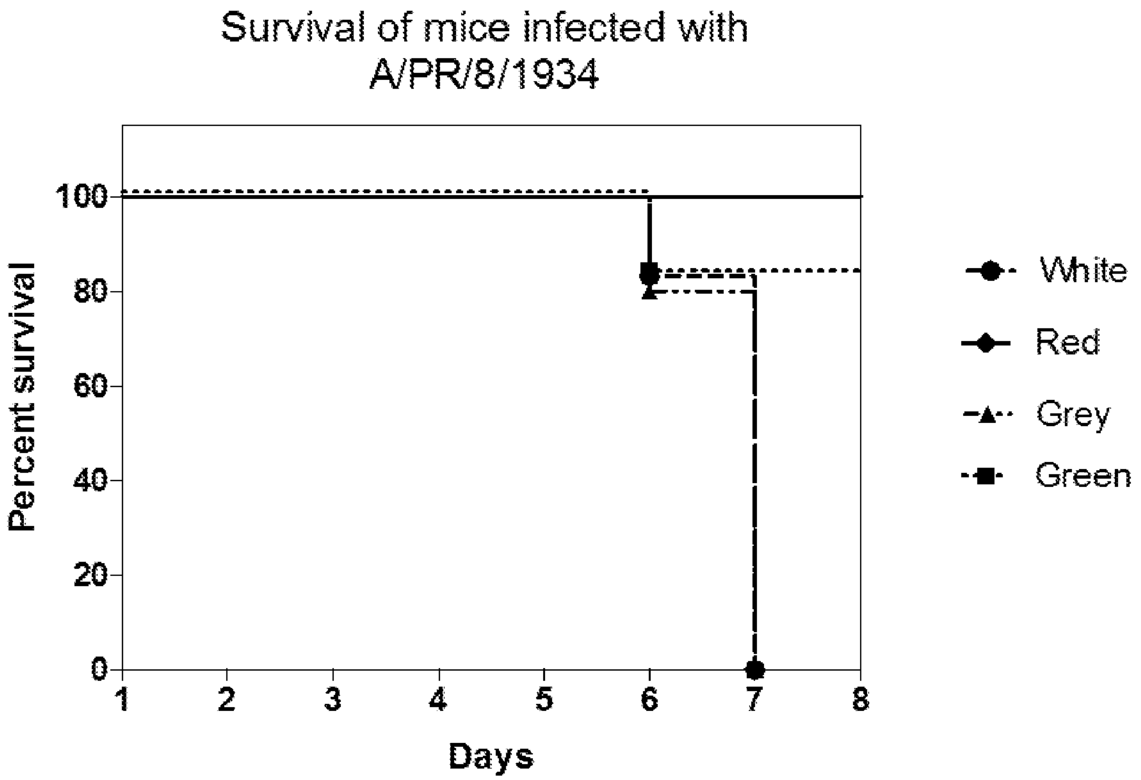
Figure 7A:
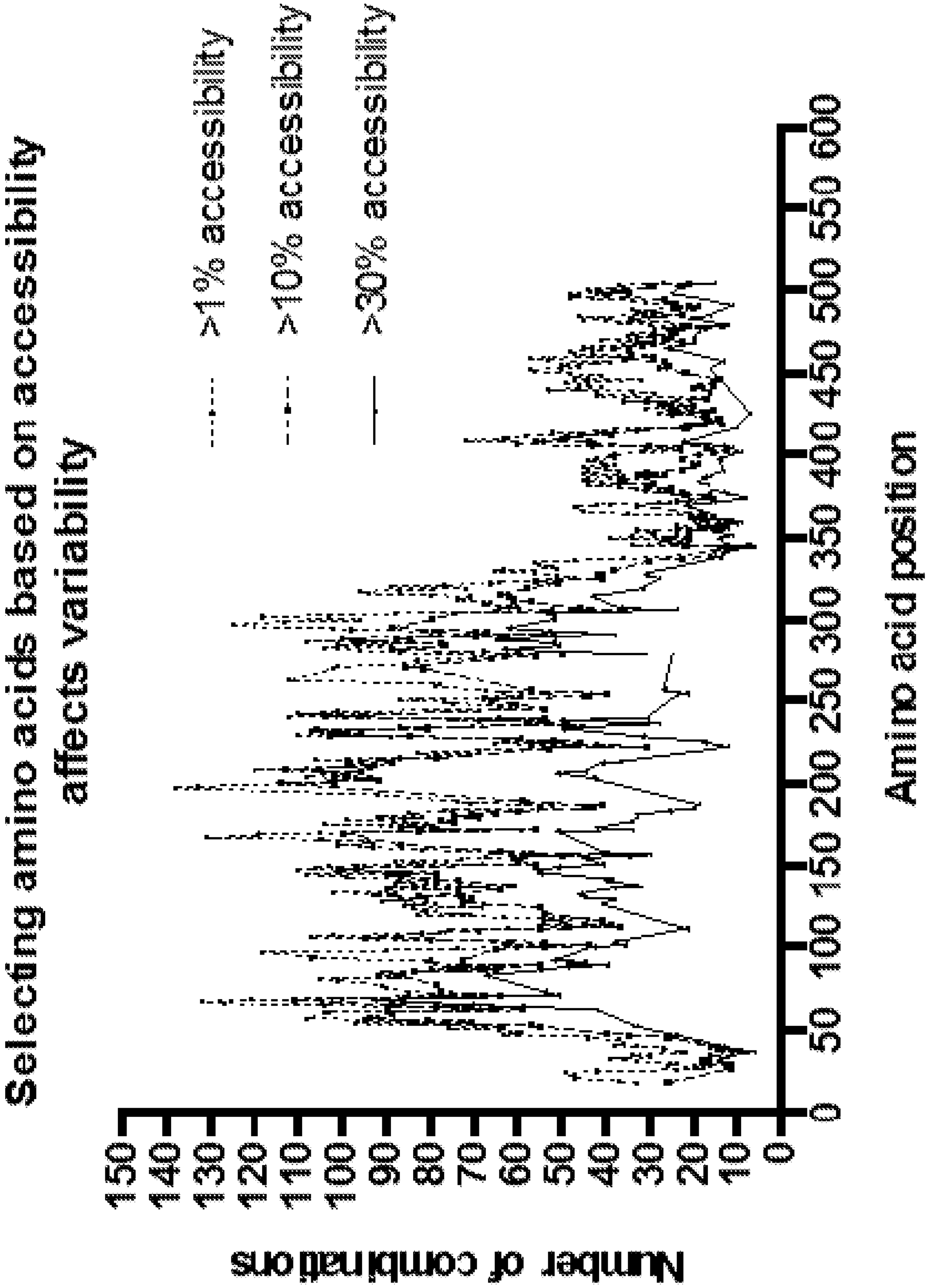
Figure 7B:
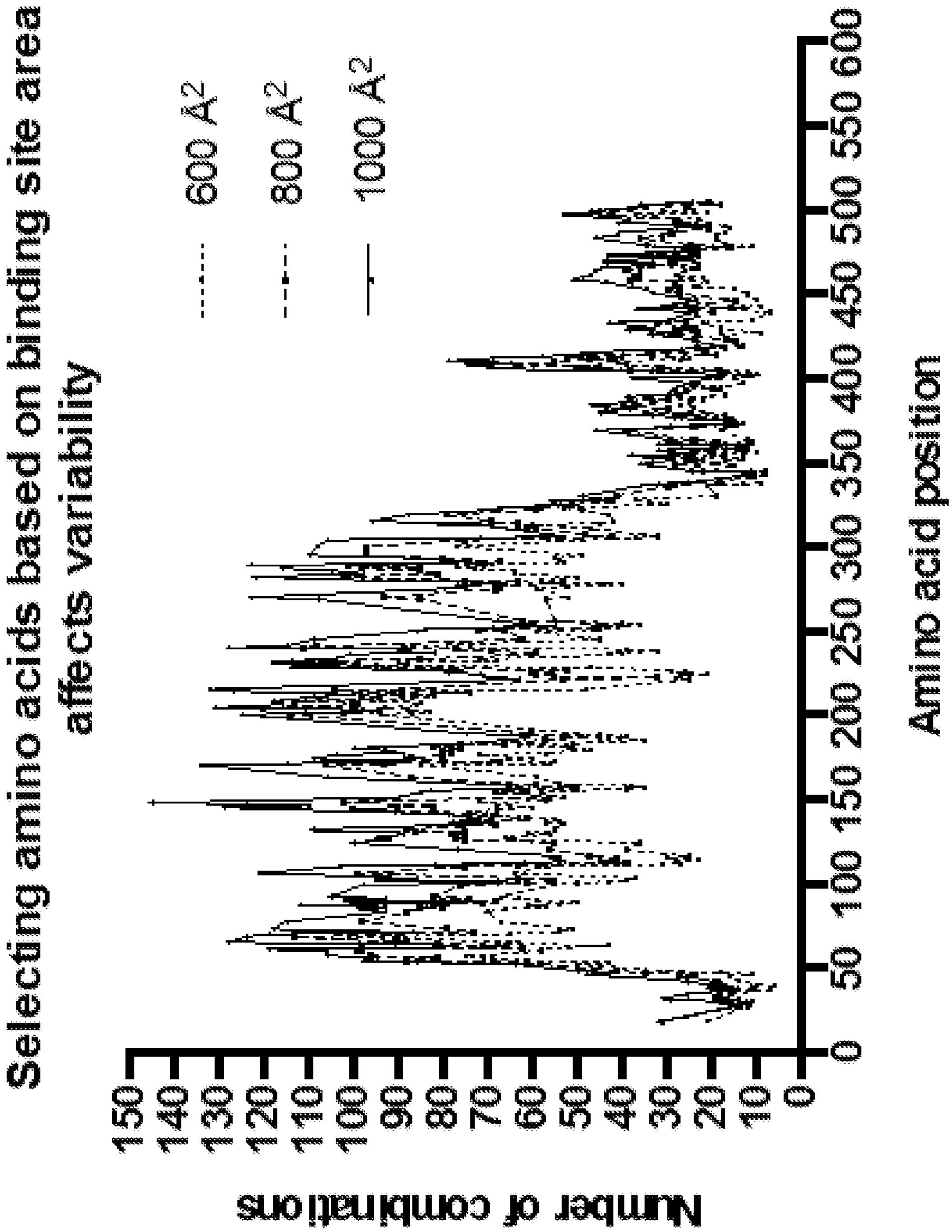
Figure 7C:
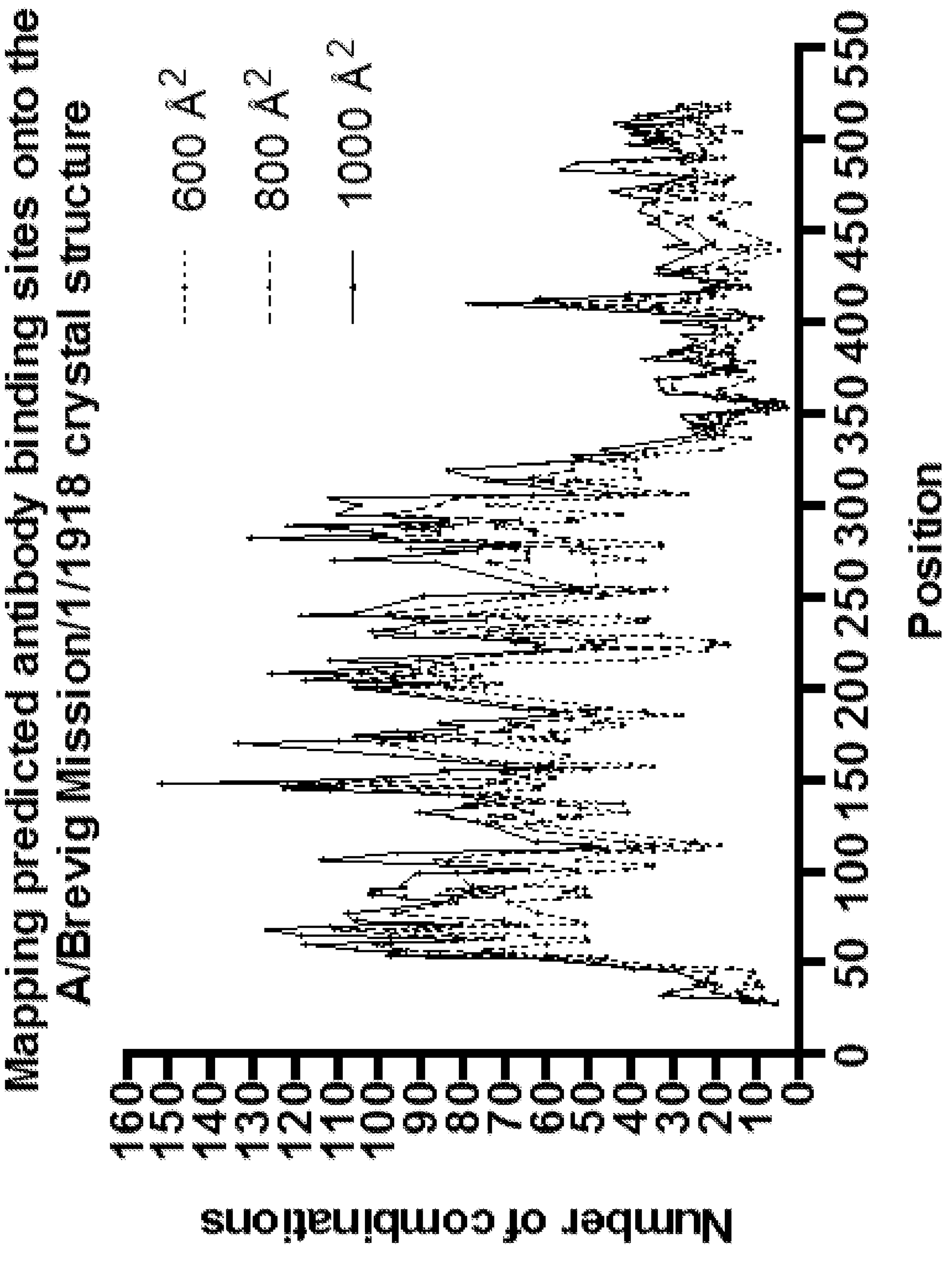
Figure 7D:
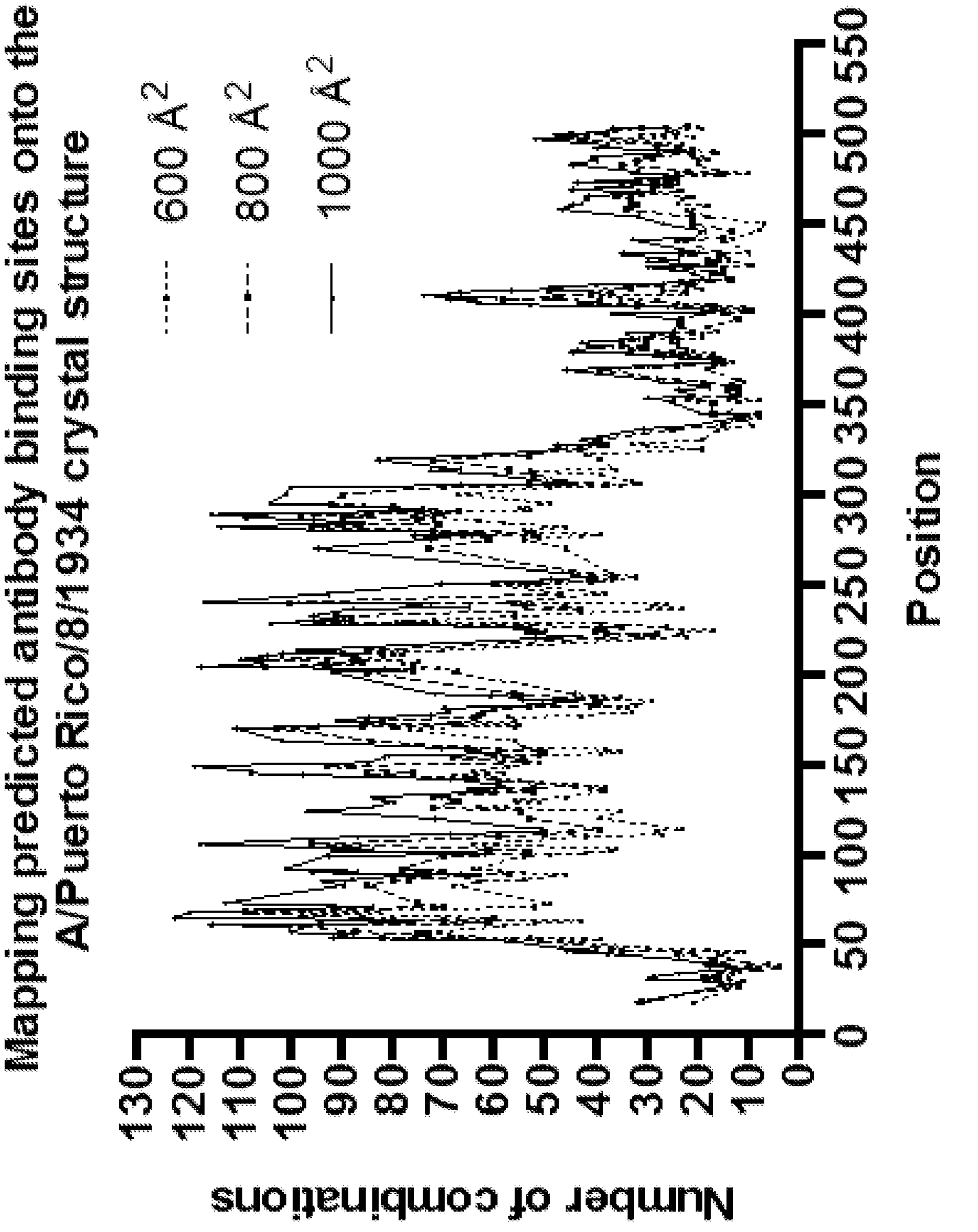
Figure 7E:
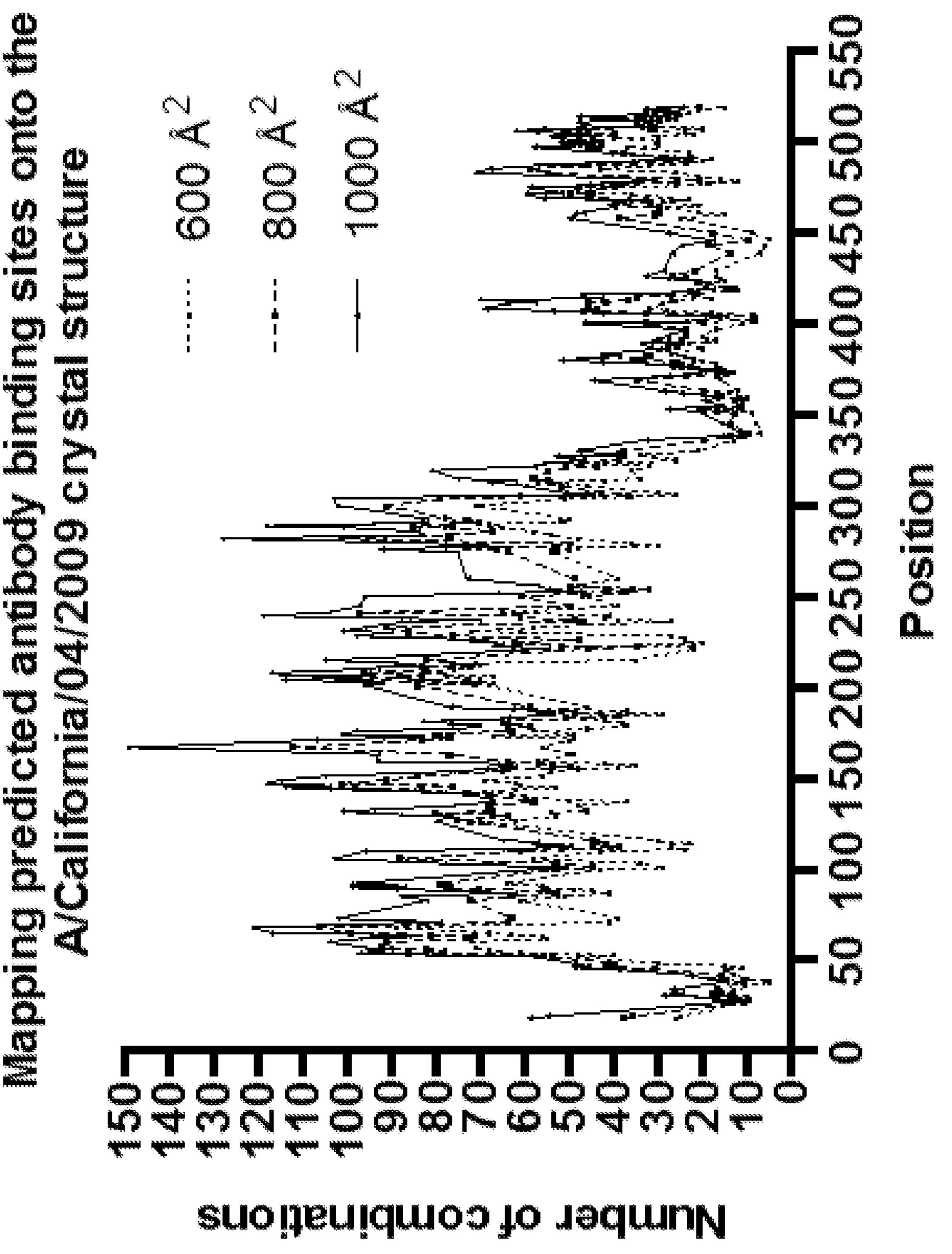
Figure 7F:
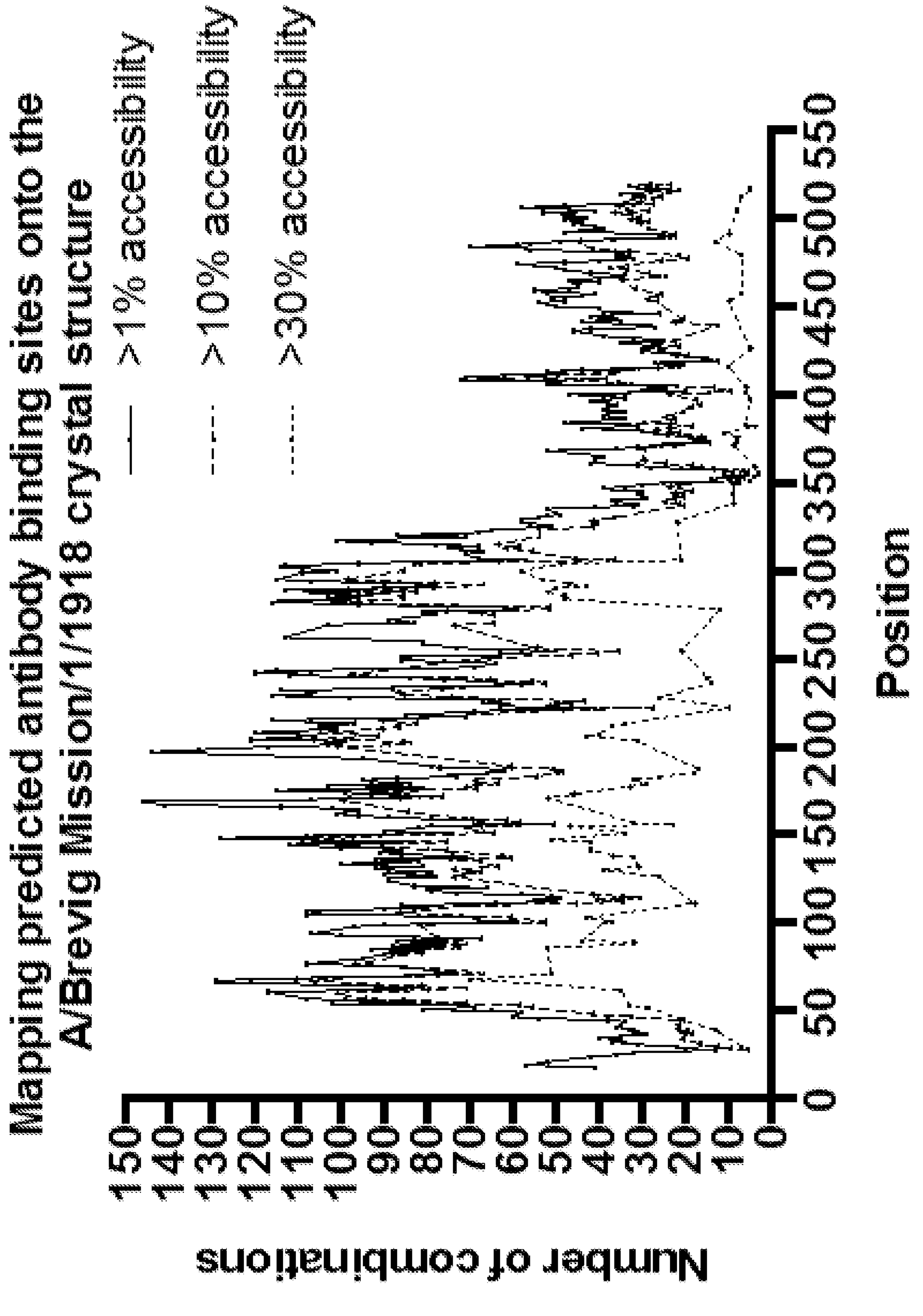
Figure 7G:
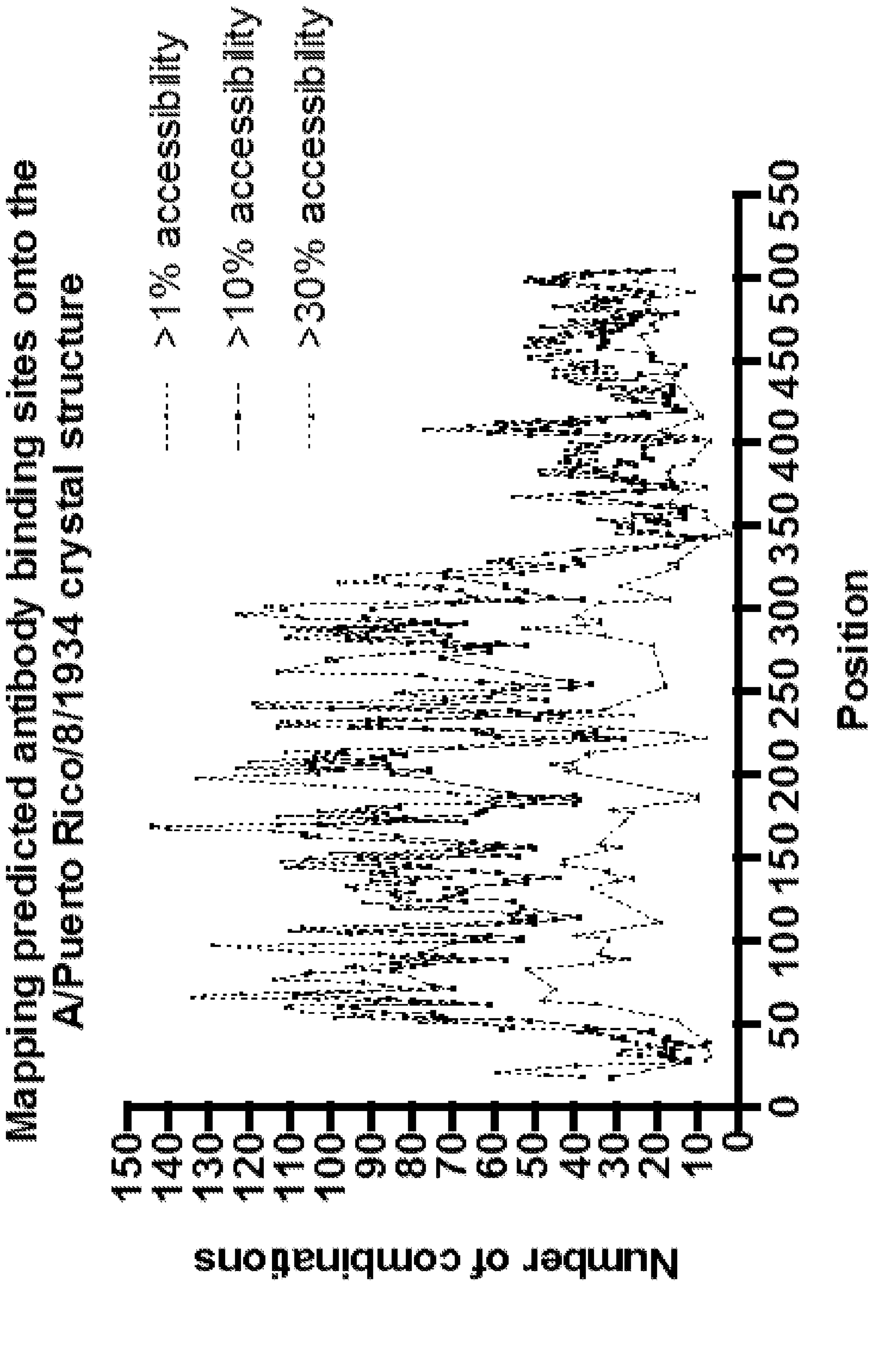
Figure 7H:
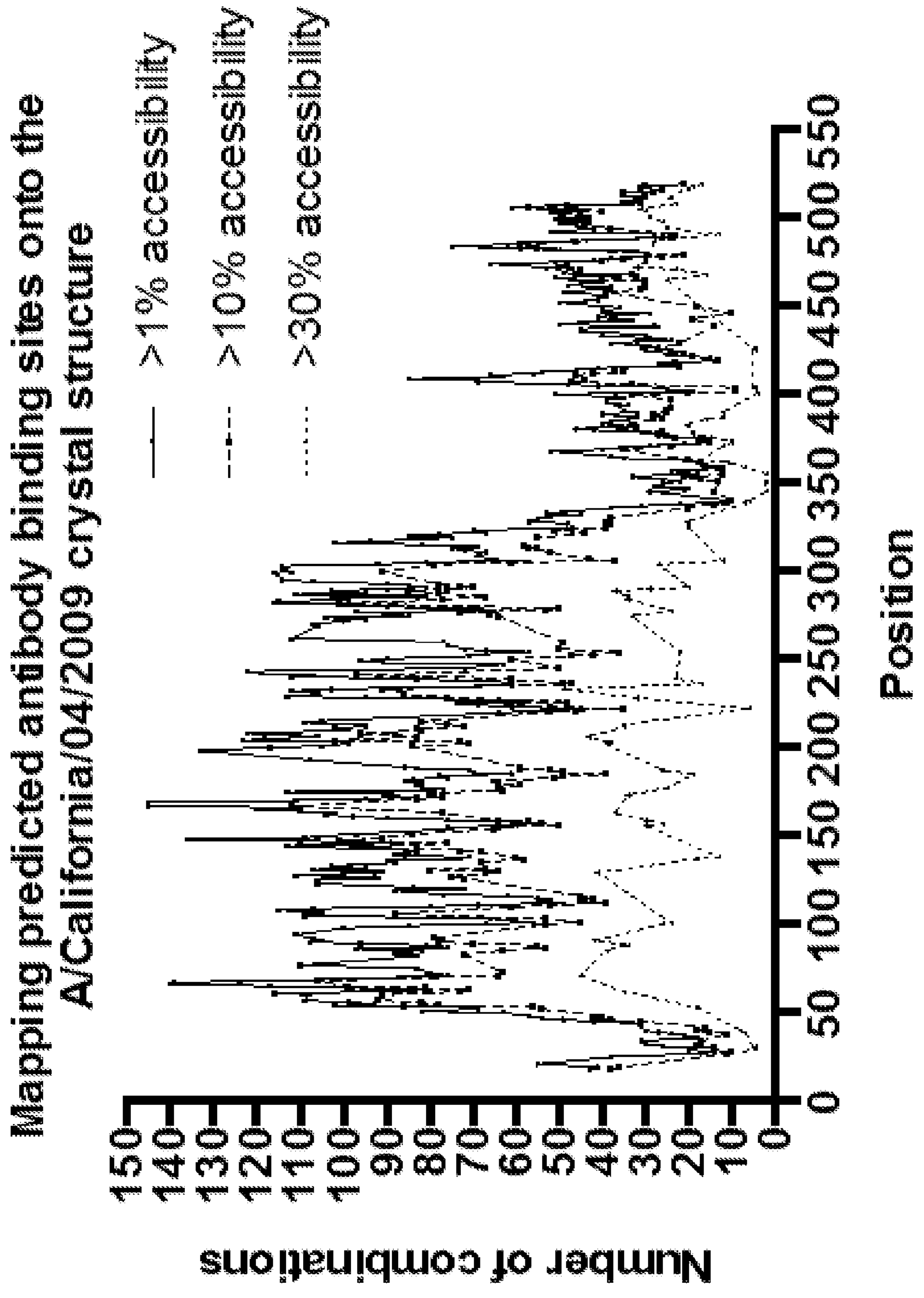
Figure 7I:
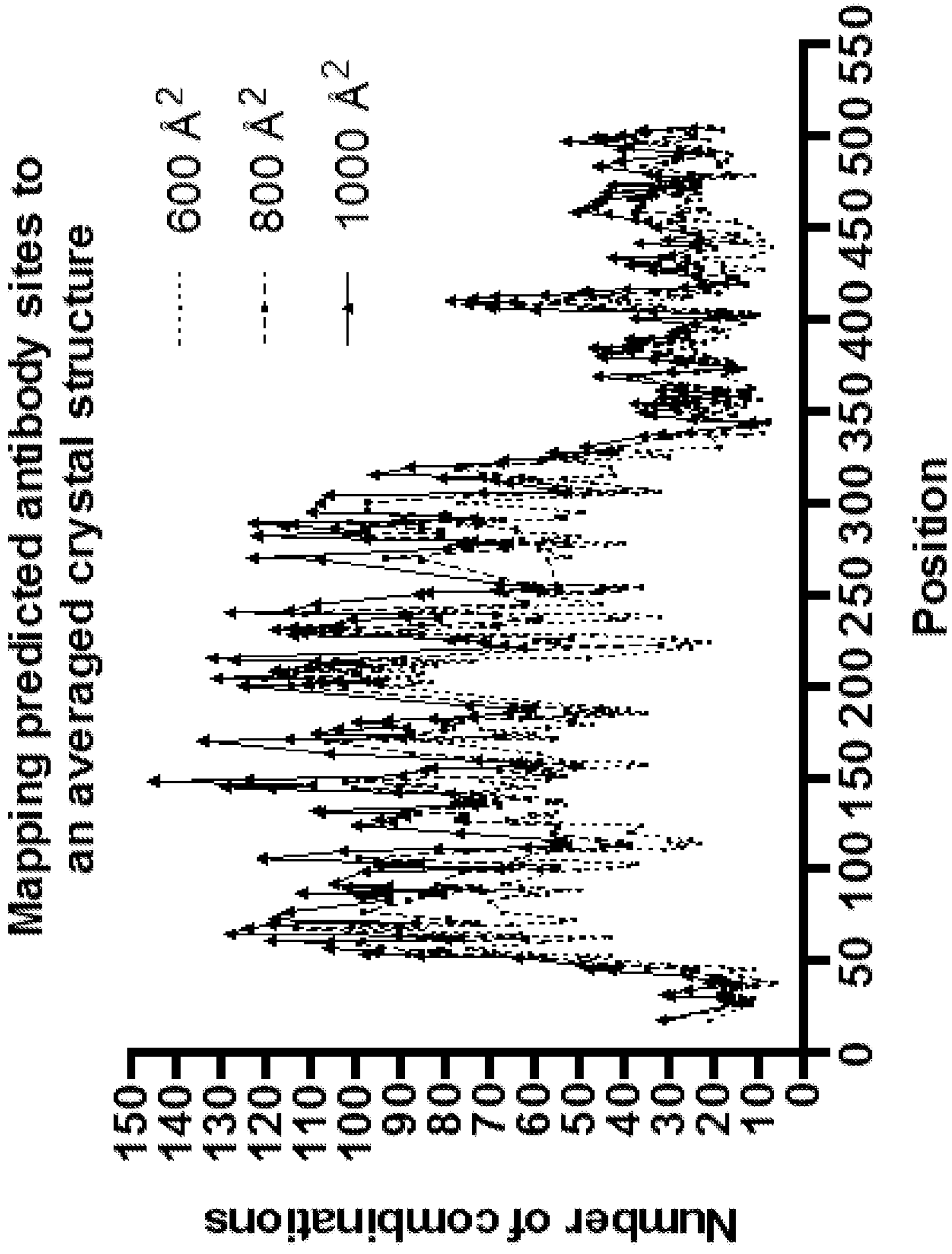
Figure 7J:
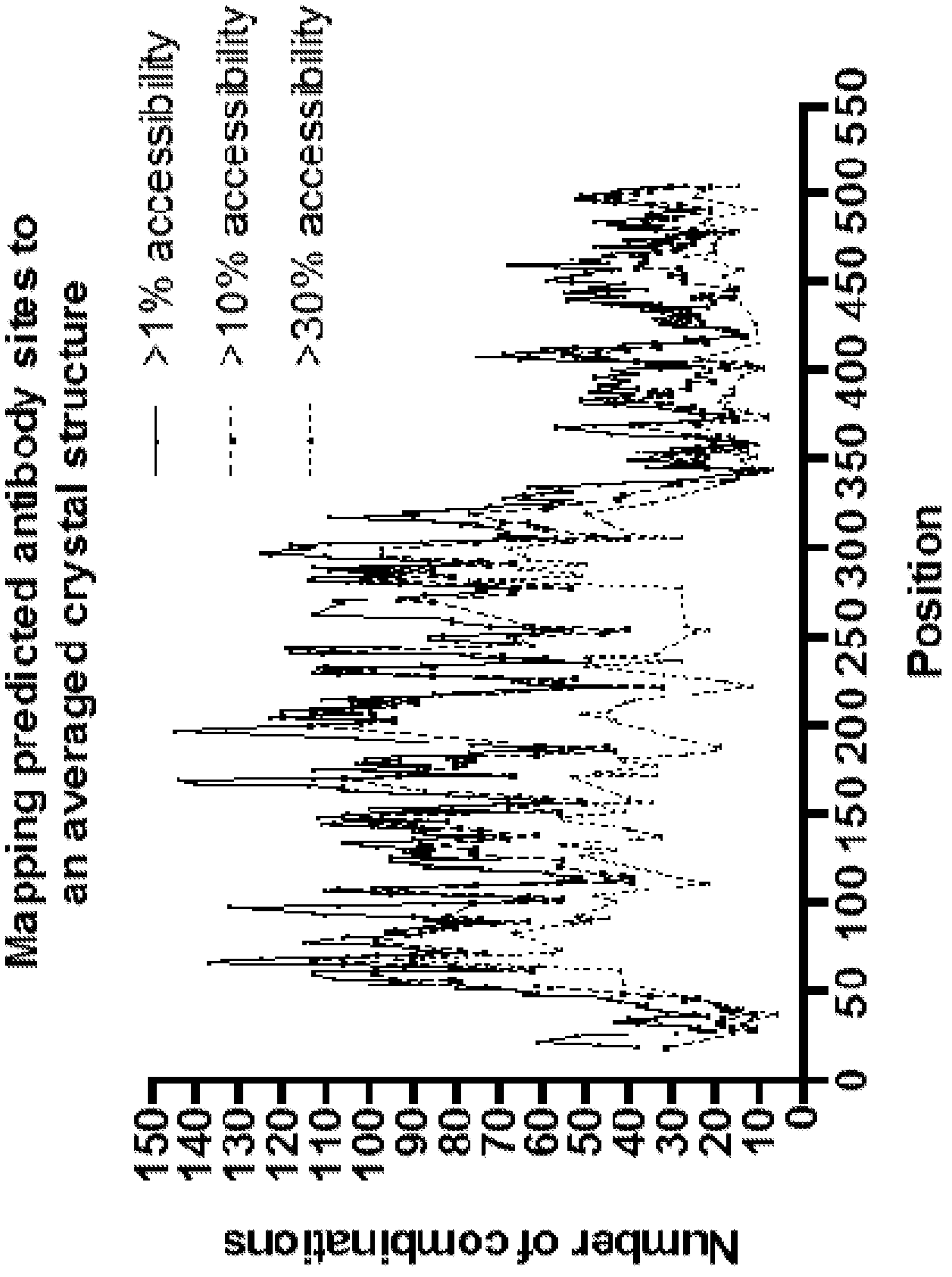

The basic vaccination protocol is shown in FIG. 6A.

Mice were sequentially vaccinated with the sequences outlined below:

| | Position | | | | | | | | | | | |
|---|---|---|---|---|---|---|---|---|---|---|---|---|
| Name | 146 | 147 | 148 | 149 | 151 | 154 | 155 | 156 | 157 | 158 | 159 | 163 |
| Blue | N | K | G | V | A | P | H | A | G | A | K | K |
| Hazel | N | I | G | V | A | S | H | A | G | K | S | K |
| Green | T | R | G | V | A | S | H | K | G | K | S | R |
| Orange | T | K | G | V | A | S | H | N | G | K | S | R |
| Red | T | Absent | G | V | A | S | H | N | G | K | S | R |

Five groups of six mice (named blue, red, hazel, orange and green) were vaccinated via intramuscular injection of 100 μg of DNA each with a different conformation of the epitope substituted into H6 HA at 10 weeks. At 13 weeks of age, the same groups were vaccinated via intramuscular injection of 100 μg of DNA with the same conformation substituted into H5 HA. At 18 weeks of age, the same groups were vaccinated via intramuscular with the same conformation substituted into H11 HA displayed on a lentivirus and mixed with Alum adjuvant (Alhydrogel, Invivogen). Two control groups (purple and grey) were vaccinated in the same manner as the aforementioned mice with the HAs without the epitope conformations substituted into them. Finally, two further control groups (black and white) were mock vaccinated at 18 weeks with PBS and Alum (Alhydrogel, Invivogen). At 11 weeks, 14 weeks, 20 weeks and 21 weeks all groups were bled. At 22 weeks, the blue, orange, hazel and purple groups were challenged with mouse adapted A/California/4/2009 virus and weighed daily. At 22 weeks, the red, green, grey and white groups were challenged with mouse adapted A/PR/8/1934 virus and weighed daily. The results are shown in FIG. 6.

Example 8: Vaccination Against the H3 Influenza Subtype

The method of identifying sites of limited variability and subsequent epitopes of limited variability is applied to the H3 subtype of influenza A. As H3 subtype influenza A virus evolves in a similar way to the H1 subtype influenza A virus, this approach to identifying epitopes is equally applicable to H3 subtype influenza A. Consequently epitopes can be identified by mapping the variability of H3 strains to the head of H3 influenza, identifying regions of limited variability, mapping said regions to H3 structures to identify potential epitopes and then analysing consensus sequence data to identify epitopes behaving in a cyclical manner predicted by antigenic thrift model Epitope conformations of this type are placed in the HA head domains of H4, H7 H10, H14 and H15 and expressed using VLPs or viral vectors. The vaccine combination is administered as a prime-boost-boost.

Example 9: Cross-Reactivity Produced by the Vaccines

ELISA assays were performed against the HA1 domain of A/PR/8/1934, A/Bel/1942, A/Albany/14/1951 and A/Memphis/3/1987. Relative ELISA units (REU) were calculated based on a known positive sample reaching an OD of 1.0 in each assay.

| | HA1 domains (REU) | | | |
|---|---|---|---|---|
| Vaccine groups (pooled sera samples) | A/PR/8/ 1934 | A/Bel/1942 | A/Albany/ 14/1951 | A/Memphis/ 3/1987 |
| Blue | — | — | — | — |
| Hazel | — | — | — | 329 |
| Green | 205 | — | — | 565 |
| Orange | 231 | 224 | 317 | 735 |
| Red | 770 | — | — | 307 |
| H5 + H6 + H11 control | — | — | — | — |
| Unvaccinated control | — | — | — | — |

REFERENCES

Belongia, E. A. et al., 2009. Effectiveness of Inactivated Influenza Vaccines Varied Substantially with Antigenic Match from the 2004-2005 Season to the 2006-2007 Season Linked references are available on JSTOR for this article: Effectiveness of Inactivated Influenza Vaccines Varied. The Journal of Infectious Disease, 199(2), pp. 159-167.

Carnell et al., (2015) Pseudotype-based neutralization assays for influenza: a systematic analysis. Front Immunol. 2015 Apr. 29; 6:161. doi: 10.3389/fimmu.2015.00161. eCollection 2015.

Carter et al., (2013) Sequential seasonal H1N1 influenza virus infections protect ferrets against novel 2009 H1N1 influenza virus. J Virol. 2013 February; 87(3):1400-10.

Caton et al., 1982. The antigenic structure of the influenza virus A/PR/8/34 hemagglutinin (H1 subtype). Cell, 31(2 Pt 1), pp. 417-427.

Gupta S. 2016 Immune Driven Pathogen Evolution, Encyclopaedia of Immunology (Ed. Kaye, P.) Elsevier.

Krammer, F. et al., 2013. Broadly Protective Stalk-Specific Antibodies., 87(12), pp. 6542-6550.

Li, Y. et al., 2013. Immune history shapes specificity of pandemic H1N1 influenza antibody responses. 210(8), pp. 1493-1500.

Lozano, R. et al., 2012. Global and regional mortality from 235 causes of death for 20 age groups in 1990 and 2010: a systematic analysis for the Global Burden of Disease Study 2010. Lancet, 380, pp. 2095-2128.

Manicassamy, B. et al., 2010. Protection of mice against lethal challenge with 2009 H1N1 influenza A virus by 1918-like and classical swine H1N1 based vaccines. PLoS Pathogens, 6(1).

Matsuzaki, Y. et al., 2014. Epitope Mapping of the Hemagglutinin Molecule of A/(H1N1) pdm09 Influenza Virus by Using Monoclonal Antibody Escape Mutants. Journal of Virology, 88(21), pp. 12364-12373.

Mertz, D., Hyong, T. & Johnstone, J., 2013. Populations at risk for severe or complicated influenza illness: systematic review and meta-analysis. British Medical Journal, 5061(August), pp. 1-15.

Miura et al. 2008 Vaccine 26:193.

Presanis, A. M. et al., 2011. Changes in severity of 2009 pandemic A/H1N1 influenza in England: a Bayesian evidence synthesis. British Medical Journal, (343), pp. 1-14.

Recker, M. et al., 2007. The generation of influenza outbreaks by a network of host immune responses against a limited set of antigenic types. PNAS 104:7711

Taubenberger, J. K. & Morens, D. M., 2006.1918 Influenza: the Mother of All Pandemics. Lancet, 12(1), pp. 15-22.

Treanor, J. J. et al., 2012. Effectiveness of Seasonal Influenza Vaccines in the United States During a Season With Circulation of All Three Vaccine Strains., pp. 1-9.

WHO 2016. Recommended composition of influenza virus vaccines for use in the 2016-2017 northern hemisphere influenza season.

Wikramaratna, P. S. et al., 2013. The antigenic evolution of influenza: drift or thrift? Philosophical transactions of the Royal Society of London. Series B, Biological sciences, 368(1614), p. 20120200.

```
SEQUENCES
H1 head domain-amino acid
                                                        SEQ ID NO: 1
CKLRGVAPLHLGKCNIAGWILGNPECESLSTASSWSYIVETSSSDNGTCYPGDFIDYEE

LREQLSSVSSFERFEIFPKTSSWPNHDSNKGVTAACPHAGAKSFYKNLIWLVKKGNSY

PKLSKSYINDKGKEVLVLWGIHHPSTSADQQSLYQNADAYVFVGTSRYSKKFKPEIAIR

PKVRDQEGRMNYYWTLVEPGDKITFEATGNLVVPRYAFAMERNAGSGIIISDTPVHDC

H6 head domain-amino acid
                                                        SEQ ID NO: 2
CKILNKAPLDLRGCTIEGWILGNPQCDLLLGDQSWSYIVERPTAQNGICYPGTLNEVEE

LKALIGSGERVERFEMFPKSTWAGVDTNSGVTSACPYNSGSSFYRNLLWIIKTKSAAY

PVIKGTYNNTGNQPILYFWGVHHPPDTNEQNTLYGSGDRYVRMGTESMNFAKSPEIA

ARPAVNGQRGRIDYYWSVLKPGETLNVESNGNLIAPVVYAYKFVSTNNKGAVFKSNLPI

ENC
```

-continued

H5 head domain-amino acid

SEQ ID NO: 3

CDLDGVKPLILRDCSVAGWLLGNPMCDEFLNVPEWSYIVEKANPANDLCYPGNFNDYE

ELKHLLSRINHFEKIQIIPKSSWSDHEASSGVSSACPYQGRSSFFRNVVWLIKKNNAYPTI

KRSYNNTNQEDLLVLWGIHHPNDAAEQTKLYQNPTTYISVGTSTLNQRLVPKIATRSKV

NGQSGRMEFFWTILKPNDAINFESNGNFIAPEYAYKIVKKGDSTIMKSELEYGNC

H11 head domain-amino acid

SEQ ID NO: 4

CSIDGKAPISLGDCSFAGWILGNPMCDDLIGKTSWSYIVEKPNPTNGICYPGTLENEEE

LRLKFSGVLEFSKFEAFTSNGWGAVNSGAGVTAACKFGSSNSFFRNMVWLIHQSGTY

PVIRRTFNNTKGRDVLMVWGVHHPATLKEHQDLYKKDSSYVAVGSESYNRRFTPEIST

RPKVNGQAGRMTFYVVTIVKPGEAITFESNGAFLAPRYAFELVSLGNGKLFRSDLNIESC

H1 head domain-nucleotide

SEQ ID NO: 5

TGCAAGCTGAGGGGCGTGGCCCCCCTGCACCTGGGCAAGTGCAACATCGCCGGCTGGATC

CTGGGCAACCCCGAGTGCGAGAGCCTGAGCACCGCCAGCAGCTGGAGCTACATCGTGGAG

ACCAGCAGCAGCGACAACGGCACCTGCTACCCCGGCGACTTCATCGACTACGAGGAGCTG

AGGGAGCAGCTGAGCAGCGTGAGCAGCTTCGAGAGGTTCGAGATCTTCCCCAAGACCAGC

AGCTGGCCCAACCACGACAGCAACAAGGGCGTGACCGCCGCCTGCCCCCACGCCGGCGCC

AAGAGCTTCTACAAGAACCTGATCTGGCTGGTGAAGAAGGGCAACAGCTACCCCAAGCTG

AGCAAGAGCTACATCAACGACAAGGGCAAGGAGGTGCTGGTGCTGTGGGGCATCCACCAC

CCCAGCACCAGCGCCGACCAGCAGAGCCTGTACCAGAACGCCGACGCCTACGTGTTCGTG

GGCACCAGCAGGTACAGCAAGAAGTTCAAGCCCGAGATCGCCATCAGGCCCAAGGTGAGG

GACCAGGAGGGCAGGATGAACTACTACTGGACCCTGGTGGAGCCCGGCGACAAGATCACC

TTCGAGGCCACCGGCAACCTGGTGGTGCCCAGGTACGCCTTCGCCATGGAGAGGAACGCC

GGCAGCGGCATCATCATCAGCGACACCCCCGTGCACGACTGC

H6 head domain-nucleotide

SEQ ID NO: 6

TGCAAGATCCTGAACAAGGCCCCCCTGGACCTGAGGGGCTGCACCATCGAGGGCTGGATC

CTGGGCAACCCCCAGTGCGACCTGCTGCTGGGCGACCAGAGCTGGAGCTACATCGTGGAG

AGGCCCACCGCCCAGAACGGCATCTGCTACCCCGGCACCCTGAACGAGGTGGAGGAGCTG

AAGGCCCTGATCGGCAGCGGCGAGAGGGTGGAGAGGTTCGAGATGTTCCCCAAGAGCACC

TGGGCCGGCGTGGACACCAACAGCGGCGTGACCAGCGCCTGCCCCTACAACAGCGGCAGC

AGCTTCTACAGGAACCTGCTGTGGATCATCAAGACCAAGAGCGCCGCCTACCCCGTGATC

AAGGGCACCTACAACAACACCGGCAACCAGCCCATCCTGTACTTCTGGGGCGTGCACCAC

CCCCCCGACACCAACGAGCAGAACACCCTGTACGGCAGCGGCGACAGGTACGTGAGGATG

GGCACCGAGAGCATGAACTTCGCCAAGAGCCCCGAGATCGCCGCCAGGCCCGCCGTGAAC

GGCCAGAGGGGCAGGATCGACTACTACTGGAGCGTGCTGAAGCCCGGCGAGACCCTGAAC

GTGGAGAGCAACGGCAACCTGATCGCCCCCTGGTACGCCTACAAGTTCGTGAGCACCAAC

AACAAGGGCGCCGTGTTCAAGAGCAACCTGCCCATCGAGAACTGC

H5 head domain-nucleotide

SEQ ID NO: 7

TGCGACCTGGACGGCGTGAAGCCCCTGATCCTGAGGGACTGCAGCGTGGCCGGCTGGCTG

CTGGGCAACCCCATGTGCGACGAGTTCCTGAACGTGCCCGAGTGGAGCTACATCGTGGAG

AAGGCCAACCCCGCCAACGACCTGTGCTACCCCGGCAACTTCAACGACTACGAGGAGCTG

-continued

AAGCACCTGCTGAGCAGGATCAACCACTTCGAGAAGATCCAGATCATCCCCAAGAGCAGC

TGGAGCGACCACGAGGCCAGCAGCGGCGTGAGCAGCGCCTGCCCCTACCAGGGCAGGAGC

AGCTTCTTCAGGAACGTGGTGTGGCTGATCAAGAAGAACAACGCCTACCCCACCATCAAG

AGGAGCTACAACAACACCAACCAGGAGGACCTGCTGGTGCTGTGGGGCATCCACCACCCC

AACGACGCCGCCGAGCAGACCAAGCTGTACCAGAACCCCACCACCTACATCAGCGTGGGC

ACCAGCACCCTGAACCAGAGGCTGGTGCCCAAGATCGCCACCAGGAGCAAGGTGAACGGC

CAGAGCGGCAGGATGGAGTTCTTCTGGACCATCCTGAAGCCCAACGACGCCATCAACTTC

GAGAGCAACGGCAACTTCATCGCCCCCGAGTACGCCTACAAGATCGTGAAGAAGGGCGAC

AGCACCATCATGAAGAGCGAGCTGGAGTACGGCAACTGC

H11 head domain-nucleotide

SEQ ID NO: 8

TGCAGCATCGACGGCAAGGCCCCCATCAGCCTGGGCGACTGCAGCTTCGCCGGCTGGATC

CTGGGCAACCCCATGTGCGACGACCTGATCGGCAAGACCAGCTGGAGCTACATCGTGGAG

AAGCCCAACCCCACCAACGGCATCTGCTACCCCGGCACCCTGGAGAACGAGGAGGAGCTG

AGGCTGAAGTTCAGCGGCGTGCTGGAGTTCAGCAAGTTCGAGGCCTTCACCAGCAACGGC

TGGGGCGCCGTGAACAGCGGCGCCGGCGTGACCGCCGCCTGCAAGTTCGGCAGCAGCAAC

AGCTTCTTCAGGAACATGGTGTGGCTGATCCACCAGAGCGGCACCTACCCCGTGATCAGG

AGGACCTTCAACAACACCAAGGGCAGGGACGTGCTGATGGTGTGGGGCGTGCACCACCCC

GCCACCCTGAAGGAGCACCAGGACCTGTACAAGAAGGACAGCAGCTACGTGGCCGTGGGC

AGCGAGAGCTACAACAGGAGGTTCACCCCCGAGATCAGCACCAGGCCCAAGGTGAACGGC

CAGGCCGGCAGGATGACCTTCTACTGGACCATCGTGAAGCCCGGCGAGGCCATCACCTTC

GAGAGCAACGGCGCCTTCCTGGCCCCCAGGTACGCCTTCGAGCTGGTGAGCCTGGGCAAC

GGCAAGCTGTTCAGGAGCGACCTGAACATCGAGAGCTGC

H1 haemagglutinin-amino acid

SEQ ID NO: 9

MKAILVVLLYTFATANADTLCIGYHANNSTDTVDTVLEKNVTVTHSVNLLEDKHNGKLC

KLRGVAPLHLGKCNIAGWILGNPECESLSTASSWSYIVETSSSDNGTCYPGDFIDYEEL

REQLSSVSSFERFEIFPKTSSWPNHDSNKGVTAACPHAGAKSFYKNLIWLVKKGNSYP

KLSKSYINDKGKEVLVLWGIHHPSTSADQQSLYQNADAYVFVGTSRYSKKFKPEIAIR

PKVRDQEGRMNYYWTLVEPGDKITFEATGNLVVPRYAFAMERNAGSGIIISDTPVHDC

NTTCQTPKGAINTSLPFQNIHPITIGKCPKYVKSTKLRLATGLRNVPSIQSRGLFGAIAGF

IEGGVVTGMVDGVVYGYHHQNEQGSGYAADLKSTQNAIDEITNKVNSVIEKMNTQFTAV

GKEFNHLEKRIENLNKKVDDGFLDIVVTYNAELLVLLENERTLDYHDSNVKNLYEKVRS

QLKNNAKEIGNGCFEFYHKCDNTCMESVKNGTYDYPKYSEEAKLNREEIDGVKLESTR

IYQILAIYSTVASSLVLVVSLGAISFWMCSNGSLQCRICI

H6 haemagglutinin-amino acid

SEQ ID NO: 10

MIAIIVIAILAATGKSDKICIGYHANNSTTQVDTILEKNVTVTHSVELLENQKEERFCKILNK

APLDLRGCTIEGWILGNPQCDLLLGDQSWSYIVERPTAQNGICYPGTLNEVEELKALIG

SGERVERFEMFPKSTWAGVDTNSGVTSACPYNSGSSFYRNLLWIIKTKSAAYPVIKGT

YNNTGNQPILYFWGVHHPPDTNEQNTLYGSGDRYVRMGTESMNFAKSPEIAARPAVN

GQRGRIDYYWSVLKPGETLNVESNGNLIAPVVYAYKFVSTNNKGAVFKSNLPIENCDAT

CQTIAGVLRTNKTFQNVSPLWIGECPKYVKSESLRLATGLRNVPQIETRGLFGAIAGFIE

GGVVTGMIDGVVYGYHHENSQGSGYAADRESTQKAIDGITNKVNSIIDKMNTQFEAVDH

-continued

EFSNLERRIDNLNKRMEDGFLDVVVTYNAELLVLLENERTLDLHDANVKNLYEKVKSQL

RDNANDLGNGCFEFWHKCDNECIESVKNGTYDYPKYQDESKLNRQEIESV

KLENLGVYQILAIYSTVSSSLVLVGLIIAMGLWMCSNGSMQCRICI

H5 haemagglutinin-amino acid

SEQ ID NO: 11

MEKIVLLLAIVSLVKSDQICIGYHANNSTEQVDTIMEKNVTVTHAQDILEKTHNGKLCDL

DGVKPLILRDCSVAGWLLGNPMCDEFLNVPEWSYIVEKANPANDLCYPGNFNDYEELK

HLLSRINHFEKIQIIPKSSWSDHEASSGVSSACPYQGRSSFFRNVVWLIKKNNAYPTIKRS

YNNTNQEDLLVLWGIEIHPNDAAEQTKLYQNPTTYISVGTSTLNQRLVPKIATRSKVNGQ

SGRMEFFWTILKPNDAINFESNGNFIAPEYAYKIVKKGDSTIMKSELEYGNCNTKCQTPI

GAINSSMPFHNIEIPLTIGECPKYVKSNRLVLATGLRNSPQRKKRGLFGAIAGFIEGGWQG

MVDGWYGYEIHSNEQGSGYAADKESTQKAIDGVTNKVNSIIDKMNTQFEAVGREENNL

ERRIENLNKKMEDGELDVWTYNAELLVLMENERTLDETIDSNVKNLYDKVRLQLRDNA

KELGNGCFEEYEIRCDNECMESVRNGTYDYPQYSEEARLKREEISGVKLESIGTYQILSIY

STVASSLALAIMVAGLSLWMCSNGSLQCRICI

H11 haemagglutinin-amino acid

SEQ ID NO: 12

MKKTLLFAAIIICIQADEICIGYLSNNSTEKVDTIIESNVTVTSSVELVENEHTGSFCSIDGK

APISLGDCSFAGWILGNPMCDDLIGKTSWSYIVEKPNPTNGICYPGTLENEEELRLKFS

GVLEFSKFEAFTSNGWGAVNSGAGVTAACKFGSSNSFFRNMVWLIHQSGTYPVIRRT

FNNTKGRDVLMVWGVHHPATLKEHQDLYKKDSSYVAVGSESYNRRFTPEISTRPKVN

GQAGRMTFYVVTIVKPGEAITFESNGAFLAPRYAFELVSLGNGKLFRSDLNIESCSTKCQ

SEIGGINTNRSFHNVHRNTIGDCPKYVNVKSLKLATGLRNVPAIATRGLFGAIAGFIEGG

WPGLINGVVYGFQHRNEEGTGIAADKESTQKAIDQITSKVNNIVDRMNTNFESVQHEFS

EIEERINQLSKHVDDSVIDIWSYNAQLLVLLENEKTLDLHDSNVRNLHEKVRRMLKDNA

KDEGNGCFTFYHKCDNECIEKVRNGTYDHKEFEEESKLNRQEIEGVKLDSNGNVYKIL

SIYSCIASSLVLAAIIMGFILWACSNGSCRCTICI

Head domain (blue)-amino acid BLUE SEQUENCE PLACED INTO THE H11 HEAD

SEQ ID NO: 13

CSIDGKAPISLGDCSFAGWILGNPECEDLIGKTSWSYIVEKPNPTNGICYPGTLENEEEL

RLKFSGVLEFSKFEAFTSNGWGAVNS NRGV TAAC PHAGAK

SFFKNMVWLIHQSGTYPVIRRTFNNTKGRDVLMVWGVHHPATLKEHQDLYKKDSSYV

AVGSESYNRRFTPEISTRPKVNGQAGRMTFYVVTIVKPGEAITFESNGAFLAPRYAFELV

SLGNGKLFRSDLNIESC

Head domain (hazel)-amino acid HAZEL SEQUENCE PLACED INTO THE H6 HEAD DOMAIN

SEQ ID NO: 14

CKILNKAPLDLRGCTIEGWILGNPECELLLGDQSWSYIVERPTAQNGICYPGTLNEVEE

LKALIGSGERVERFEMFPKSTWAGVDT NIGV TAAC SHAGKS

SFYKNLLWIIKTKSAAYPVIKGTYNNTGNQPILYFWGVHHPPDTNEQNTLYGSGDRYVR

MGTESMNFAKSPEIAARPAVNGQRGRIDYYWSVLKPGETLNVESNGNLIAPVVYAYKF

VSTNNKGAVFKSNLPIENC

-continued

Head domain (green)-amino acid GREEN SEQUENCE PLACED INTO H6 HEAD DOMAIN.

SEQ ID NO: 15

CKILNKAPLDLRGCTIEGWILGNPECELLLGDQSWSYIVERPTAQNGICYPGTLNEVEE

LKALIGSGERVERFEMFPKSTWAGVDTTRGVTAACSH KGKSSFYKNLLWIIKTKSAAYP

VIKGTYNNTGNQPILYFWGVHHPPDTNEQNTLYGSGDRYVRMGTESMNFAKSPEIAA

RPAVNGQRGRIDYYWSVLKPGETLNVESNGNLIAPVVYAYKFVSTNNKGAVFKSNLPIE

NC

Head domain (orange)-amino acid

SEQ ID NO: 16

CSIDGKAPISLGDCSFAGWILGNPECEDLIGKTSWSYIVEKPNPTNGICYPGTLENEEEL

RLKFSGVLEFSKFEAFTSNGWGAVNS TKGV TAAC SHNGKS

SFFRNMVWLIHQSGTYPVIRRTFNNTKGRDVLMVWGVHHPATLKEHQDLYKKDSSYV

AVGSESYNRRFTPEISTRPKVNGQAGRMTFYVVTIVKPGEAITFESNGAFLAPRYAFELV

SLGNGKLFRSDLNIESC

Head domain (red)-amino acid

SEQ ID NO: 17

CDLDGVKPLILRDCSVAGWLLGNPECEEFLNVPEWSYIVEKANPANDLCYPGNF

NDYEELKHLLSRINHFEKIQIIPKSSWSDHET-

GGVSAACASHNGKSSFFRNVVWLIKKNNAYPTIKRSTNNTNQEDLLVLWGIHHP

NDAAEQTKLYQNPTTYISVGTSTLNQRLVPKIATRSKVNGQSGRMEFFWTILKPN

DAINFESNGNFIAPEYAYKIVKKGDSTIMKSELEYGNC

Head domain (blue)-nucleotide

SEQ ID NO: 18

TGCAGCATCGACGGCAAGGCCCCCATCAGCCTGGGCGACTGCAGCTTCGCCGGCTGGATC

CTGGGCAACCCCGAGTGCGAGGACCTGATCGGCAAGACCAGCTGGAGCTACATCGTGGAG

AAGCCCAACCCCACCAACGGCATCTGCTACCCCGGCACCCTGGAGAACGAGGAGGAGCTG

AGGCTGAAGTTCAGCGGCGTGCTGGAGTTCAGCAAGTTCGAGGCCTTCACCAGCAACGGC

TGGGGCGCCGTGAACAGCAACAGGGGCGTGACCGCCGCCTGCCCCCACGCCGGCGCCAAG

AGCTTCTTCAAGAACATGGTGTGGCTGATCCACCAGAGCGGCACCTACCCCGTGATCAGG

AGGACCTTCAACAACACCAAGGGCAGGGACGTGCTGATGGTGTGGGGCGTGCACCACCCC

GCCACCCTGAAGGAGCACCAGGACCTGTACAAGAAGGACAGCAGCTACGTGGCCGTGGGC

AGCGAGAGCTACAACAGGAGGTTCACCCCCGAGATCAGCACCAGGCCCAAGGTGAACGGC

CAGGCCGGCAGGATGACCTTCTACTGGACCATCGTGAAGCCCGGCGAGGCCATCACCTTC

GAGAGCAACGGCGCCTTCCTGGCCCCCAGGTACGCCTTCGAGCTGGTGAGCCTGGGCAAC

GGCAAGCTGTTCAGGAGCGACCTGAACATCGAGAGCTGC

Head domain (hazel)-nucleotide

SEQ ID NO: 19

TGCAAGATCCTGAACAAGGCCCCCCTGGACCTGAGGGGCTGCACCATCGAGGGCTGGATC

CTGGGCAACCCCGAGTGCGAGCTGCTGCTGGGCGACCAGAGCTGGAGCTACATCGTGGAG

AGGCCCACCGCCCAGAACGGCATCTGCTACCCCGGCACCCTGAACGAGGTGGAGGAGCTG

AAGGCCCTGATCGGCAGCGGCGAGAGGGTGGAGAGGTTCGAGATGTTCCCCAAGAGCACC

TGGGCCGGCGTGGACACCAACATCGGCGTGACCGCCGCCTGCAGCCACGCCGGCAAGAGC

AGCTTCTACAAGAACCTGCTGTGGATCATCAAGACCAAGAGCGCCGCCTACCCCGTGATC

AAGGGCACCTACAACAACACCGGCAACCAGCCCATCCTGTACTTCTGGGGCGTGCACCAC

-continued

CCCCCCGACACCAACGAGCAGAACACCCTGTACGGCAGCGGCGACAGGTACGTGAGGATG

GGCACCGAGAGCATGAACTTCGCCAAGAGCCCCGAGATCGCCGCCAGGCCCGCCGTGAAC

GGCCAGAGGGGCAGGATCGACTACTACTGGAGCGTGCTGAAGCCCGGCGAGACCCTGAAC

GTGGAGAGCAACGGCAACCTGATCGCCCCCTGGTACGCCTACAAGTTCGTGAGCACCAAC

AACAAGGGCGCCGTGTTCAAGAGCAACCTGCCCATCGAGAACTGC

Head domain (green)-nucleotide

SEQ ID NO: 20

TGCAAGATCCTGAACAAGGCCCCCCTGGACCTGAGGGGCTGCACCATCGAGGGCTGGATC

CTGGGCAACCCCGAGTGCGAGCTGCTGCTGGGCGACCAGAGCTGGAGCTACATCGTGGAG

AGGCCCACCGCCCAGAACGGCATCTGCTACCCCGGCACCCTGAACGAGGTGGAGGAGCTG

AAGGCCCTGATCGGCAGCGGCGAGAGGGTGGAGAGGTTCGAGATGTTCCCCAAGAGCACC

TGGGCCGGCGTGGACACCACCAGGGGCGTGACCGCCGCCTGCAGCCACAAGGGCAAGAGC

AAGAGCTTCTACAAGAACCTGCTGTGGATCATCAAGACCAAGAGCGCCGCCTACCCCGTG

ATCAAGGGCACCTACAACAACACCGGCAACCAGCCCATCCTGTACTTCTGGGGCGTGCAC

CACCCCCCCGACACCAACGAGCAGAACACCCTGTACGGCAGCGGCGACAGGTACGTGAGG

ATGGGCACCGAGAGCATGAACTTCGCCAAGAGCCCCGAGATCGCCGCCAGGCCCGCCGTG

AACGGCCAGAGGGGCAGGATCGACTACTACTGGAGCGTGCTGAAGCCCGGCGAGACCCTG

AACGTGGAGAGCAACGGCAACCTGATCGCCCCCTGGTACGCCTACAAGTTCGTGAGCACC

AACAACAAGGGCGCCGTGTTCAAGAGCAACCTGCCCATCGAGAACTGC

Head domain (orange)-nucleotide

SEQ ID NO: 21

TGCAGCATCGACGGCAAGGCCCCCATCAGCCTGGGCGACTGCAGCTTCGCCGGCTGGATC

CTGGGCAACCCCGAGTGCGAGGACCTGATCGGCAAGACCAGCTGGAGCTACATCGTGGAG

AAGCCCAACCCCACCAACGGCATCTGCTACCCCGGCACCCTGGAGAACGAGGAGGAGCTG

AGGCTGAAGTTCAGCGGCGTGCTGGAGTTCAGCAAGTTCGAGGCCTTCACCAGCAACGGC

TGGGGCGCCGTGAACAGCACCAAGGGCGTGACCGCCGCCTGCAGCCACAACGGCAAGAGC

AGCTTCTTCAGGAACATGGTGTGGCTGATCCACCAGAGCGGCACCTACCCCGTGATCAGG

AGGACCTTCAACAACACCAAGGGCAGGGACGTGCTGATGGTGTGGGGCGTGCACCACCCC

GCCACCCTGAAGGAGCACCAGGACCTGTACAAGAAGGACAGCAGCTACGTGGCCGTGGGC

AGCGAGAGCTACAACAGGAGGTTCACCCCCGAGATCAGCACCAGGCCCAAGGTGAACGGC

CAGGCCGGCAGGATGACCTTCTACTGGACCATCGTGAAGCCCGGCGAGGCCATCACCTTC

GAGAGCAACGGCGCCTTCCTGGCCCCCAGGTACGCCTTCGAGCTGGTGAGCCTGGGCAAC

GGCAAGCTGTTCAGGAGCGACCTGAACATCGAGAGCTGC

Head domain (red)-nucleotide

SEQ ID NO: 22

TGCGACCTGGACGGCGTGAAGCCCCTGATCCTGAGGGACTGCAGCGTGGCCGGCTGGCTG

CTGGGCAACCCCGAGTGCGAGGAGTTCCTGAACGTGCCCGAGTGGAGCTACATCGTGGAG

AAGGCCAACCCCGCCAACGACCTGTGCTACCCCGGCAACTTCAACGACTACGAGGAGCTG

AAGCACCTGCTGAGCAGGATCAACCACTTCGAGAAGATCCAGATCATCCCCAAGAGCAGC

TGGAGCGACCACGAGACCGGCGGCGTGAGCGCCGCCTGCGCCAGCCACAACGGCAAGAGC

AGCTTCTTCAGGAACGTGGTGTGGCTGATCAAGAAGAACAACGCCTACCCCACCATCAAG

AGGAGCTACAACAACACCAACCAGGAGGACCTGCTGGTGCTGTGGGGCATCCACCACCCC

AACGACGCCGCCGAGCAGACCAAGCTGTACCAGAACCCCACCACCTACATCAGCGTGGGC

ACCAGCACCCTGAACCAGAGGCTGGTGCCCAAGATCGCCACCAGGAGCAAGGTGAACGGC

-continued

CAGAGCGGCAGGATGGAGTTCTTCTGGACCATCCTGAAGCCCAACGACGCCATCAACTTC

GAGAGCAACGGCAACTTCATCGCCCCCGAGTACGCCTACAAGATCGTGAAGAAGGGCGAC

AGCACCATCATGAAGAGCGAGCTGGAGTACGGCAACTGC

H9 haemagglutinin-amino acid

SEQ ID NO: 23

METVSLITILLVVTVSNADKICIGYQSTNSTETVDTLTENNVPVTHAKELLHTEHNGML

CATSLGHPLILDTCTIEGLIYGNPSCDLLLGGREWSYIVERPSAVNGLCYPGNVENLEEL

RSLFSSARSYQRIQIFPDTIWNVSYSGTSKACSDSFYRSMRWLTQKNNAYPIQDAQYT

NNQGKNILFMWGINHPPTDTAQTNLYTRTDTTTSVATEEINRTFKPLIGPRPLVNGLQG

RIDYYWSVLKPGQTLRIRSNGNLIAPVVYGHILSGESHGRILKTDLKRGSCTVQCQTEKG

GLNTTLPFQNVSKYAFGNCSKYIGIKSLKLAVGLRNVPSRSSRGLFGAIAGFIEGGWSG

LVAGVVYGFQHSNDQGVGMAADRDSTQKAIDKITSKVNNIVDKMNKQYEIIDHEFSEVE

TRLNMINNKIDDQIQDIWAYNAELLVLLENQKTLDEHDANVNNLYNKVKRALGSNAVED

GKGCFELYHKCDDQCMETIRNGTYNRRKYQEESKLERQKIEGVKLESEGTYKILTIYST

VASSLVIAMGFAAFLFWAMSNGSCRCNICI

The invention claimed is:

1. A composition comprising 2, 3, 4 or 5 polypeptides, all of which are different, wherein the amino acid sequence of each polypeptide comprises a first region, wherein the first regions of two or more of the polypeptides each independently comprise an amino acid sequence selected from the group consisting of SEQ ID NOs: 13-17.

2. A composition comprising one or more:

(i) hetero-trimers comprising three polypeptides, wherein said polypeptides are all different; or (ii) homotrimers comprising three polypeptides, wherein the polypeptides are all the same;

wherein the amino acid sequence of each polypeptide comprises a first region, wherein the first region of each polypeptide comprises an amino acid sequence selected from the group consisting of SEQ ID NOs: 13-17.

3. A virus-like particle comprising two or more polypeptides, wherein the amino acid sequence of each polypeptide comprises a first region, wherein the first region of two or more of the polypeptides each independently comprise an amino acid sequence selected from the group consisting of SEQ ID NOs: 13-17.

4. A method of:

(i) treating influenza infection in a subject; or (ii) inducing a T-cell or B-cell response to an influenza antigen in a subject, the method comprising administering a therapeutically effective amount of the composition of claim 1 to a subject in need thereof.

5. The composition of claim 1, wherein the polypeptides are all 280-300 amino acids in length.

6. A method of:

(i) treating influenza infection in a subject; or (ii) inducing a T-cell or B-cell response to an influenza antigen in a subject, the method comprising administering a therapeutically effective amount of the composition of claim 2 to a subject in need thereof.

* * * * *

SEQUENCE LISTING

<160> NUMBER OF SEQ ID NOS: 28

<210> SEQ ID NO 1
<211> LENGTH: 234
<212> TYPE: PRT
<213> ORGANISM: Influenza A virus

<400> SEQUENCE: 1

```
Cys Lys Leu Arg Gly Val Ala Pro Leu His Leu Gly Lys Cys Asn Ile
1               5                   10                  15

Ala Gly Trp Ile Leu Gly Asn Pro Glu Cys Glu Ser Leu Ser Thr Ala
            20                  25                  30

Ser Ser Trp Ser Tyr Ile Val Glu Thr Ser Ser Ser Asp Asn Gly Thr
        35                  40                  45

Cys Tyr Pro Gly Asp Phe Ile Asp Tyr Glu Glu Leu Arg Glu Gln Leu
    50                  55                  60

Ser Ser Val Ser Ser Phe Glu Arg Phe Glu Ile Phe Pro Lys Thr Ser
65                  70                  75                  80

Ser Trp Pro Asn His Asp Ser Asn Lys Gly Val Thr Ala Ala Cys Pro
                85                  90                  95

His Ala Gly Ala Lys Ser Phe Tyr Lys Asn Leu Ile Trp Leu Val Lys
            100                 105                 110

Lys Gly Asn Ser Tyr Pro Lys Leu Ser Lys Ser Tyr Ile Asn Asp Lys
        115                 120                 125

Gly Lys Glu Val Leu Val Leu Trp Gly Ile His His Pro Ser Thr Ser
    130                 135                 140

Ala Asp Gln Gln Ser Leu Tyr Gln Asn Ala Asp Ala Tyr Val Phe Val
145                 150                 155                 160

Gly Thr Ser Arg Tyr Ser Lys Lys Phe Lys Pro Glu Ile Ala Ile Arg
                165                 170                 175

Pro Lys Val Arg Asp Gln Glu Gly Arg Met Asn Tyr Tyr Trp Thr Leu
            180                 185                 190

Val Glu Pro Gly Asp Lys Ile Thr Phe Glu Ala Thr Gly Asn Leu Val
```

```
        195                 200                 205

Val Pro Arg Tyr Ala Phe Ala Met Glu Arg Asn Ala Gly Ser Gly Ile
    210                 215                 220

Ile Ile Ser Asp Thr Pro Val His Asp Cys
225                 230


<210> SEQ ID NO 2
<211> LENGTH: 235
<212> TYPE: PRT
<213> ORGANISM: Influenza A virus

<400> SEQUENCE: 2

Cys Lys Ile Leu Asn Lys Ala Pro Leu Asp Leu Arg Gly Cys Thr Ile
1               5                   10                  15

Glu Gly Trp Ile Leu Gly Asn Pro Gln Cys Asp Leu Leu Leu Gly Asp
            20                  25                  30

Gln Ser Trp Ser Tyr Ile Val Glu Arg Pro Thr Ala Gln Asn Gly Ile
        35                  40                  45

Cys Tyr Pro Gly Thr Leu Asn Glu Val Glu Glu Leu Lys Ala Leu Ile
    50                  55                  60

Gly Ser Gly Glu Arg Val Glu Arg Phe Glu Met Phe Pro Lys Ser Thr
65                  70                  75                  80

Trp Ala Gly Val Asp Thr Asn Ser Gly Val Thr Ser Ala Cys Pro Tyr
                85                  90                  95

Asn Ser Gly Ser Ser Phe Tyr Arg Asn Leu Leu Trp Ile Ile Lys Thr
            100                 105                 110

Lys Ser Ala Ala Tyr Pro Val Ile Lys Gly Thr Tyr Asn Asn Thr Gly
        115                 120                 125

Asn Gln Pro Ile Leu Tyr Phe Trp Gly Val His His Pro Pro Asp Thr
    130                 135                 140

Asn Glu Gln Asn Thr Leu Tyr Gly Ser Gly Asp Arg Tyr Val Arg Met
145                 150                 155                 160

Gly Thr Glu Ser Met Asn Phe Ala Lys Ser Pro Glu Ile Ala Ala Arg
                165                 170                 175

Pro Ala Val Asn Gly Gln Arg Gly Arg Ile Asp Tyr Tyr Trp Ser Val
            180                 185                 190

Leu Lys Pro Gly Glu Thr Leu Asn Val Glu Ser Asn Gly Asn Leu Ile
        195                 200                 205

Ala Pro Trp Tyr Ala Tyr Lys Phe Val Ser Thr Asn Asn Lys Gly Ala
    210                 215                 220

Val Phe Lys Ser Asn Leu Pro Ile Glu Asn Cys
225                 230                 235


<210> SEQ ID NO 3
<211> LENGTH: 233
<212> TYPE: PRT
<213> ORGANISM: Influenza A virus

<400> SEQUENCE: 3

Cys Asp Leu Asp Gly Val Lys Pro Leu Ile Leu Arg Asp Cys Ser Val
1               5                   10                  15

Ala Gly Trp Leu Leu Gly Asn Pro Met Cys Asp Glu Phe Leu Asn Val
            20                  25                  30

Pro Glu Trp Ser Tyr Ile Val Glu Lys Ala Asn Pro Ala Asn Asp Leu
        35                  40                  45

Cys Tyr Pro Gly Asn Phe Asn Asp Tyr Glu Glu Leu Lys His Leu Leu
```

-continued

```
    50                  55                  60

Ser Arg Ile Asn His Phe Glu Lys Ile Gln Ile Ile Pro Lys Ser Ser
65                  70                  75                  80

Trp Ser Asp His Glu Ala Ser Ser Gly Val Ser Ser Ala Cys Pro Tyr
                85                  90                  95

Gln Gly Arg Ser Ser Phe Phe Arg Asn Val Val Trp Leu Ile Lys Lys
            100                 105                 110

Asn Asn Ala Tyr Pro Thr Ile Lys Arg Ser Tyr Asn Asn Thr Asn Gln
        115                 120                 125

Glu Asp Leu Leu Val Leu Trp Gly Ile His His Pro Asn Asp Ala Ala
    130                 135                 140

Glu Gln Thr Lys Leu Tyr Gln Asn Pro Thr Thr Tyr Ile Ser Val Gly
145                 150                 155                 160

Thr Ser Thr Leu Asn Gln Arg Leu Val Pro Lys Ile Ala Thr Arg Ser
                165                 170                 175

Lys Val Asn Gly Gln Ser Gly Arg Met Glu Phe Phe Trp Thr Ile Leu
            180                 185                 190

Lys Pro Asn Asp Ala Ile Asn Phe Glu Ser Asn Gly Asn Phe Ile Ala
        195                 200                 205

Pro Glu Tyr Ala Tyr Lys Ile Val Lys Lys Gly Asp Ser Thr Ile Met
    210                 215                 220

Lys Ser Glu Leu Glu Tyr Gly Asn Cys
225                 230


<210> SEQ ID NO 4
<211> LENGTH: 233
<212> TYPE: PRT
<213> ORGANISM: Influenza A virus

<400> SEQUENCE: 4

Cys Ser Ile Asp Gly Lys Ala Pro Ile Ser Leu Gly Asp Cys Ser Phe
1               5                   10                  15

Ala Gly Trp Ile Leu Gly Asn Pro Met Cys Asp Asp Leu Ile Gly Lys
            20                  25                  30

Thr Ser Trp Ser Tyr Ile Val Glu Lys Pro Asn Pro Thr Asn Gly Ile
        35                  40                  45

Cys Tyr Pro Gly Thr Leu Glu Asn Glu Glu Glu Leu Arg Leu Lys Phe
    50                  55                  60

Ser Gly Val Leu Glu Phe Ser Lys Phe Glu Ala Phe Thr Ser Asn Gly
65                  70                  75                  80

Trp Gly Ala Val Asn Ser Gly Ala Gly Val Thr Ala Ala Cys Lys Phe
                85                  90                  95

Gly Ser Ser Asn Ser Phe Phe Arg Asn Met Val Trp Leu Ile His Gln
            100                 105                 110

Ser Gly Thr Tyr Pro Val Ile Arg Arg Thr Phe Asn Asn Thr Lys Gly
        115                 120                 125

Arg Asp Val Leu Met Val Trp Gly Val His His Pro Ala Thr Leu Lys
    130                 135                 140

Glu His Gln Asp Leu Tyr Lys Lys Asp Ser Ser Tyr Val Ala Val Gly
145                 150                 155                 160

Ser Glu Ser Tyr Asn Arg Arg Phe Thr Pro Glu Ile Ser Thr Arg Pro
                165                 170                 175

Lys Val Asn Gly Gln Ala Gly Arg Met Thr Phe Tyr Trp Thr Ile Val
            180                 185                 190
```

-continued

```
Lys Pro Gly Glu Ala Ile Thr Phe Glu Ser Asn Gly Ala Phe Leu Ala
        195                 200                 205

Pro Arg Tyr Ala Phe Glu Leu Val Ser Leu Gly Asn Gly Lys Leu Phe
    210                 215                 220

Arg Ser Asp Leu Asn Ile Glu Ser Cys
225                 230


<210> SEQ ID NO 5
<211> LENGTH: 702
<212> TYPE: DNA
<213> ORGANISM: Influenza A virus

<400> SEQUENCE: 5

tgcaagctga ggggcgtggc ccccctgcac ctgggcaagt gcaacatcgc cggctggatc      60

ctgggcaacc ccgagtgcga gagcctgagc accgccagca gctggagcta catcgtggag     120

accagcagca gcgacaacgg cacctgctac cccggcgact tcatcgacta cgaggagctg     180

agggagcagc tgagcagcgt gagcagcttc gagaggttcg agatcttccc caagaccagc     240

agctggccca accacgacag caacaagggc gtgaccgccg cctgccccca cgccggcgcc     300

aagagcttct acaagaacct gatctggctg gtgaagaagg gcaacagcta ccccaagctg     360

agcaagagct acatcaacga caagggcaag gaggtgctgg tgctgtgggg catccaccac     420

cccagcacca gcgccgacca gcagagcctg taccagaacg ccgacgccta cgtgttcgtg     480

ggcaccagca ggtacagcaa gaagttcaag cccgagatcg ccatcaggcc caaggtgagg     540

gaccaggagg gcaggatgaa ctactactgg accctggtgg agcccggcga caagatcacc     600

ttcgaggcca ccggcaacct ggtggtgccc aggtacgcct tcgccatgga gaggaacgcc     660

ggcagcggca tcatcatcag cgacaccccc gtgcacgact gc                        702


<210> SEQ ID NO 6
<211> LENGTH: 705
<212> TYPE: DNA
<213> ORGANISM: Influenza A virus

<400> SEQUENCE: 6

tgcaagatcc tgaacaaggc ccccctggac ctgaggggct gcaccatcga gggctggatc      60

ctgggcaacc cccagtgcga cctgctgctg ggcgaccaga gctggagcta catcgtggag     120

aggcccaccg cccagaacgg catctgctac cccggcaccc tgaacgaggt ggaggagctg     180

aaggccctga tcggcagcgg cgagagggtg gagaggttcg agatgttccc caagagcacc     240

tgggccggcg tggacaccaa cagcggcgtg accagcgcct gcccctacaa cagcggcagc     300

agcttctaca ggaacctgct gtggatcatc aagaccaaga gcgccgccta ccccgtgatc     360

aagggcacct acaacaacac cggcaaccag cccatcctgt acttctgggg cgtgcaccac     420

ccccccgaca ccaacgagca gaacaccctg tacggcagcg gcgacaggta cgtgaggatg     480

ggcaccgaga gcatgaactt cgccaagagc cccgagatcg ccgccaggcc cgccgtgaac     540

ggccagaggg gcaggatcga ctactactgg agcgtgctga agcccggcga gaccctgaac     600

gtggagagca acggcaacct gatcgccccc tggtacgcct acaagttcgt gagcaccaac     660

aacaagggcg ccgtgttcaa gagcaacctg cccatcgaga actgc                     705


<210> SEQ ID NO 7
<211> LENGTH: 699
<212> TYPE: DNA
<213> ORGANISM: Influenza A virus
```

<400> SEQUENCE: 7
tgcgacctgg acggcgtgaa gcccctgatc ctgagggact gcagcgtggc cggctggctg 60
ctgggcaacc ccatgtgcga cgagttcctg aacgtgcccg agtggagcta catcgtggag 120
aaggccaacc ccgccaacga cctgtgctac cccggcaact tcaacgacta cgaggagctg 180
aagcacctgc tgagcaggat caaccacttc gagaagatcc agatcatccc caagagcagc 240
tggagcgacc acgaggccag cagcggcgtg agcagcgcct gcccctacca gggcaggagc 300
agcttcttca ggaacgtggt gtggctgatc aagaagaaca acgcctaccc caccatcaag 360
aggagctaca acaacaccaa ccaggaggac ctgctggtgc tgtggggcat ccaccacccc 420
aacgacgccg ccgagcagac caagctgtac cagaacccca ccacctacat cagcgtgggc 480
accagcaccc tgaaccagag gctggtgccc aagatcgcca ccaggagcaa ggtgaacggc 540
cagagcggca ggatggagtt cttctggacc atcctgaagc ccaacgacgc catcaacttc 600
gagagcaacg gcaacttcat cgcccccgag tacgcctaca agatcgtgaa gaagggcgac 660
agcaccatca tgaagagcga gctggagtac ggcaactgc 699

<210> SEQ ID NO 8
<211> LENGTH: 699
<212> TYPE: DNA
<213> ORGANISM: Influenza A virus

<400> SEQUENCE: 8
tgcagcatcg acggcaaggc ccccatcagc ctgggcgact gcagcttcgc cggctggatc 60
ctgggcaacc ccatgtgcga cgacctgatc ggcaagacca gctggagcta catcgtggag 120
aagcccaacc ccaccaacgg catctgctac cccggcaccc tggagaacga ggaggagctg 180
aggctgaagt tcagcggcgt gctggagttc agcaagttcg aggccttcac cagcaacggc 240
tggggcgccg tgaacagcgg cgccggcgtg accgccgcct gcaagttcgg cagcagcaac 300
agcttcttca ggaacatggt gtggctgatc caccagagcg gcacctaccc cgtgatcagg 360
aggaccttca acaacaccaa gggcagggac gtgctgatgg tgtggggcgt gcaccacccc 420
gccaccctga aggagcacca ggacctgtac aagaaggaca gcagctacgt ggccgtgggc 480
agcgagagct acaacaggag gttcaccccc gagatcagca ccaggcccaa ggtgaacggc 540
caggccggca ggatgacctt ctactggacc atcgtgaagc ccggcgaggc catcaccttc 600
gagagcaacg gcgccttcct ggcccccagg tacgccttcg agctggtgag cctgggcaac 660
ggcaagctgt tcaggagcga cctgaacatc gagagctgc 699

<210> SEQ ID NO 9
<211> LENGTH: 566
<212> TYPE: PRT
<213> ORGANISM: Influenza A virus

<400> SEQUENCE: 9

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly

-continued

```
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495
```

-continued

```
Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 10
<211> LENGTH: 566
<212> TYPE: PRT
<213> ORGANISM: Influenza A virus

<400> SEQUENCE: 10

Met Ile Ala Ile Ile Val Ile Ala Ile Leu Ala Ala Thr Gly Lys Ser
1               5                   10                  15

Asp Lys Ile Cys Ile Gly Tyr His Ala Asn Asn Ser Thr Thr Gln Val
            20                  25                  30

Asp Thr Ile Leu Glu Lys Asn Val Thr Val Thr His Ser Val Glu Leu
        35                  40                  45

Leu Glu Asn Gln Lys Glu Glu Arg Phe Cys Lys Ile Leu Asn Lys Ala
    50                  55                  60

Pro Leu Asp Leu Arg Gly Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Thr Leu Asn
            100                 105                 110

Glu Val Glu Glu Leu Lys Ala Leu Ile Gly Ser Gly Glu Arg Val Glu
        115                 120                 125

Arg Phe Glu Met Phe Pro Lys Ser Thr Trp Ala Gly Val Asp Thr Asn
    130                 135                 140

Ser Gly Val Thr Ser Ala Cys Pro Tyr Asn Ser Gly Ser Ser Phe Tyr
145                 150                 155                 160

Arg Asn Leu Leu Trp Ile Ile Lys Thr Lys Ser Ala Ala Tyr Pro Val
                165                 170                 175

Ile Lys Gly Thr Tyr Asn Asn Thr Gly Asn Gln Pro Ile Leu Tyr Phe
            180                 185                 190

Trp Gly Val His His Pro Pro Asp Thr Asn Glu Gln Asn Thr Leu Tyr
        195                 200                 205

Gly Ser Gly Asp Arg Tyr Val Arg Met Gly Thr Glu Ser Met Asn Phe
    210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Val Leu Lys Pro Gly Glu Thr Leu
                245                 250                 255

Asn Val Glu Ser Asn Gly Asn Leu Ile Ala Pro Trp Tyr Ala Tyr Lys
            260                 265                 270

Phe Val Ser Thr Asn Asn Lys Gly Ala Val Phe Lys Ser Asn Leu Pro
        275                 280                 285

Ile Glu Asn Cys Asp Ala Thr Cys Gln Thr Ile Ala Gly Val Leu Arg
```

-continued

```
    290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

Asn Val Pro Gln Ile Glu Thr Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Glu Asn Ser Gln Gly Ser Gly Tyr Ala Ala Asp Arg Glu Ser
    370                 375                 380

Thr Gln Lys Ala Ile Asp Gly Ile Thr Asn Lys Val Asn Ser Ile Ile
385                 390                 395                 400

Asp Lys Met Asn Thr Gln Phe Glu Ala Val Asp His Glu Phe Ser Asn
                405                 410                 415

Leu Glu Arg Arg Ile Asp Asn Leu Asn Lys Arg Met Glu Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Leu His Asp Ala Asn Val Lys Asn Leu Tyr Glu
    450                 455                 460

Lys Val Lys Ser Gln Leu Arg Asp Asn Ala Asn Asp Leu Gly Asn Gly
465                 470                 475                 480

Cys Phe Glu Phe Trp His Lys Cys Asp Asn Glu Cys Ile Glu Ser Val
                485                 490                 495

Lys Asn Gly Thr Tyr Asp Tyr Pro Lys Tyr Gln Asp Glu Ser Lys Leu
            500                 505                 510

Asn Arg Gln Glu Ile Glu Ser Val Lys Leu Glu Asn Leu Gly Val Tyr
        515                 520                 525

Gln Ile Leu Ala Ile Tyr Ser Thr Val Ser Ser Ser Leu Val Leu Val
    530                 535                 540

Gly Leu Ile Ile Ala Met Gly Leu Trp Met Cys Ser Asn Gly Ser Met
545                 550                 555                 560

Gln Cys Arg Ile Cys Ile
                565


<210> SEQ ID NO 11
<211> LENGTH: 564
<212> TYPE: PRT
<213> ORGANISM: Influenza A virus

<400> SEQUENCE: 11

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95
```

-continued

```
Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Lys Lys Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
```

```
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 12
<211> LENGTH: 565
<212> TYPE: PRT
<213> ORGANISM: Influenza A virus

<400> SEQUENCE: 12

Met Lys Lys Thr Leu Leu Phe Ala Ala Ile Ile Ile Cys Ile Gln Ala
1               5                   10                  15

Asp Glu Ile Cys Ile Gly Tyr Leu Ser Asn Asn Ser Thr Glu Lys Val
            20                  25                  30

Asp Thr Ile Ile Glu Ser Asn Val Thr Val Thr Ser Ser Val Glu Leu
        35                  40                  45

Val Glu Asn Glu His Thr Gly Ser Phe Cys Ser Ile Asp Gly Lys Ala
    50                  55                  60

Pro Ile Ser Leu Gly Asp Cys Ser Phe Ala Gly Trp Ile Leu Gly Asn
65                  70                  75                  80

Pro Met Cys Asp Asp Leu Ile Gly Lys Thr Ser Trp Ser Tyr Ile Val
                85                  90                  95

Glu Lys Pro Asn Pro Thr Asn Gly Ile Cys Tyr Pro Gly Thr Leu Glu
            100                 105                 110

Asn Glu Glu Glu Leu Arg Leu Lys Phe Ser Gly Val Leu Glu Phe Ser
        115                 120                 125

Lys Phe Glu Ala Phe Thr Ser Asn Gly Trp Gly Ala Val Asn Ser Gly
    130                 135                 140

Ala Gly Val Thr Ala Ala Cys Lys Phe Gly Ser Ser Asn Ser Phe Phe
145                 150                 155                 160

Arg Asn Met Val Trp Leu Ile His Gln Ser Gly Thr Tyr Pro Val Ile
                165                 170                 175

Arg Arg Thr Phe Asn Asn Thr Lys Gly Arg Asp Val Leu Met Val Trp
            180                 185                 190

Gly Val His His Pro Ala Thr Leu Lys Glu His Gln Asp Leu Tyr Lys
        195                 200                 205

Lys Asp Ser Ser Tyr Val Ala Val Gly Ser Glu Ser Tyr Asn Arg Arg
    210                 215                 220

Phe Thr Pro Glu Ile Ser Thr Arg Pro Lys Val Asn Gly Gln Ala Gly
225                 230                 235                 240

Arg Met Thr Phe Tyr Trp Thr Ile Val Lys Pro Gly Glu Ala Ile Thr
                245                 250                 255

Phe Glu Ser Asn Gly Ala Phe Leu Ala Pro Arg Tyr Ala Phe Glu Leu
            260                 265                 270

Val Ser Leu Gly Asn Gly Lys Leu Phe Arg Ser Asp Leu Asn Ile Glu
        275                 280                 285

Ser Cys Ser Thr Lys Cys Gln Ser Glu Ile Gly Gly Ile Asn Thr Asn
    290                 295                 300

Arg Ser Phe His Asn Val His Arg Asn Thr Ile Gly Asp Cys Pro Lys
305                 310                 315                 320

Tyr Val Asn Val Lys Ser Leu Lys Leu Ala Thr Gly Leu Arg Asn Val
```

```
                325                 330                 335

Pro Ala Ile Ala Thr Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Arg Asn Glu Glu Gly Thr Gly Ile Ala Ala Asp Lys Glu Ser Thr Gln
    370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Ile Asp
            420                 425                 430

Ile Trp Ser Tyr Asn Ala Gln Leu Leu Val Leu Leu Glu Asn Glu Lys
        435                 440                 445

Thr Leu Asp Leu His Asp Ser Asn Val Arg Asn Leu His Glu Lys Val
    450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Glu Cys Ile Glu Lys Val Arg Asn
                485                 490                 495

Gly Thr Tyr Asp His Lys Glu Phe Glu Glu Glu Ser Lys Leu Asn Arg
            500                 505                 510

Gln Glu Ile Glu Gly Val Lys Leu Asp Ser Asn Gly Asn Val Tyr Lys
        515                 520                 525

Ile Leu Ser Ile Tyr Ser Cys Ile Ala Ser Ser Leu Val Leu Ala Ala
    530                 535                 540

Ile Ile Met Gly Phe Ile Leu Trp Ala Cys Ser Asn Gly Ser Cys Arg
545                 550                 555                 560

Cys Thr Ile Cys Ile
                565


<210> SEQ ID NO 13
<211> LENGTH: 233
<212> TYPE: PRT
<213> ORGANISM: Influenza A virus

<400> SEQUENCE: 13

Cys Ser Ile Asp Gly Lys Ala Pro Ile Ser Leu Gly Asp Cys Ser Phe
1               5                   10                  15

Ala Gly Trp Ile Leu Gly Asn Pro Glu Cys Glu Asp Leu Ile Gly Lys
            20                  25                  30

Thr Ser Trp Ser Tyr Ile Val Glu Lys Pro Asn Pro Thr Asn Gly Ile
        35                  40                  45

Cys Tyr Pro Gly Thr Leu Glu Asn Glu Glu Glu Leu Arg Leu Lys Phe
    50                  55                  60

Ser Gly Val Leu Glu Phe Ser Lys Phe Glu Ala Phe Thr Ser Asn Gly
65                  70                  75                  80

Trp Gly Ala Val Asn Ser Asn Lys Gly Val Thr Ala Ala Cys Pro His
                85                  90                  95

Ala Gly Ala Lys Ser Phe Phe Lys Asn Met Val Trp Leu Ile His Gln
            100                 105                 110

Ser Gly Thr Tyr Pro Val Ile Arg Arg Thr Phe Asn Asn Thr Lys Gly
        115                 120                 125
```

```
Arg Asp Val Leu Met Val Trp Gly Val His His Pro Ala Thr Leu Lys
    130                 135                 140

Glu His Gln Asp Leu Tyr Lys Lys Asp Ser Ser Tyr Val Ala Val Gly
145                 150                 155                 160

Ser Glu Ser Tyr Asn Arg Arg Phe Thr Pro Glu Ile Ser Thr Arg Pro
                165                 170                 175

Lys Val Asn Gly Gln Ala Gly Arg Met Thr Phe Tyr Trp Thr Ile Val
            180                 185                 190

Lys Pro Gly Glu Ala Ile Thr Phe Glu Ser Asn Gly Ala Phe Leu Ala
        195                 200                 205

Pro Arg Tyr Ala Phe Glu Leu Val Ser Leu Gly Asn Gly Lys Leu Phe
    210                 215                 220

Arg Ser Asp Leu Asn Ile Glu Ser Cys
225                 230
```

<210> SEQ ID NO 14
<211> LENGTH: 235
<212> TYPE: PRT
<213> ORGANISM: Influenza A virus

<400> SEQUENCE: 14

```
Cys Lys Ile Leu Asn Lys Ala Pro Leu Asp Leu Arg Gly Cys Thr Ile
1               5                   10                  15

Glu Gly Trp Ile Leu Gly Asn Pro Glu Cys Glu Leu Leu Leu Gly Asp
            20                  25                  30

Gln Ser Trp Ser Tyr Ile Val Glu Arg Pro Thr Ala Gln Asn Gly Ile
        35                  40                  45

Cys Tyr Pro Gly Thr Leu Asn Glu Val Glu Glu Leu Lys Ala Leu Ile
    50                  55                  60

Gly Ser Gly Glu Arg Val Glu Arg Phe Glu Met Phe Pro Lys Ser Thr
65                  70                  75                  80

Trp Ala Gly Val Asp Thr Asn Ile Gly Val Thr Ala Ala Cys Ser His
                85                  90                  95

Ala Gly Lys Ser Ser Phe Tyr Lys Asn Leu Leu Trp Ile Ile Lys Thr
            100                 105                 110

Lys Ser Ala Ala Tyr Pro Val Ile Lys Gly Thr Tyr Asn Asn Thr Gly
        115                 120                 125

Asn Gln Pro Ile Leu Tyr Phe Trp Gly Val His His Pro Pro Asp Thr
    130                 135                 140

Asn Glu Gln Asn Thr Leu Tyr Gly Ser Gly Asp Arg Tyr Val Arg Met
145                 150                 155                 160

Gly Thr Glu Ser Met Asn Phe Ala Lys Ser Pro Glu Ile Ala Ala Arg
                165                 170                 175

Pro Ala Val Asn Gly Gln Arg Gly Arg Ile Asp Tyr Tyr Trp Ser Val
            180                 185                 190

Leu Lys Pro Gly Glu Thr Leu Asn Val Glu Ser Asn Gly Asn Leu Ile
        195                 200                 205

Ala Pro Trp Tyr Ala Tyr Lys Phe Val Ser Thr Asn Asn Lys Gly Ala
    210                 215                 220

Val Phe Lys Ser Asn Leu Pro Ile Glu Asn Cys
225                 230                 235
```

<210> SEQ ID NO 15
<211> LENGTH: 235
<212> TYPE: PRT
<213> ORGANISM: Influenza A virus -continued

<400> SEQUENCE: 15

Cys Lys Ile Leu Asn Lys Ala Pro Leu Asp Leu Arg Gly Cys Thr Ile
1 5 10 15

Glu Gly Trp Ile Leu Gly Asn Pro Glu Cys Glu Leu Leu Leu Gly Asp
20 25 30

Gln Ser Trp Ser Tyr Ile Val Glu Arg Pro Thr Ala Gln Asn Gly Ile
35 40 45

Cys Tyr Pro Gly Thr Leu Asn Glu Val Glu Glu Leu Lys Ala Leu Ile
50 55 60

Gly Ser Gly Glu Arg Val Glu Arg Phe Glu Met Phe Pro Lys Ser Thr
65 70 75 80

Trp Ala Gly Val Asp Thr Thr Arg Gly Val Thr Ala Ala Cys Ser His
85 90 95

Lys Gly Lys Ser Ser Phe Tyr Arg Asn Leu Leu Trp Ile Ile Lys Thr
100 105 110

Lys Ser Ala Ala Tyr Pro Val Ile Lys Gly Thr Tyr Asn Asn Thr Gly
115 120 125

Asn Gln Pro Ile Leu Tyr Phe Trp Gly Val His His Pro Pro Asp Thr
130 135 140

Asn Glu Gln Asn Thr Leu Tyr Gly Ser Gly Asp Arg Tyr Val Arg Met
145 150 155 160

Gly Thr Glu Ser Met Asn Phe Ala Lys Ser Pro Glu Ile Ala Ala Arg
165 170 175

Pro Ala Val Asn Gly Gln Arg Gly Arg Ile Asp Tyr Tyr Trp Ser Val
180 185 190

Leu Lys Pro Gly Glu Thr Leu Asn Val Glu Ser Asn Gly Asn Leu Ile
195 200 205

Ala Pro Trp Tyr Ala Tyr Lys Phe Val Ser Thr Asn Asn Lys Gly Ala
210 215 220

Val Phe Lys Ser Asn Leu Pro Ile Glu Asn Cys
225 230 235

<210> SEQ ID NO 16
<211> LENGTH: 233
<212> TYPE: PRT
<213> ORGANISM: Influenza A virus

<400> SEQUENCE: 16

Cys Ser Ile Asp Gly Lys Ala Pro Ile Ser Leu Gly Asp Cys Ser Phe
1 5 10 15

Ala Gly Trp Ile Leu Gly Asn Pro Glu Cys Glu Asp Leu Ile Gly Lys
20 25 30

Thr Ser Trp Ser Tyr Ile Val Glu Lys Pro Asn Pro Thr Asn Gly Ile
35 40 45

Cys Tyr Pro Gly Thr Leu Glu Asn Glu Glu Glu Leu Arg Leu Lys Phe
50 55 60

Ser Gly Val Leu Glu Phe Ser Lys Phe Glu Ala Phe Thr Ser Asn Gly
65 70 75 80

Trp Gly Ala Val Asn Ser Thr Lys Gly Val Thr Ala Ala Cys Ser His
85 90 95

Asn Gly Lys Ser Ser Phe Phe Arg Asn Met Val Trp Leu Ile His Gln
100 105 110

Ser Gly Thr Tyr Pro Val Ile Arg Arg Thr Phe Asn Asn Thr Lys Gly
115 120 125

```
Arg Asp Val Leu Met Val Trp Gly Val His His Pro Ala Thr Leu Lys
    130                 135                 140

Glu His Gln Asp Leu Tyr Lys Lys Asp Ser Ser Tyr Val Ala Val Gly
145                 150                 155                 160

Ser Glu Ser Tyr Asn Arg Arg Phe Thr Pro Glu Ile Ser Thr Arg Pro
                165                 170                 175

Lys Val Asn Gly Gln Ala Gly Arg Met Thr Phe Tyr Trp Thr Ile Val
            180                 185                 190

Lys Pro Gly Glu Ala Ile Thr Phe Glu Ser Asn Gly Ala Phe Leu Ala
        195                 200                 205

Pro Arg Tyr Ala Phe Glu Leu Val Ser Leu Gly Asn Gly Lys Leu Phe
    210                 215                 220

Arg Ser Asp Leu Asn Ile Glu Ser Cys
225                 230
```

<210> SEQ ID NO 17
<211> LENGTH: 233
<212> TYPE: PRT
<213> ORGANISM: Influenza A virus

<400> SEQUENCE: 17

```
Cys Asp Leu Asp Gly Val Lys Pro Leu Ile Leu Arg Asp Cys Ser Val
1               5                   10                  15

Ala Gly Trp Leu Leu Gly Asn Pro Glu Cys Glu Glu Phe Leu Asn Val
            20                  25                  30

Pro Glu Trp Ser Tyr Ile Val Glu Lys Ala Asn Pro Ala Asn Asp Leu
        35                  40                  45

Cys Tyr Pro Gly Asn Phe Asn Asp Tyr Glu Glu Leu Lys His Leu Leu
    50                  55                  60

Ser Arg Ile Asn His Phe Glu Lys Ile Gln Ile Ile Pro Lys Ser Ser
65                  70                  75                  80

Trp Ser Asp His Glu Thr Gly Gly Val Ser Ala Ala Cys Ala Ser His
                85                  90                  95

Asn Gly Lys Ser Ser Phe Phe Arg Asn Val Val Trp Leu Ile Lys Lys
            100                 105                 110

Asn Asn Ala Tyr Pro Thr Ile Lys Arg Ser Tyr Asn Asn Thr Asn Gln
        115                 120                 125

Glu Asp Leu Leu Val Leu Trp Gly Ile His His Pro Asn Asp Ala Ala
    130                 135                 140

Glu Gln Thr Lys Leu Tyr Gln Asn Pro Thr Thr Tyr Ile Ser Val Gly
145                 150                 155                 160

Thr Ser Thr Leu Asn Gln Arg Leu Val Pro Lys Ile Ala Thr Arg Ser
                165                 170                 175

Lys Val Asn Gly Gln Ser Gly Arg Met Glu Phe Phe Trp Thr Ile Leu
            180                 185                 190

Lys Pro Asn Asp Ala Ile Asn Phe Glu Ser Asn Gly Asn Phe Ile Ala
        195                 200                 205

Pro Glu Tyr Ala Tyr Lys Ile Val Lys Lys Gly Asp Ser Thr Ile Met
    210                 215                 220

Lys Ser Glu Leu Glu Tyr Gly Asn Cys
225                 230
```

<210> SEQ ID NO 18
<211> LENGTH: 699
<212> TYPE: DNA

<213> ORGANISM: Influenza A virus

<400> SEQUENCE: 18
tgcagcatcg acggcaaggc ccccatcagc ctgggcgact gcagcttcgc cggctggatc 60
ctgggcaacc ccgagtgcga ggacctgatc ggcaagacca gctggagcta catcgtggag 120
aagcccaacc ccaccaacgg catctgctac cccggcaccc tggagaacga ggaggagctg 180
aggctgaagt tcagcggcgt gctggagttc agcaagttcg aggccttcac cagcaacggc 240
tggggcgccg tgaacagcaa caggggcgtg accgccgcct gcccccacgc cggcgccaag 300
agcttcttca agaacatggt gtggctgatc caccagagcg gcacctaccc cgtgatcagg 360
aggaccttca acaacaccaa gggcagggac gtgctgatgg tgtggggcgt gcaccacccc 420
gccaccctga aggagcacca ggacctgtac aagaaggaca gcagctacgt ggccgtgggc 480
agcgagagct acaacaggag gttcaccccc gagatcagca ccaggcccaa ggtgaacggc 540
caggccggca ggatgacctt ctactggacc atcgtgaagc ccggcgaggc catcaccttc 600
gagagcaacg gcgccttcct ggcccccagg tacgccttcg agctggtgag cctgggcaac 660
ggcaagctgt tcaggagcga cctgaacatc gagagctgc 699

<210> SEQ ID NO 19
<211> LENGTH: 705
<212> TYPE: DNA
<213> ORGANISM: Influenza A virus

<400> SEQUENCE: 19
tgcaagatcc tgaacaaggc ccccctggac ctgaggggct gcaccatcga gggctggatc 60
ctgggcaacc ccgagtgcga gctgctgctg ggcgaccaga gctggagcta catcgtggag 120
aggcccaccg cccagaacgg catctgctac cccggcaccc tgaacgaggt ggaggagctg 180
aaggccctga tcggcagcgg cgagagggtg gagaggttcg agatgttccc caagagcacc 240
tgggccggcg tggacaccaa catcggcgtg accgccgcct gcagccacgc cggcaagagc 300
agcttctaca agaacctgct gtggatcatc aagaccaaga gcgccgccta ccccgtgatc 360
aagggcacct acaacaacac cggcaaccag cccatcctgt acttctgggg cgtgcaccac 420
ccccccgaca ccaacgagca gaacaccctg tacggcagcg gcgacaggta cgtgaggatg 480
ggcaccgaga gcatgaactt cgccaagagc cccgagatcg ccgccaggcc cgccgtgaac 540
ggccagaggg gcaggatcga ctactactgg agcgtgctga agcccggcga gaccctgaac 600
gtggagagca acggcaacct gatcgccccc tggtacgcct acaagttcgt gagcaccaac 660
aacaagggcg ccgtgttcaa gagcaacctg cccatcgaga actgc 705

<210> SEQ ID NO 20
<211> LENGTH: 708
<212> TYPE: DNA
<213> ORGANISM: Influenza A virus

<400> SEQUENCE: 20
tgcaagatcc tgaacaaggc ccccctggac ctgaggggct gcaccatcga gggctggatc 60
ctgggcaacc ccgagtgcga gctgctgctg ggcgaccaga gctggagcta catcgtggag 120
aggcccaccg cccagaacgg catctgctac cccggcaccc tgaacgaggt ggaggagctg 180
aaggccctga tcggcagcgg cgagagggtg gagaggttcg agatgttccc caagagcacc 240
tgggccggcg tggacaccac caggggcgtg accgccgcct gcagccacaa gggcaagagc 300
aagagcttct acaagaacct gctgtggatc atcaagacca agagcgccgc ctaccccgtg 360

```
atcaagggca cctacaacaa caccggcaac cagcccatcc tgtacttctg gggcgtgcac    420

cacccccccg acaccaacga gcagaacacc ctgtacggca gcggcgacag gtacgtgagg    480

atgggcaccg agagcatgaa cttcgccaag agccccgaga tcgccgccag gcccgccgtg    540

aacggccaga ggggcaggat cgactactac tggagcgtgc tgaagcccgg cgagaccctg    600

aacgtggaga gcaacggcaa cctgatcgcc ccctggtacg cctacaagtt cgtgagcacc    660

aacaacaagg gcgccgtgtt caagagcaac ctgcccatcg agaactgc                 708
```

<210> SEQ ID NO 21
<211> LENGTH: 699
<212> TYPE: DNA
<213> ORGANISM: Influenza A virus

<400> SEQUENCE: 21

```
tgcagcatcg acggcaaggc ccccatcagc ctgggcgact gcagcttcgc cggctggatc     60

ctgggcaacc ccgagtgcga ggacctgatc ggcaagacca gctggagcta catcgtggag    120

aagcccaacc ccaccaacgg catctgctac cccggcaccc tggagaacga ggaggagctg    180

aggctgaagt tcagcggcgt gctggagttc agcaagttcg aggccttcac cagcaacggc    240

tggggcgccg tgaacagcac caagggcgtg accgccgcct gcagccacaa cggcaagagc    300

agcttcttca ggaacatggt gtggctgatc caccagagcg gcacctaccc cgtgatcagg    360

aggaccttca acaacaccaa gggcagggac gtgctgatgg tgtggggcgt gcaccacccc    420

gccaccctga aggagcacca ggacctgtac aagaaggaca gcagctacgt ggccgtgggc    480

agcgagagct acaacaggag gttcaccccc gagatcagca ccaggcccaa ggtgaacggc    540

caggccggca ggatgacctt ctactggacc atcgtgaagc ccggcgaggc catcaccttc    600

gagagcaacg gcgccttcct ggcccccagg tacgccttcg agctggtgag cctgggcaac    660

ggcaagctgt tcaggagcga cctgaacatc gagagctgc                           699
```

<210> SEQ ID NO 22
<211> LENGTH: 699
<212> TYPE: DNA
<213> ORGANISM: Influenza A virus

<400> SEQUENCE: 22

```
tgcgacctgg acggcgtgaa gcccctgatc ctgagggact gcagcgtggc cggctggctg     60

ctgggcaacc ccgagtgcga ggagttcctg aacgtgcccg agtggagcta catcgtggag    120

aaggccaacc ccgccaacga cctgtgctac cccggcaact tcaacgacta cgaggagctg    180

aagcacctgc tgagcaggat caaccacttc gagaagatcc agatcatccc caagagcagc    240

tggagcgacc acgagaccgg cggcgtgagc gccgcctgcg ccagccacaa cggcaagagc    300

agcttcttca ggaacgtggt gtggctgatc aagaagaaca acgcctaccc caccatcaag    360

aggagctaca acaacaccaa ccaggaggac ctgctggtgc tgtggggcat ccaccacccc    420

aacgacgccg ccgagcagac caagctgtac cagaacccca ccacctacat cagcgtgggc    480

accagcaccc tgaaccagag gctggtgccc aagatcgcca ccaggagcaa ggtgaacggc    540

cagagcggca ggatggagtt cttctggacc atcctgaagc ccaacgacgc catcaacttc    600

gagagcaacg gcaacttcat cgcccccgag tacgcctaca agatcgtgaa gaagggcgac    660

agcaccatca tgaagagcga gctggagtac ggcaactgc                           699
```

<210> SEQ ID NO 23

```
<211> LENGTH: 560
<212> TYPE: PRT
<213> ORGANISM: Influenza A virus

<400> SEQUENCE: 23

Met Glu Thr Val Ser Leu Ile Thr Ile Leu Leu Val Val Thr Val Ser
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Asn Asn Val Pro Val Thr His Ala Lys
        35                  40                  45

Glu Leu Leu His Thr Glu His Asn Gly Met Leu Cys Ala Thr Ser Leu
    50                  55                  60

Gly His Pro Leu Ile Leu Asp Thr Cys Thr Ile Glu Gly Leu Ile Tyr
65                  70                  75                  80

Gly Asn Pro Ser Cys Asp Leu Leu Leu Gly Gly Arg Glu Trp Ser Tyr
                85                  90                  95

Ile Val Glu Arg Pro Ser Ala Val Asn Gly Leu Cys Tyr Pro Gly Asn
            100                 105                 110

Val Glu Asn Leu Glu Glu Leu Arg Ser Leu Phe Ser Ser Ala Arg Ser
        115                 120                 125

Tyr Gln Arg Ile Gln Ile Phe Pro Asp Thr Ile Trp Asn Val Ser Tyr
    130                 135                 140

Ser Gly Thr Ser Lys Ala Cys Ser Asp Ser Phe Tyr Arg Ser Met Arg
145                 150                 155                 160

Trp Leu Thr Gln Lys Asn Asn Ala Tyr Pro Ile Gln Asp Ala Gln Tyr
                165                 170                 175

Thr Asn Asn Gln Gly Lys Asn Ile Leu Phe Met Trp Gly Ile Asn His
            180                 185                 190

Pro Pro Thr Asp Thr Ala Gln Thr Asn Leu Tyr Thr Arg Thr Asp Thr
        195                 200                 205

Thr Thr Ser Val Ala Thr Glu Glu Ile Asn Arg Thr Phe Lys Pro Leu
    210                 215                 220

Ile Gly Pro Arg Pro Leu Val Asn Gly Leu Gln Gly Arg Ile Asp Tyr
225                 230                 235                 240

Tyr Trp Ser Val Leu Lys Pro Gly Gln Thr Leu Arg Ile Arg Ser Asn
                245                 250                 255

Gly Asn Leu Ile Ala Pro Trp Tyr Gly His Ile Leu Ser Gly Glu Ser
            260                 265                 270

His Gly Arg Ile Leu Lys Thr Asp Leu Lys Arg Gly Ser Cys Thr Val
        275                 280                 285

Gln Cys Gln Thr Glu Lys Gly Gly Leu Asn Thr Thr Leu Pro Phe Gln
    290                 295                 300

Asn Val Ser Lys Tyr Ala Phe Gly Asn Cys Ser Lys Tyr Ile Gly Ile
305                 310                 315                 320

Lys Ser Leu Lys Leu Ala Val Gly Leu Arg Asn Val Pro Ser Arg Ser
                325                 330                 335

Ser Arg Gly Leu Phe Gly Ala Ile Ala Gly Phe Ile Glu Gly Gly Trp
            340                 345                 350

Ser Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
    370                 375                 380

Lys Ile Thr Ser Lys Val Asn Asn Ile Val Asp Lys Met Asn Lys Gln
```

```
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Val Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Gln Glu Glu Ser Lys Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Ile Ala Met Gly Phe Ala Ala Phe
    530                 535                 540

Leu Phe Trp Ala Met Ser Asn Gly Ser Cys Arg Cys Asn Ile Cys Ile
545                 550                 555                 560


<210> SEQ ID NO 24
<211> LENGTH: 9
<212> TYPE: PRT
<213> ORGANISM: Influenza A virus

<400> SEQUENCE: 24

Pro Ser Ile Gln Ser Arg Gly Leu Phe
1               5


<210> SEQ ID NO 25
<211> LENGTH: 9
<212> TYPE: PRT
<213> ORGANISM: Influenza A virus

<400> SEQUENCE: 25

Pro Gln Arg Lys Lys Arg Gly Leu Phe
1               5


<210> SEQ ID NO 26
<211> LENGTH: 9
<212> TYPE: PRT
<213> ORGANISM: Influenza A virus

<400> SEQUENCE: 26

Pro Gln Ile Glu Thr Arg Gly Leu Phe
1               5


<210> SEQ ID NO 27
<211> LENGTH: 9
<212> TYPE: PRT
<213> ORGANISM: Influenza A virus

<400> SEQUENCE: 27

Pro Ser Arg Ser Ser Arg Gly Leu Phe
1               5


<210> SEQ ID NO 28
<211> LENGTH: 9
```

-continued

```
<212> TYPE: PRT
<213> ORGANISM: Influenza A virus

<400> SEQUENCE: 28

Pro Ala Ile Ala Thr Arg Gly Leu Phe
1               5
```